(12) United States Patent
Rieger et al.

(10) Patent No.: US 7,378,400 B2
(45) Date of Patent: *May 27, 2008

(54) METHOD TO REDUCE AN INFLAMMATORY RESPONSE FROM ARTHRITIS

(75) Inventors: Jayson M. Rieger, Charlottesville, VA (US); Donald L. Kimpel, Charlottesville, VA (US); Joel M. Linden, Charlottesville, VA (US); Gail W. Sullivan, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/222,664

(22) Filed: Sep. 9, 2005

(65) Prior Publication Data

US 2006/0100169 A1 May 11, 2006

Related U.S. Application Data

(63) Continuation-in-part of application No. 10/379,154, filed on Mar. 3, 2003, now Pat. No. 7,226,913, which is a continuation of application No. 09/827,083, filed on Apr. 5, 2001, now Pat. No. 6,531,457, which is a continuation of application No. 09/333,387, filed on Jun. 15, 1999, now Pat. No. 6,232,297, application No. 11/222,664, which is a continuation-in-part of application No. 10/263,379, filed on Oct. 1, 2002, now Pat. No. 7,214,665.

(60) Provisional application No. 60/135,573, filed on May 24, 1999, provisional application No. 60/133,374, filed on May 10, 1999, provisional application No. 60/124,316, filed on Mar. 12, 1999, provisional application No. 60/118,029, filed on Feb. 1, 1999, provisional application No. 60/326,517, filed on Oct. 1, 2001, provisional application No. 60/383,200, filed on May 24, 2001.

(51) Int. Cl.
*A61K 31/70* (2006.01)

(52) U.S. Cl. .................................. 514/46; 514/47

(58) Field of Classification Search ............... 514/46, 514/47, 423

See application file for complete search history.

(56) References Cited

U.S. PATENT DOCUMENTS

| | | |
|---|---|---|
| 3,892,777 A | 7/1975 | Gruenman et al. |
| 4,012,495 A | 3/1977 | Schmeichen et al. |
| 4,193,926 A | 3/1980 | Schmiechen et al. |
| 4,242,345 A | 12/1980 | Brenner et al. |
| 4,665,074 A | 5/1987 | Amschler |
| 4,824,660 A | 4/1989 | Angello et al. |
| 4,879,296 A | 11/1989 | Daluge et al. |
| 4,938,949 A | 7/1990 | Borch et al. |
| 4,956,345 A | 9/1990 | Miyasaka et al. |
| 4,965,271 A | 10/1990 | Mandell et al. |
| 4,968,697 A | 11/1990 | Hutchison |
| 5,070,877 A | 12/1991 | Mohiuddin et al. |
| 5,096,906 A | 3/1992 | Mandell et al. |
| 5,124,455 A | 6/1992 | Lombardo et al. |
| 5,140,015 A | 8/1992 | Olsson et al. |
| 5,189,027 A | 2/1993 | Miyashita et al. |
| 5,272,153 A | 12/1993 | Mandell et al. |
| 5,278,150 A | 1/1994 | Olsson et al. |
| 5,298,508 A | 3/1994 | Jacobson et al. |
| 5,364,862 A | 11/1994 | Spada et al. |
| 5,561,134 A | 10/1996 | Spada et al. |
| 5,565,462 A | 10/1996 | Eitan et al. |
| 5,593,975 A | 1/1997 | Cristalli |
| 5,593,976 A | 1/1997 | Mongelli et al. |
| 5,665,754 A | 9/1997 | Feldman et al. |
| 5,668,139 A | 9/1997 | Belardinelli et al. |
| 5,696,254 A | 12/1997 | Mansour et al. |
| 5,731,296 A | 3/1998 | Sollevi |
| 5,756,706 A | 5/1998 | Mansour et al. |
| 5,776,940 A | 7/1998 | Daluge et al. |
| 5,854,081 A * | 12/1998 | Linden et al. ............ 436/501 |
| 5,877,180 A * | 3/1999 | Linden et al. ............ 514/45 |
| 5,932,558 A | 8/1999 | Cronstein et al. |
| 5,998,386 A | 12/1999 | Feldman |
| 6,004,945 A | 12/1999 | Fukunaga |
| RE36,494 E | 1/2000 | Olsson et al. |

(Continued)

FOREIGN PATENT DOCUMENTS

EP 0488336 B1 6/1992

(Continued)

OTHER PUBLICATIONS

Okusa et al., "Selective A2A Adenosine Receptor Activation Reduces Ischemia-Reperfusion Injury in Rat Kidney," American J. Physiology: Heart and Circulatory Physiology, 277(3, Pt. 2), F404-F412 (Sep. 1999).*

Peirce et al., "Selective A2A Adenosine Receptor Activation Reduces Skin Pressure Ulcer Formation and Inflammation," American J. Physiology: Heart and Circulatory Physiology, 281(1, Pt. 2), H67-H72 (Jul. 2001).*

Sullivan et al., "Cyclic AMP-Dependent Inhibition of Human Neutrophil Oxidation Activity by Substituted 2-Propynycyclohexyl Adenosine A2A Receptor Agonists," British J. Pharmacology, 132(5), 1017-1026 (2001).*

(Continued)

*Primary Examiner*—L. E. Crane
(74) *Attorney, Agent, or Firm*—Schwegman, Lundberg & Woessner, P.A.

(57) ABSTRACT

The present invention provides a therapeutic method for treating an inflammatory response caused by autoimmune stimulation, comprising the administration to a patient in need thereof of an antiinflammatory amount amount of an $A_{2A}$ adenosine receptor agonist. The autoimmune stimulation can be caused by arthritis, particularly rheumatoid arthritis. Optionally, the method includes administration of a type IV PDE inhibitor.

27 Claims, 5 Drawing Sheets

U.S. PATENT DOCUMENTS

| | | | |
|---|---|---|---|
| 6,020,321 A | 2/2000 | Cronstein et al. | |
| 6,020,339 A | 2/2000 | Perrier et al. | |
| 6,034,089 A | 3/2000 | Han et al. | |
| 6,060,481 A * | 5/2000 | LaNoue et al. | 514/263.34 |
| 6,117,878 A * | 9/2000 | Linden | 514/263.34 |
| 6,232,297 B1 * | 5/2001 | Linden et al. | 514/46 |
| 6,303,619 B1 * | 10/2001 | Linden | 514/263.34 |
| 6,322,771 B1 * | 11/2001 | Linden et al. | 424/9.3 |
| 6,326,359 B1 | 12/2001 | Monaghan et al. | |
| 6,332,771 B1 | 12/2001 | Adams et al. | |
| 6,339,072 B2 | 1/2002 | Martin et al. | |
| 6,350,735 B1 * | 2/2002 | Monaghan | 514/46 |
| 6,387,889 B1 | 5/2002 | Endo et al. | |
| 6,448,235 B1 * | 9/2002 | Linden et al. | 514/46 |
| 6,514,949 B1 * | 2/2003 | Linden et al. | 514/46 |
| 6,525,032 B2 * | 2/2003 | Mantell et al. | 514/45 |
| 6,531,457 B2 * | 3/2003 | Linden et al. | 514/46 |
| 6,545,002 B1 * | 4/2003 | Linden et al. | 514/263.2 |
| 6,624,158 B2 * | 9/2003 | Mantell et al. | 514/217.06 |
| 6,670,334 B2 * | 12/2003 | Linden et al. | 514/46 |
| 6,936,596 B2 | 8/2005 | Konno et al. | |
| 7,214,665 B2 | 5/2007 | Linden et al. | |
| 7,226,913 B2 | 6/2007 | Linden et al. | |
| 2002/0032168 A1 | 3/2002 | Mantrell et al. | |
| 2002/0058641 A1 | 5/2002 | Mantell et al. | |
| 2003/0013675 A1 | 1/2003 | Yeadon et al. | |
| 2003/0162742 A1 | 8/2003 | Linden et al. | |
| 2005/0182018 A1 | 8/2005 | Linden et al. | |
| 2005/0282831 A1 | 12/2005 | Baeuglehole et al. | |

FOREIGN PATENT DOCUMENTS

| | | |
|---|---|---|
| EP | 0700908 | 3/1998 |
| EP | 1150991 | 4/2004 |
| HU | 174074 | 10/1979 |
| WO | WO-93/22328 A1 | 11/1993 |
| WO | WO-95/11681 | 5/1995 |
| WO | WO95/11681 A1 * | 5/1995 |
| WO | WO-96/02553 | 2/1996 |
| WO | WO96/02553 A2 * | 2/1996 |
| WO | WO-96/04280 | 2/1996 |
| WO | WO-98/47509 | 10/1998 |
| WO | WO-98/57651 | 12/1998 |
| WO | WO-98/57651 A1 | 12/1998 |
| WO | WO-99/34804 | 7/1999 |
| WO | WO99/34804 A1 * | 7/1999 |
| WO | WO-99/38877 | 8/1999 |
| WO | WO-99/41267 | 8/1999 |
| WO | WO-99/62518 | 12/1999 |
| WO | WO-99/63938 | 12/1999 |
| WO | WO-99/67263 | 12/1999 |
| WO | WO-99/67264 | 12/1999 |
| WO | WO-99/67265 | 12/1999 |
| WO | WO-99/67266 | 12/1999 |
| WO | WO-00/44763 | 1/2000 |
| WO | WO-00/23457 | 4/2000 |
| WO | WO-00/72799 | 12/2000 |
| WO | WO-00/78774 | 12/2000 |
| WO | WO00/78774 A2 * | 12/2000 |
| WO | WO-00/78777 | 12/2000 |
| WO | WO-01/94368 | 12/2001 |
| WO | WO-02/09701 | 2/2002 |
| WO | WO02/09701 A1 * | 2/2002 |
| WO | WO-02/096462 | 12/2002 |
| WO | WO02/096462 A1 * | 12/2002 |
| WO | WO-03/014137 | 2/2003 |
| WO | WO-03/086408 A1 | 10/2003 |

OTHER PUBLICATIONS

Beers et al. (eds.), The Merck Manual of Diagnosis and Therapy, 17th Edition, Merck & Co., Rahway, NJ, Jan. 1999, only pp. 924-925 supplied.*

Venes et al. (eds.), Taber's Cyclopedic Medical Dictionary, 19th Edition, F. A. Davis, Philadelphia, PA, 2001, only pp. 960-961 supplied.*

Ishiwata et al., "Further Characterization of a CNS Adenosine A2A Receptor Ligand [11C] KF18446 with in vitro Autoradiography and in vivo Tissue Uptake," Annals on Nuclear Medicine, 14(2), 81-89 (2000).*

Sullivan et al., "A2A Adenosine Receptor Activation Improves Survival in Mouse Models of Endotoxemia and Sepsis," Journal of Infectioous Diseases, 189, 1897-1904 (May 15, 2004).*

Moore et al., "A2A Adenosine Receptor Agonists Modify Inflammatory Responses in an E. coli Peritonitis Murine Septic Shock Model," Abstract (###) from the 43rd Annual Meeting of the Infectious Disease Society of America, Oct. 6-9, 2005, San Francisco, California.*

Hogan et al., "Inhibiting the Inflammatory Response in Joint Sepsis," Arthroscopy, 17(3), 311-315 (Mar. 2001).*

Abiru, T., et al., "Nucleosides and nucleotides. 107.2-(cycloalkylalkynyl)adenosines: adenosine A2 receptor agonists with potent antihypertensive effects", Journal of Medicinal Chemistry, 35(12), (Jun. 12, 1992),2253-2260.

Adah, S. A., "Synthesis of Complex Ethynyladenosines Using Organic Triflic Enolates in Palladium-Catalyzed Reactions: Potential Agonists for the Adenosine A2 Receptor", Tetrahedron, 53, (1997),6747-6754.

Ali, H., et al., "Methylxanthines Block Antigen-induced Responses in RBL-2H3 Cells Independently of Adenosine Receptors or Cyclic AMP: Evidence for Inhibition of Antigen Binding to IgE", Journal of Pharmacology and Experimental Therapeutics, 258, (1991),954-962.

Andersson, P., et al., "Anti-anaphylactic and anti-inflammatory effects of xanthines in the lung", Curr. Clin. Pract. Ser., (1985),187-192.

Baraldi, Pier G., et al., "Synthesis and Biological Activity of a New Series of N6-Arylcarbamoyl, 2-(Ar)alkynyl-N6-arylcarbamoyl, and N6-Carboxamido derivatives of adenosine-5'-N-ethyluronamide as A1 and A3 Adenosine receptor agonists", Journal of Medicinal Chemistry, 41(17), (Aug. 13, 1998),3174-3185.

Beers, Mark H., et al., "The Merck Manual of Diagnosis and Therapy", Merck and Company Jan. 1999, 924-925.

Berkich, D. A., et al., "Evidence of Regulated Coupling of A1 Adenosine Receptors by Phosphorylation in Zucker Rats.", American Journal of Physiology, 268 (4), (Apr. 1995),E693-E704.

Bhattacharya, S., et al., "Effects of Long-Term Treatment With the Allosteric Enhancer, PD81,723, on Chinese Hamster Ovary Cells Expression Recombitant Human A1 Adenosine Receptors", Molecular Pharmacology, 50 (1), (Jul. 1996), 104-111.

Bhattacharya, S., et al., "The Allosteric Enhancer, PD 81,723, Stabilizes Human A1 Adenosine Receptor Coupling to G Proteins", Biochimica et Biophysica Acta, 1265 (1), (Feb. 1995), 15-21.

Bridges, Alexander J., et al., "N6-[2-(3,5-Dimethozyphenyl)-2-(2-Methylphenyl)-Ethyl]Adenosine and Its Uronamide Derivatives. Novel Adenosine Agonists With Both Highly Affinity and High Selectivity for the Adenosine A2 Receptor", Journal of Medicinal Chemistry, 31(7), (Jul. 1988),1282-1285.

Bruns, R. F., "Adenosine Receptors—Roles and Pharmacology", Biological Actions of Extracellular ATP, 603, Annals of The New York Academy of Sciences,(1990), 211-226.

Bruns, R. F., et al., "Characterization of the A2 Adenosine Receptor Labeled by [3H]NECA in Rat Striatal Membranes", Molecular Pharmacology, 29, (1986), 331-346.

Buster, B., et al., "The Effect of Adenosine Receptor Agonists on Neutrophil Pleocytosis and Blood-Brain Barrier Pathophysiology in Experimental Bacterial Meningitis", Abstract of the Interscience Conference on Antimicrobial Agents and Chemotherapy, 37, Abstract No. B-72,(1997), 39.

Camaioni, E, et al., "Adenosine receptor agonists: synthesis and bilogical evaluation of the diastereoisomers of 2-(3-Hydroxy-3-phenyl-1-propyn-1-yl)NECA", *Bioorganic & Medicinal Chemistry*, 5(12), (Dec. 1997),2267-75.

Carruthers, A. M., et al., "Hypotensive Responses to the Putative Adenosine A3 Receptor Agonist N6-20(4-Aminophenyl)-Ethyladenosine in the Rat", *Drug Development Research*, 30, (1993), 147-152.

Cassada, D C., et al., "Adenosine A2A agonist reduces paralysis after spinal cord ischemia: correlation with A2A receptor expression on motor neurons", *Annals of Thoracic Surgery*, 74(3), (Sep. 2002),846-9; discussion 849-50.

Cassada, D C., et al., "Adenosine A2A analogue ATL-146e reduces systemic tumor necrosing factor and spinal cord capillary platelet-endothelial cell adhesion molecule-1 expression after spinal cord ischemia", *Journal of Vascular Surgery*, 35(5), (May 2002),994-98.

Cassada, D C., et al., "Adenosine A2A analogue improves neurologic outcome after spinal cord trauma in the rabbit.", *Journal of Trauma-Injury Infection & Critical Care*, 53(2), (Aug. 2002),225-9.

Cassada, D C., et al., "Adenosine analogue reduces spinal cord reprefusion Injury in a time-dependent fashion", *Surgery*, 130(2), (Aug. 2001),230-35.

Cassada, D C., et al., "An adenosine A2A agonist, ATL-146e, reduces paralysis and apoptosis during rabbit spinal cord reperfusion.", *Journal of Vascular Surgery*, 34(3), (Sep. 2001),482-88.

Cassada, D C., et al., "Systemic adenosine A2 agonist ameliorates ischemic reperfusion injury in the rabbit spinal cord", *Annals of Thoracic Surgery*, 72(4), (Oct. 2001),1245-50.

Cembrzynska-Nowak, M, et al., "Elevated Release of Tumor Necrosis Factor-alpha with Interferon-gamma by Bronchoalveolar Leukocytes From Patients With Bronchial Asthma.", *American Review of Respiratory Disease*, 147(2), (1993),291-295.

Cothran, D. L., et al., "Ontogeny of Rat Myocardial A1 Adenosine Receptors", *Biol Neonate*, 68 (2), (1995), 111-118.

Cristalli, G., "2-Alkynyl Derivatives of Adenosine an Adenosine-5'-N-ethyluronamide as Selective Agonists at A2 Adenosine Receptors", *Journal of Medicinal Chemistry*, 35 (13), (1992), 2363-2368.

Cristalli, G, et al., "2-Alkynyl Derivatives of Adenosine-5'-N-ethyluronamide: Selective A2 Adenosine Receptor Agonists with Potent Inhibitory Activity on Platelet Aggregation", *Journal of Medicinal Chemistry*, 37, (1994),1720-1726.

Cristalli, G., "2-Aralkynyl and 2-Heteroalkynyl Derivatives of Adenosine-5'-N-ethyluronamide as Selective A2a Adenosine Receptor Agonists", *J. Med. Chem.*, 38 (9), (1995), 1462-1472.

Cronstein, B. N., "Adenosine Modulates the Generation of Superoxide Anion by Stimulated Human Neutrophils Via International With a Specific Cell Surface Receptor", *Annals New York Academy of Science*, 451, (1985),291-314.

Cronstein, B. N., "Adenosine; A Physiologic Modulator Of Superoxide Anion Generated By Human Neutrophils. Adenosine Acts Via An A2 Receptor On Human Neutrophils", *Journal of Immunology*, 135 (2), (1985), 1366-1371.

Cronstein, B. N., "Engagement of Adenosine Receptors Inhibits Hydrogen Peroxide (H2O2) Release by Activated Human Neutrophils", *Clinical Immunology and Immunopathology*, 42(1), (1987),76-85.

Cronstein, B. N., "Methotrexate Inhibits Leukocyte Influx Into Inflammatory Sites Via The Adenosine (A2) Receptor", *Clinical Research*, 41 (2), (1993), 244A.

Cronstein, B N., et al., "Neutrophil Adherence to Endothelium is Enhanced Via Adenosine A1 Receptors and Inhibited Via Adenosine A2 Receptors", *The Journal of Immunology*, 148 (7), (1992), 2201-2206.

Cronstein, N., et al., "Occupancy Of Adenosine Receptors Raises Cyclic AMP Alone And In Synergy With Occupancy Of Chemoattractant Receptors And Inhibits Membrane Depolarization", *Biochemical Journal*, 252 (3), (1988), 709-715.

Cronstein, B. N., "The Adenosine/Neutrophil Paradox Resolved: Human Neutrophils Possess Both A1 and A2 Receptors That Promote Chemotaxis and Inhibits O2 Generation, Respectively", *Journal of Clinical Investigation*, 85 (4), (1990), 1150-1157.

Day, Y.-J., et al., "Protection From Ischemic Liver Injury by Activation of A2A Adenosine Receptors During Reperfusion: Inhibition of Chemokine Induction", *American Journal of Physiology Gastrointest inal and Liver Physiology*, 286, (2004),G285-293.

Day, Y. J., et al., "Renal Protection from Ischemia Mediated by A2A Adenosine Receptors on Bone Marrow-Derived Cells.", *Journal of Clinical Investigation*, 112(6), (2003),883-891.

De La Harpe, J., "Adenosine Regulates the Respiratory Burst Of Cytokine—Triggered Human Neutrophils Adherent To Biological Surfaces", *Journal Of Immunology*, 143(2), (1989),596-602.

De Moraes, V. L., et al., "Effect of Cyclo-Oxygenase Inhibitors and Modulators of Cyclic AMP Formation of Lipopolysaccharide-Induced Neutrophil Infiltration in Mouse Lung", *British Journal of Pharmacology*, 117,(1996), 1792-1796.

De Zwart, M, et al., "5-N-Substituted Carboxamidoadenosines as Agonists for Adenosine Receptors", *Journal of Medicinal Chemistry*, 42(8), (Apr. 22, 1999),1384-1392.

Dechatelet, L R., et al., "Mechanism of the Luminol-Dependent Chemiluminescence of Human Neutrophils", *The Journal of Immunology*, 129 (4), (1982), 1589-1593.

Dela Harpe, J., et al., "Adenosine Regulates the Respiratory Burst of Cytokine-Triggered Human Neutrophils Adherent to Biologic Surfaces", *J. Immunol.*, vol. 143, (1989),596.

Dinarello, C. A., "Interleukin-1 And Tumor Necrosis Factor: Effector Cytokines In Autoimmune Diseases", *Seminars in Immunology*, 4, (1992),133-145.

Doyle, M. P., et al., "Nucleoside-induced Arteriolar Constriction: a Mast Cell-dependent Response", *American Journal of Physiology*, (May 1994), H2042-H2050.

Elzein, E., "Design, Synthesis And Biological Evaluation Of 2-(4-Substituted-N-Pyrazolyl)-Adenosine Derivatives As Novel Short Acting Adenosine A2A Receptor Agonists", *Drug Development Research*, 50 (1), Abstracts From Purines 2000: Biochemical, Pharmacological, and Clinical Perspectives: Abstract No. 061,(May 2000), 64.

Fang, G. D., et al., "A New Selective Adenosine A2a Receptor Agonist, Improves Survival in E. coli O26:B6 Lipopolysaccharide (LPS)-Induced Experimental Murine Endotoxemia", *Journal of Investigative Medicine*, Abstract No. 797,(2000),148A.

Fenster, M. S., et al., "Activation of adenosine A2 alpha receptors inhibits mast cell degranulation and mast cell-dependent vasoconstriction", *Microcirculation*, 7(2), (2000),129-135.

Feoktistov, I., et al., "Adenosine A2b receptors", *The American Society for Pharmacological and Experimental Therapeutics*, 49 (4), (1997), 381-402.

Feoktistov, I., et al., "Role of Adenosine in Asthma", *Drug Development Research*, 39, (1996), 333-336.

Ferrante, A., "Optimal Conditions for Simultaneous Purification of Mononuclear and Polymorphonuclear Leucocytes From Human Blood by the Hypaque-Ficoll Method", *Journal of Immunological Methods*, 36(2), (1980),109-117.

Figler, R. A., et al., "Reconstitution of Bovine A1 Adenosine Receptors and G Proteins in Phospholipid Vesicles: .Beta..Gamme.-Subunit Composition Influences Guanine Nucleotide Exchange and Agonist Binding", *Biochemistry*, 36 (51), (1997), 16288-16299.

Figler, R. A., et al., "Reconstruction of Recombinant Bovine A1 Adenosine Receptors in Sf9 Cell Membranes with Recombitant G Proteins of Defined Composition.", *Molecular Pharmacology*, 50 (6), (Dec. 1996), 1587-1595.

Firestein, G. S., "Adenosine Regulating Agents: A Novel Approach to Inflammation and Inflammatory Arthritis", *Clinical Research*, 41(2), (1993),170A.

Fiser, S M., et al., "Adenosine A2A receptor activation decreases reperfusion injury associated with high-flow reperfusion.", *Journal of Thoracic & Cardiovascular Surgery*, 124(5), (Nov. 2002),973-8.

Fozard, J. R., "Adenosine A3 Receptors Mediate Hypotension in the Angiotensin II-supported Circulation of the Pithed Rat", *British Journal of Pharmacology*, 109 (1), (1993),3-5.

Francis, J. E., "Highly Selective Adenosine A2 Receptor Agonists in a Series of N-Alkylated 2-Aminoadenosines", *Journal of Medicinal Chemistry*, 34 (8), (1991), 2570-2579.

Frangogiannis, N G., et al., "Myocardial Ischemia: Mechanisms, Reperfusion, Protection", *Birkhuser Verlag*, M. Karmazyn, et al., (1996),236-284.

Gao, Z., et al., "A2B Adenosine and P2Y2 Receptors Stimulate Mitogen-activated Protein Kinase in Human Embryonic Kidney-293 Cells. Cross-talk Between Cyclic AMP and Protein Kinase c Pathways", *Journal of Biological Chemistry*, 274(9), (Feb. 26, 1999),5972-5980.

Gao, Z, et al., "Purification of A1 Adenosine Receptor-G-protein Complexes: Effects of Receptor Down-regulation and Phosphorylation on Coupling", *Biochemical Journal*, 338 (Pt3), (Mar. 1999), 729-736.

Gilchrist, A., et al., "Antagonists of the Receptor-G Protein Interface Block Gi-coupled Signal Transduction", *Journal of Biological Chemistry*, 273 (24), (Jun. 12, 1998),14912-14919.

Girardi, N, et al., "Inflammatory Aneurysm of the Ascending Aorta and Aortic Arch", *Ann. Thor. Surg.*, 64, (1997),251.

Glover, D. K., et al., "Bolus injection of DWH-146E, A Novel Adenosine A2A Receptor Agonist for Use in Vasodilator Stress Imaging", *Journal of Nuclear Cardiology*, 7 (4), Abstract No. 44.20,(Sep. 23, 2000),1 p.

Glover, D. K., et al., "Characterization of a New, Highly Selective Adenosine A2A Receptor Agonist with Potential Use in Pharmacologic Stress Perfusion Imaging", *Circulation*, 100, Abstract (1999),1 pg.

Glover, D K., et al., "Pharmacological stress myocardial perfusion imaging with the potent and selective A(2A) adenosine receptor agonists ATL193 and ATL146e administered by either intravenous infusion of bolus injection", *Circulation*, 104(10), (Sep. 4, 2001),1181-1187.

Glover, D. K., et al., "Pharmacological stress thallium scintigraphy with 2-cyclohexymethylidenehydrazinoadenosine (WRC-0470). A novel, short-acting adenosine A2A receptor agonist.", *Circulation*, 94(7), (Oct. 1, 1996),1726-1732.

Glover, D. K., et al., "Vasodilator Stress Imaging Using New Adenosine A2A Receptor Agonists Administered by Bolus Injection", *J. Am. Coll. Cardiol.*, 35, Abstract,(2000).

Griswold, D. E., et al., "Effects of Selective Phosphodieasterase Type IV Inhibitor, Rolipram, on Fluid and Cellular Phases of Inflammatory Response", *Chemical Abstracts*, 119, Abstract No. 173828e,(1993),p. 49.

Hanlon, W. A., "rTNF alpha Facilitate Human Polymorphonuclear Leukocyte Adherence to Fibrinogen Matrices With Mobilization of Specific and Tertiary But Not Azurophilic Granule Markers", *Journal of Leukocyte Biology*, 50 (1), (1991), 43-48.

Hanlon, et al., "rTNF Facilitates Human Polymorphonuclear Leukocyte Adherence to Fibrinogen Matrices with Mobilization to Specific and Tertiary but Not Azurophilic Granule Markers", *J. Leukocyte Biol.*, vol. 50, (1991),43.

Hartung, H. P., "Immune Mediated Demyelination", *Annals of Neurology*, 33 (6), (Jun. 1993), 563-567.

Heller, L. J., et al., "Effect of Adenosine on Histamine Release and Atrioventricular Conduction During Guinea Pig Cardia Anaphylaxis", *Circulation Research*, 62(6), (Jun. 1988),1147-1158.

Holmes, "Restenosis After Percutaneous Transluminal Coronary Angioplasty (PTCA): A Report From the PTCA of the National Heart, Lung, and Blood Institute", *American Journal of Cardiology*, 53, (1984),77C-81C.

Homma, H, et al., "Nucleosides and nucleotides. 112. 2-(1-Hexyn-1-yl)adenosine-5'-uronamides: a new entry of selective A2 adenosine receptor agonists with potent antihypertensive activity.", *Journal of Medicinal Chemistry*, 35(15), (Jul. 1992),2881-90.

Hussain, T., et al., "125I-APE Binding to Adenosine Receptors in Coronary Artery: Photoaffinity Labeling With 125I-azidoAPE", *The Journal of Pharmacology and Experimental Therapeutics*, 276 (1), (Jan. 1998), 284-288.

Hutchison, A. J., "2-(Arylalkylamino)Adenosine-5'-Uronamides: A New Class of Highly Selective Adenosine A2 Receptor Ligands", *Journal of Medicinal Chemistry*, 33 (7), (1990), 1919-1924.

Hutchison, A. J., "CGS 21680C, an A2 Selective Adenosine Receptor Agonist With Preferential Hypotensive Activity", *The Journal of Pharmacology and Experimental Therapeutics*, 251 (1), (1989), 47-55.

Iannone, M. A., "Effects of Adenosine on Human Neutrophil Function and Cyclic AMP Content", *In: Topics and Perspectives in Adenosine Research*, Eds. E. Gerlach et al., Springer-Verlag, Berlin, Germany,(1986), 286-298.

Imagawa, D. K., et al., "The Role of Tumor Necrosis Factor in Allograft Rejection", *Transplantation*, 51, (Jan. 1991),57-62.

Ishiwata, K., et al., "Further Characterization of a CNS Adenosine A2a. Receptor Ligand[11C]KF18446 with in vitro Autoradiography and in vivo Tissue Uptake", *Annals of Nuclear Medicine*, 14 (2), Abstract Only, Obtained from Chemicals Abstracts, 133, Abstract No. 346544, HCAPlus Accession No. 480897 (2000),(2000),81-89.

Ito, B. R., et al., "Role of Cardiac Mast Cells In Complement C5a-Induced Myocardial Ischemia", *American Journal of Physiology*, 264 (5), Part 2 of Two Parts,(May 1993), H1346-H1354.

Jarvis, M. F., "[3H]CGS 21680, A Selective A2 Adenosine Receptor Agonist Directly Labels A2 Receptors in Rat Brain.", *Journal of Pharmacology and Experimental Therapeutics*, 251(3), (Dec. 1989),888-893.

Jolly, S. R., et al., "Effects of Lodoxamide on Ischemic Reperfused Myocardium", *Journal of Cardiovascular Pharmacology*, 4 (3), (1982), 441-448.

Kaminuma, et al., "Effect of T-440, a Novel Type IV Phosphodiesterase Inhibitor, on Allergen-Induced Immediate and Late Asthmatic Reaction and Leukocyte Infiltration into the Airways of Guinea Pigs", *International Archives of Allergy & Immunology*, 112(4), (1997),406-411.

Keller, A. M., et al., "Acute Reoxygeneration Injury in the Isolated Rat Heart: Role of Resident Cardiac Mast Cells", *Circulation Research*, 63(6), (Dec. 1988),1044-1052.

Kennedy, A. P., et al., "Covalent Modification of Transmembrane Span III of the A1 Adenosine Receptor With an antagonist Photoaffinity Prove.", *Molecular Pharmacology*, 50, (Oct. 1996), 789-798.

Klotz, Karl-Norbert, et al., "2-Substituted N-ethylcarboxamidoadenosine derivatives as high-affinity agonists at human A3 adenosine receptors", *Naunyn-Schmiedebergs Archives of Pharmacology*, 360(2), (Aug. 1999),103-108.

Kollias-Baker, C., et al., "Allosteric Enhancer PD 81,723 Acts by Novel Mechanism to Potentiate Cardiac Actions of Adenosine", *Circulation Research*, 75(6), (Dec. 1994),961-971.

Koshiba, M., "Patterns of A2A Extracellular Adenosine Receptor Expression in Different Functional Subsets of Human Peripheral T Cells", *The FASEB Journal*, Abstract No. 703,38, (1999), A944.

Koshiba, M, et al., "Patterns of A2A Extracellular Adenosine Receptor Expression in Different Functional Subsets of Human Peripheral T Cells. Flow Cytometry Studies With Anti-A2A Receptors Monoclonal Antibodies.", *Molecular Pharmacology*, 55 (3), (Mar. 1999), 614-624.

Leclerc, G., "Percutaneous Arterial Gene Transfer in a Rabbit Model", *Journal of Clinical Investigation*, 90 (3), (1992), 936-944.

Legrand-Poels, S., "Activation of Human Immunodeficiency Virus Type 1 by Oxidative Stress", *AIDS Research and Human Retroviruses*, 6(12), (1990), 1389-1397.

Lette, J., et al., "Safety of Dipyridamote Testing in 73,806 Patients: The Multicenter Dipyridamole Safety Study", *Journal of Nuclear Cardiology*, 2 (1), (1995), 3-17.

Linden, J., "(125I)Aminobenzyladenosine, a New Radioligand with Improved Specific Binding to Adenosine Receptors in Heart", *Circulation Research*, 56 (2), (Feb. 1985), 279-284.

Linden, J., et al., "Adenosine Receptors", *In: Handbook of Receptos and Channels—G Protein Coupled Receptors*, Chapter 2, Edited by S.J. Peroutka, Published by CRC Press, Boca Raton, FL,(1994), 29-44.

Linden, J., "Allosteric Enhancement of Adenosine Receptors", *In: Purinergic Approaches in Experimental Therapeutics*, Chapter 5, Edited by K.A. Jacobson et al., and Published by Wiley-Liss, Inc.,(1997), 85-97.

Linden, J., "Calculating the Dissociation Constent of an Unlabeled Compound from the Concentration Required to Displace Radiolabel Binding by 50%", *Journal of Cyclic Nucletide Research*, 8 (3), (1982), 163-172.

Linden, J, "Cloned Adenosine A3 Receptors: Pharmacological Properties, Species Differences and Receptor Functions.", *Trends in Pharmacological Sciences*, 15 (8), (Aug. 1994), 298-306.

Linden, J., "Molecular Cloning and Functional Expression of a Sheep A3 Adenosine Receptor with Widespread Tissue Distribution", *Molecular Pharmacology*, 44 (3), (Sep. 1993), 524-532.

Linden, J., "Recombinant Techniques as Applied to the Study of A1 Adenosine Receptors", In: *Adenosine and Adenine Nucleotides: From Molecular Biology to Integrative Physiology*, Chapter 2, Kluwer Academic Publishers, Boston, Edited by L. Belardinelli,(1995), 15-19.

Linden, J, et al., "The Structure and Function of A1 and A2B Adenosine Receptors", *Life Science*, 62 (17/18), (1998), 1519-1524.

Luthin, D. R., et al., "Adenosine Receptors", *Biomembranes*, 2B, (1996), 321-347.

Luthin, D. R., "Characterization of Two Affinity States of Adenosine A2a Receptors With a New Radioligand 2-[2-(4-amino-3-[125I]iodophenyl)Ethylamino]Adenosine.", *Molecular Pharmacology*, 47 (2), (Feb. 1995), 307-313.

Luthin, D. R., et al., "Comparison of A4 and A2a Binding Sites in Striatum and COS Cells Transfected With Adenosine A2a Receptors.", *The Journal of Pharmacology and Experimental Therapeutics*, 272, (Feb. 1995), 511-518.

Luthin, D. R., et al., "Photoaffinity Labeling With 2(-)[2-(4-azido-3(-)[125I]-iodophenyl)ethylamino]Adenosine and Autoradiography With 2(-)[2-(4-amino-3(-)[125I]iodophenyl)ethylamino]Adenosine of A2a Adenosine Receptor in Rat Brain.",*Journal of Neurochemistry*, 65 (5), (Nov. 1995), 2072-2079.

Mager, Paul P., "Neutal network approaches applied to selective A2a adenosine receptor agonists", *Med. Chem. Res.*, vol. 8, No. 6, (1998), 277-290.

Mahan, L. C., et al., "Cloning and Expression of an A1 Adenosine Receptor from Rat Brain", *Molecular Pharmacology*, 40 (1), (Jul. 1991), 1-7.

Mannel, D. N., "Tumor Necrosis Factor: A Cytokine Involved in Toxic Effects of Endotoxin", *Reviews of Infectious Diseases*, 9, (1987),S602-S606.

March, Jerry, *Advanced Organic Chemistry: Reactions, Mechanisms, and Structure*, Fourth Edition, John Wiley & Sons,(1992),p. 400.

Martin, P. L., et al., "Characterization of 8-(N-methylisopropyl)amino-N6-(5'- andohydroxy-endonorbomyl)-9-methyladenine (WRC-0571), a Highly Potent and Selective, Non-xanthine Antagonist of A1 Adenosine Receptors.", *The Journal of Pharmacology and Experimental Therapeutics*, 276 (2), (Feb. 1996),490-499.

Martin, P. L., et al., "Pharmacology of 2-cyclohexylmethylidenehydrazinoadenosine (WRC-0470), a Novel, Short-acting Adenosine A2A Receptor Agonist That Produces Selective Coronary Vasodilation", *Drug Development Research*, 40 (4), (1997), 313-324.

Matherne, G. P., et al., "Transgenic A1 Adenosine Receptor Overexpression Increases Myocardial Resistance to Ischemia", *Proceedings of the National Academy of Science*, 94, (Jun. 1997), 6541-6546.

Matsuyama, T., "Cytokines and HIV Infection: is AIDS a Tumor Necrosis Factor Disease?", *AIDS*, 5(12), (1991),1405-1417.

McGarrity, S. T., "Inhibition of Neutrophil Superoxide Anion Generation by Platelet Products: Role of Adenine Nucleotides", *Journal of Leukocyte Biology*, 44(5), (1988),411-421.

McGarrity, S. T., "Regulation of Human Neutrophil Function by Adenine Nucleotides", *Journal of Immunology*, 142(6), (1989), 1986-1994.

McLaughlin, D. P., et al., "Hemodynamic and Metabolic Correlates of Dipyridamole-Induced Myocardial Thallium-201 Perfusion Abnormalities in Multivessel Coronary Artery Disease.", *American Journal of Cardiology*, 73 (16), (Jun. 1994), 1159-1164.

McPherson, J A., "Adenosine A(2A) receptor stimulation reduces inflammation and neointimal growth in a murine carotid ligation model", *Arteriosclerosis, Thrombosis & Vascular Biology*, 21(5), (May 2001),791-6.

McPherson, J A., et al., "Effect of Prolonged Adenosine A2A Receptor Activation on Neointimal Formation in the Injured Mouse Carotid Artery", *The FASEB Journal*, Abstract No. 299.2, (1999),A367.

McPherson, J. A., et al., "Prolonged Adenosine A2a Receptor Stimulation Reduces Inflammation and Neointima Formation in a Murine Carotoid Ligation Model", *Supplement to Circulation*, 100 (18), Abstract No. 3652,(Nov. 2, 1999),1 pg.

Merritt, H. R., et al., "Abnormal Q Waves are Common Early in AMi and Do Not Predict Decreased Myocardial Salvage With Thrombolytic Therapy", *Special Issue Journal of American College of Cardiology*, Abstract No. 895-77,(Feb. 1994),195A.

Miyamoto, F, et al., "Retinal Cytokine Response in Mouse Alkali-Burned Eye", *Opthalmic Res.*, 30, (1997),168.

Mizumura, T., et al., "PD 81,723, an Altosteric Enhancer of the A1 Adenosine Receptor, Lowers the Threshold for Ischemic Preconditioning in Dogs.", *Circulation Research*, 79 (3), (Sep. 1996), 415-423.

Molnar-Kimber, K. L., et al., "Modulation of TNF alpha and IL-1 beta From Endotoxin-Stimulated Monocytes by Selective PDE Isozyme Inhibitors", *Agents & Actions*, 39, (1993),C77-C79.

Mumby, S. M., et al., "G-protein alpha-subunit expression, myristoylation, and membrane association in COS cells", *Proceedings of the National Academy of Sciences*, 87 (2), (Jan. 1990), 728-732.

Nabel, Elizabeth G., "Site-Specific Gene Expression in Vivo by Direct Gene Transfer into the Arterial Wall", *Science*, 249, (1990),1285-1288.

Newman, K. D., "Adenovirus-mediated Gene Transfer into Normal Rabbit Arteries Results in Prolonged Vascular Cell Activation, Inflammation and Neointimal Hyperplasia", *Journal of Clinical Investigation*, 96 (6), (1995), 2955-2965.

Nielson, C. P., "Effects of Adenosine of Polymorphonuclear Leucocyte Function, Cyclic 3': 5'-adenosine Monophosphate, and Intracellular Calcium", *British Journal of Pharmacology*, 97(3), (1989),882-888.

Niiya, K., "2-(N'Alkylidenehydrazino)Adenosines: Potent and Selective Coronary Vasodilators", *Journal of Medicinal Chemistry*, 35 (24), (1992), 4557-4561.

Nolte, "Reduction of Postischemic Leukocyte-Endothelium Interaction by Adenosine Via A2 Receptor", *Biological Abstract*, 94 (11), Abstract No. 116779,(1992),1 pg.

O'Regan, M. H., et al., "Adenosine Receptor Agonists Inhibit the Release of y-Aminobutyric Acid (GABA) From the Ischemic Rat Cerebral Cortex", *Chemical Abstracts*, 117, Abstract No. 104867p,(1992), 170.

Okusa, M D., "A(2A) Adenosine Receptor-Mediated Inhibition of Renal Injury and Neutrophil Adhesion", *American Journal of Physiology—Renal Fluid & Electrolyte Physiology*, 279(5), (2000),F809-F818.

Okusa, M D., "Enhanced Protection from Renal Ischemia: Reperfusion Injury With A2A-Adenosine Receptor Activation and PDE 4 Inhibition", *Kidney International*, 59(6), (2001),2114-2125.

Okusa, Mark D., "Selective A2A adenosine receptor activation reduces ischemia-reperfusion injury in rat kidney", *Am. J. Physiol.*, vol. 277 (3, Pt 2), (1999),F404-F412.

Olsson, R. A., "N6 Substituted N-Alkyladenosine-5'-Uronamides: Bifunctional Ligands Having Recognition Groups for A1 and A2 Adenosine Receptors", *Journal of Medicinal Chemistry*, 29 (9), (1986), 1683-1689.

Peart, J, et al., "Adenosine-mediated cardioprotection in Ischemic-reperfused mouse heart.", *Journal of Cardiovascular Pharmacology*, 39(1), (2002),117-129.

Peet, N. P., "Conformationally Restrained, Chiral (Phenylidopropyl)Amino-Substituted Pyrazole[3,4-d]Pyrimidines and Purines With Selectivity for Adenosine A1 and A2 Receptors", *Journal of Medicinal Chemistry*, 35 (17), (1992), 3263-3269.

Peirce, S. M., et al., "Attenuation of I/R Injury In Skin Using A Selective A2A Adenosine Receptor Agonist", *FASEB Journal*, 14 (4), Abstract No. 333.1,(2000), A466.

Peirce, S M., "Selective A(2A) adenosine receptor activation reduces skin pressure ulcer formation and inflammation", *American Journal of Physiology—Heart & Circulatory Physiology*, 281(1), (Jul. 2001),H67-74.

Pennell, R L., et al., "Inflammatory abdominal aortic aneurysms: A thirty-year review", *J. Vasc. Surg.*, 2, (1985),859.

Pfister, J. R., et al., "Synthesis and Biological Evaluation of the Enantiomers of the Potent and Selective A1- adenosine Antagonist 1,3-dipropyl-8-[2-(5,6-epoxynorbonyl)]-xanthine", *Journal of Medicinal Chemistry*, 40 (12), (Jun. 1997), 1773-1778.

Pulle, V., et al., "Design, Synthesis And Pharmacological Evaluation Of 2(1-Alkyl-Pyrazole-4-YL) Adenosine Derivatives As Short Acting Adenosine A2A Receptor Agonists", *Drug Development Research*, 50 (1), Abstracts From Purines 2000: Biochemical, Pharmacological and Clinical Perspectives: Abstract No. 062, (2000), 64.

Ranhosky, A., et al., "The Safety of Intravenous Dipyridamole Thallium Myocardial Perfusion Imaging", *Circulation*, 81(4), (Apr. 1990), 1205-1209.

Rieger, J. M., et al., "Design, Synthesis, and Evaluation of Novel A2A Adenosine Receptor Agonists", *J. Med. Chem.*, 44, (2001),531-539.

Riou, L M., "Influence of propranolol, enalaprilat, verapamil, and caffeine on adeonsine A(2A)-receptor-mediated coronary vasodilation", *Journal of the American College of Cardiology*, 40(9), (Nov. 6, 2002),1687-94.

Roberts, P. A., "Inhibition by Adenosine of Reactive Oxygen Metabolite Production of Human Polymorphonuclear Leucocytes", *Biochemical Journal*, 227(2), (1985),669-674.

Robeva, A. S., "Double Tagging Recombinant A1- and A2A-Adenosine Receptors With Hexahistidine and the Flag Epitope. Development of an Efficient Generic Protein Purification Procedure. ", *Biochemical Pharmacology*, 51(4), Feb. 1996), 545-555.

Robeva, A. S., et al., "Molecular Characterization of Recombinant Human Adenosine Receptors", *Drug Development Research*, 39, (1996), 243-252.

Rosin, D. L., et al., "Immunohistochemical Localization of Adenosine A2A Receptors in the Rat Central Nervous System", *The Journal of Comparative Neurology*, 401, (1998), 163-186.

Ross, S D., "Selective Adenosine-A2A Activation Reduces Lung Reperfusion Injury Following Transplantation", *Journal of Heart & Lung Transplantation*, 18(10), (1999),994-1002.

Ross, R., "The Pathogenesis of Atherosclerosis: A Perspective for the 1990s", *Nature*, 362, (Apr. 29, 1993),801-809.

Rothe, G. A., "Flow Cytometric Measurement of the Respiratory Burst Activity of Phagocytes Using Dihydrorhodamide 123", *Journal of Immunological Methods*, 138(1), (1991),133-135.

Sawmiller, D. R., et al., "Effects of Xanthine Amine Congener on Hypoxic Resistence and Venous and Epicardial Adenosine Concentrations.", *Cardiovascular Research*, 28 (5), (May 1994), 604-609.

Schiffmann, S. N., et al., "Distribution of adenosine A2 receptor mRNA in the human brain", *Neurosceince Letters*, 130, (1991), 177-181.

Schlack, et al., "Adenosine A2-Receptor Activation at Reperfusion reduces Infarct Size and Improves Myocardial Wall Function in Dog Heart", *Biological Abstract*, 96 (6), Abstract No. 67801,(1993),1 pg.

Schrier, D. J., "The Effects of Adenosine Agonists on Human Neutrophil Function", *Journal of Immunology*, 137 (10), (1986), 3284-3289.

Seekamp, A., "Ischemia—Reperfusion Injury", *Agents and Actions Supplements*, 41, (1993),137-152.

Sharief, M. K., et al., "Elevated Serum Levels of Tumor Necrosis Factor-alpha in Guillain-Barre Syndrome", *Annals of Neurology*, 33, (Jun. 1993),591-596.

Sharma, H S., et al., "Role of cytokines in myocardial ischemia and reperfusion", *Med. of Imflamm.*, 6, (1987),175.

Shepherd, R. K., et al., "Adenosine-induced Vasoconstriction in Vivo. Role of the Mast Cell and A3 Adenosine Receptor.", *Circulation Research*, 78 (4), (Apr. 1996), 627-634.

Sipka, S., "Adenosine Induced Delay of Expression of AIDS Virus, HIV, in H9T Cells", *Acta. Biochimica et Biophysica Hungarica*, 23(1), (1988),75-82.

Siragy, H. M., et al., "Sodium Intake Markedly Alters Renal Interstitial Fluid Adenosine", *Hypertension*, 27 (3 Pt 1), (Mar. 1996), 404-407.

Smits, Paul, et al., "Cardiovascular effects of two xanthines and the relation to adenosine antagonism", *Clinical Pharmacology and Therapeutics*, 45 (6), (1989), 593-599.

Sullivan, G. W., "Adenosine (ADO) Modulated Endotoxin and TNF-Induced PMN Activation", *Clinical Research*, 41(2), (1993),172A.

Sullivan, Gail W., et al., "Cyclic AMP-Dependent Inhibition of Human Neutrophil Oxidative Activity by Substitited 2-Propnylcyclohexyl Adenosine A2A Receptor Agonists", *British Journal of Pharmacology*, 132(5), Abstract Only, Obtained from Chemical Abstracts, 135, Abstract No. 40644, HCAPlus No. 216425 (2001),(2001),1017-1026.

Sullivan, G W., et al., "Interactions of Human Neutrophils with Leukotoxic Streptococci", *Infection and Immunity*, 30 (1), (1980), 272-280.

Sullivan, G. W., et al., "Neutrophil A2A Adenosine Receptor Inhibits Inflammation in a Rat Model of Meningitis: Synergy with the Type IV Phosphodiesterase Inhibitor, Rolipram", *The Journal of Infectious Diseases*, 180, No. 5, (1999), 1550-1560.

Sullivan, G. W., "Role of A2A Adenosine Receptors in Inflammation", *Drug Development Research*, 45 (3/4), (1998), 103-112.

Sullivan, G. W., et al., "The role of inflammation in vascular diseases", *Journal of Leukocyte Bilogy*, 67, (May 2000), 591-602.

Sullivan, G. W., "The Specific Type IV Phosphodiesterase Inhibitor Rolipram Combined with Adenosine Reduces Tumor Necrosis Factor-a-Primed Neutrophil Oxidative Activity", *International Journal of Immunonopharmacology*, 17(10), (1995),793-803.

Sullivan, G. W., "Two Methylxanthines, Pentoxifylline (PTX) and Caffeine (CAF) Have Divergent Effects on Tumor Necrosis Factor (TNF)-Primed Human Neutrophil (PMN) Activation", *Clinical Research*, 41(2), (1993),p. 172A.

Takiguchi, Yoshiharu, et al., "Early administration of YT-146, an adenosine A2 receptor agonist, inhibits neointimal thickening after rat femoral artery endothelium injury", *European Journal of Pharmacology* (1995) 205-207, (Mar. 16, 2002),205-207.

Topol, E. J., "Randomised Trial of Coronary Intervention With Antibody Against Platelet IIb/IIIa integrin for Reduction of Clinical Restenosis: Results at Six Months", *The Lencet*, 343(8902), (1994),881-886.

Tracey, K. J., "Cachectin/Tumor Necrosis Factor Induces Cachexia, Anemia, and Inflammation", *Journal of Experimental Medicine*, 167, (Mar. 1988),1211-1227.

Tucker, A. L., et al., "A1 adenosine receptors. Two amino acids are responsible for species differences in ligand recognition", *Journal of Biological Chemistry*, 269(45), (Nov. 11, 1994),27900-27906.

Ueeda, M., "2- Alkoxyadenosines: Potent and Selective Agonists at the Coronary Artery A2 Adenosine Receptor", *Journal of Medicinal Chemistry*, 34(4), (1991), 1334-1339.

Ukena, D., et al., "Species Differences in Structure-Activity Relationships of Adenosine Agonists and Xanthine Antagonists at Brain A1 Adenosine Receptors", *FEBS Letters*, 209 (1) , (Dec. 1986), 122-128.

Underwood, D. C., et al., "Inhibition of Antigen-Induced Bronchoconstriction and Eosinophil Infiltration in the Guinea by the Cyclic AMP-Specific Phosphodiesterase Inhibitor, Rollpram", *Chemical Abstracts*, 119 (16), Abstract No. 173975a,(1993), 67.

Van Calker, D., et al., "Adenosine Regulates via Two Different Types of Receptors, the Accumulation of Cyclic Amp in Cultured Brain Cells", *Journal of Neurochemistry*, 33, (1979), 999-1005.

Van Calker, D., "Carbamazepine Distinguishes Between Adenosine Receoters That Mediate Different Second Messenger Responses", *European Journal of Pharmacology*, 206 (4), (1991), 285-290.

Venes, et al., "Taber's Cyclopedic Medical Dictionary", 960-961.

Vittori, S, et al., "2-alkenyl and 2-alkyl derivatives of adenosine and adenosine-5'-N-ethyluronamide: different affinity and selectivity of E- and Z- diastereomers at A2A adenosine receptors.", *Journal of Medicinial Chemistry*, 39(31), (Oct. 1996),4211-7.

Walker, Blair A., et al., "Adenosine A2a Receptor Activation Delays Apoptosis in Human Neutrophils", *The American Association of Immunologists*, (1997), 2926-2931.

Walker, D I., et al., "Inflammatory Aneurysms of the Abdominal Aorta", *Brit. J. Surg.*, 59, (1972),609.

Wan, A. A., et al., "Binding of the Adenosine A2 Receptor Ligand (3H)CGS 21680 to Human and Rat Brain: Evidence for Multiple Affinity Sites", *Journal of Neurochemistry*, (1990), 1763-1771.

Wolff, A. A., et al., "Ventricular Arrhythmias Parallel Cardiac Histamine Efflux After Coronary Artery Occlusion in the Dog", *Agents and Actions*, 25 (3/4), (1988), 296-306.

Yoneyama, F., "Vasodepressor Mechanisms of 2-(1-octynyl)-Adenosine (YT-146), a Selective Adenosine A2 Receptor Agonist, Involve the Opening of Glibenclamide-sensitive K+ Channels", *European Journal of Pharmacology*, 213 (1), (1992), 199-204.

Zablocki, J., et al., "Novel Short Acting Coronary Vasodilators That Are Functionally Selective For The A2A Receptor Based On 2-Heterocyclic Substituted Adenosine Derivatives", *Drug Development Research*, 50 (1), Abstracts From Purines 2000: Biochemical, Pharmacological and Clinical Perspectives: Abstract No. 059,(May 2000),p. 63.

"U.S. Appl. No. 11/739,680, Preliminary Amendment filed Apr. 24, 2007", 3 pgs.

"U.S. Appl. No. 11/739,680, Supplemental Preliminary Amendment filed Jul. 18, 2007", 6 pgs.

"U.S. Appl. No. 08/272,821, Notice of Allowance mailed 08-05-098", 3 pgs.

"U.S. Appl. No. 09/003,930, Non-Final Office Action mailed Nov. 4, 1998", 7 pgs.

"U.S. Appl. No. 09/003,930, Final Office Action mailed Aug. 6, 1999", 6 pgs.

"U.S. Appl. No. 09/003,930, Preliminary Amendment filed Feb. 8, 1999", 5 pgs.

"U.S. Appl. No. 09/003,930, Response filed May 4, 1999 to Non-Final Office Action mailed Nov. 4, 1998", 12 pgs.

"U.S. Appl. No. 09/003,930, Response filed Nov. 4, 1999 to Final Office Action mailed Aug. 6, 1999", 10 pgs.

"U.S. Appl. No. 09/333,387, Non-Final Office Action mailed Jul. 13, 2000", 5 pgs.

"U.S. Appl. No. 09/333,387, Notice of Allowance mailed Mar. 7, 2001", 4 pgs.

"U.S. Appl. No. 09/333,387, Notice of Allowance mailed Aug. 25, 2000", 2 pgs.

"U.S. Appl. No. 09/333,387, Supplemental Amendment filed Aug. 28, 2000", 2 pgs.

"U.S. Appl. No. 09/543,385, Notice of Allowance mailed Mar. 25, 2002", 5 pgs.

"U.S. Appl. No. 09/543,385, Notice of Allowance mailed Sep. 24, 2001", 5 pgs.

"U.S. Appl. No. 09/543,385, Preliminary Amendment filed Apr. 4, 2000", 2 pgs.

"U.S. Appl. No. 09/543,385, Supplemental Preliminary Amendment filed Aug. 31, 2000", 6 pgs.

"U.S. Appl. No. 09/827,083, Notice of Allowance mailed Sep. 10, 2002", 6 pgs.

"U.S. Appl. No. 09/827,083, Preliminary Amendment filed Apr. 5, 2001", 5 pgs.

"U.S. Appl. No. 09/827,083, Response filed Dec. 10, 2002 to Notice of Allowance mailed Sep. 10, 2002", 2 pgs.

"U.S. Appl. No. 10/263,379 Advisory Action mailed Mar. 1, 2006", 7 pgs.

"U.S. Appl. No. 10/263,379 Advisory Action mailed Apr. 11, 2006", 5 pgs.

"U.S. Appl. No. 10/263,379 Final Office Action mailed Nov. 1, 2006", 6 pgs.

"U.S. Appl. No. 10/263,379 Final Office Action mailed Nov. 9, 2005", 17 pgs.

"U.S. Appl. No. 10/263,379 Final Office Action mailed Nov. 23, 2004", 46 pgs.

"U.S. Appl. No. 10/263,379 Non Final Office Action mailed Apr. 25, 2005", 15 pgs.

"U.S. Appl. No. 10/263,379 Non Final Office Action mailed Jun. 14, 2006", 10 pgs.

"U.S. Appl. No. 10/263,379 Non Final Office Action mailed Jun. 17, 2004", 54 pgs.

"U.S. Appl. No. 10/263,379 Notice of allowance mailed Dec. 12, 2006", 5 pgs.

"U.S. Appl. No. 10/263,379 Response filed Feb. 8, 2006 to Final Office Action mailed Nov. 9, 2005", 19 pgs.

"U.S. Appl. No. 10/263,379 Response filed Feb. 23, 2005 to Final Office Action mailed Nov. 23, 2004", 20 pgs.

"U.S. Appl. No. 10/263,379 Response filed Apr. 4, 2006 to Advisory Action mailed Mar. 1, 2006", 19 pgs.

"U.S. Appl. No. 10/263,379 Response filed May 2, 2006 to Advisory Action mailed Apr. 11, 2006", 15 pgs.

"U.S. Appl. No. 10/263,379 Response filed Sep. 11, 2006 to Non Final Office Action mailed Jun. 14, 2006", 15 pgs.

"U.S. Appl. No. 10/263,379 Response filed Sep. 26, 2005 to Non Final Office Action mailed Apr. 25, 2005", 19 pgs.

"U.S. Appl. No. 10/263,379 Response filed Oct. 18, 2004 to Non Final Office Action mailed Jun. 17, 2004", 25 pgs.

"U.S. Appl. No. 10/263,379 Response filed Nov. 21, 2006 to Final Office Action mailed Nov. 1, 2006", 13 pgs.

"U.S. Appl. No. 10/379,154, Final Office Action mailed Feb. 17, 2004", 4 pgs.

"U.S. Appl. No. 10/379,154, Final Office Action mailed Mar. 30, 2006", 5 pgs.

"U.S. Appl. No. 10/379,154, Non-Final Office Action mailed Jun. 17, 2004", 4 pgs.

"U.S. Appl. No. 10/379,154, Non-Final Office Action mailed Aug. 1, 2005", 5 pgs.

"U.S. Appl. No. 10/379,154, Non-Final Office Action mailed Aug. 8, 2003", 4 pgs.

"U.S. Appl. No. 10/379,154, Non-Final Office Action mailed Dec. 15, 2004", 5 pgs.

"U.S. Appl. No. 10/379,154, Notice of Allowance mailed Jan. 4, 2007", 5 pgs.

"U.S. Appl. No. 10/379,154, Response filed Apr. 4, 2007 to Notice of Allowance and Allowability mailed Jan. 4, 2007", 3 pgs.

"U.S. Appl. No. 10/379,154, Response filed May 16, 2005 to Non-Final Office Action mailed Dec. 15, 2004", 7 pgs.

"U.S. Appl. No. 10/379,154, Response filed May 17, 2004 to Final Office Action mailed Feb. 17, 2004", 6 pgs.

"U.S. Appl. No. 10/379,154, Response filed May 31, 2006 to Final Office Action mailed Mar. 30, 2006", 7 pgs.

"U.S. Appl. No. 10/379,154, Response filed Sep. 17, 2004 to Non-Final Office Action mailed Jun. 17, 2004", 6 pgs.

"U.S. Appl. No. 10/379,154, Response filed Nov. 6, 2003 to Non-Final Office Action mailed Aug. 8, 2003", 8 pgs.

"U.S. Appl. No. 10/379,154, Response filed Dec. 1, 2005 to Non-Final Office Action mailed Aug. 1, 2005", 7 pgs.

"U.S. Appl. No. 10/412,726 Final office action mailed Oct. 8, 2004", 28 pgs.

"U.S. Appl. No. 10/412,726 Final office action mailed Dec. 5, 2005", 13 pgs.

"U.S. Appl. No. 10/412,726 Non Final office action mailed Mar. 16, 2005", 15 pgs.

"U.S. Appl. No. 10/412,726 Non Final office action mailed Apr. 7, 2004", 25 pgs.

"U.S. Appl. No. 10/412,726 Non Final office action mailed Oct. 30, 2006", 18 pgs.

"U.S. Appl. No. 10/412,726 Response filed Feb. 8, 2005 to Final office action mailed Oct. 8, 2004", 22 pgs.

"U.S. Appl. No. 10/412,726 Response filed Apr. 27, 2007 to Non Final office action mailed Oct. 30, 2006", 23 pgs.

"U.S. Appl. No. 10/412,726 Response filed May 5, 2006 to Final office action mailed Dec. 5, 2005", 23 pgs.

"U.S. Appl. No. 10/412,726 Response filed Jul. 9, 2004 to Non Final office action mailed Apr. 7, 2004", 20 pgs.

"U.S. Appl. No. 10/412,726 Response filed Sep. 16, 2005 to Non Final office action mailed Mar. 16, 2005", 25 pgs.

"U.S. Appl. No. 10/412,726 Final Office Action mailed Jul. 19, 2007", FOAR,10 pgs.

* cited by examiner

METHOD TO REDUCE AN INFLAMMATORY RESPONSE FROM ARTHRITIS

CROSS-REFERENCE TO RELATED APPLICATIONS

This application is a continuation-in-part of U.S. patent application Ser. No. 10/379,154, filed Mar. 3, 2003, now U.S. Pat. No. 7,226,913, issued on Jun. 5, 2007; which is a continuation of U.S. patent application Ser. No. 09/827,083, filed Apr. 5, 2001, now U.S. Pat. No. 6,531,457, issued on Mar. 11, 2003; which is a continuation of U.S. application Ser. No. 09/333,387, filed Jun. 15, 1999, now U.S. Pat. No. 6,232,297, issued on May 15, 2001, which claims priority from U.S. provisional patent application Ser. Nos. 60/118,029, filed Feb. 1, 1999, 60/124,316, filed Mar. 12, 1999, 60/133,374, filed May 10, 1999 and 60/135,573, filed May 24, 1999 all of which are incorporated by reference herein.

This application is also a continuation-in-part of U.S. application Ser. No. 10/263,379, filed Oct. 1, 2002, now U.S. Pat. No. 7,214,665, issued on May 8, 2007, which claims priority from U.S. provisional patent application Ser. No. 60/326,517, filed Oct. 1, 2001, and U.S. provisional patent application Ser. No. 60/383,200, filed May 24, 2001, all of which are incorporated by reference herein.

GOVERMENT FUNDING

The invention described herein was made with government support under Grant Number (RO1-HL37942), awarded by the National Institutes of Health. The United States Government has certain rights in the invention.

BACKGROUND OF THE INVENTION

The inflammatory response serves the purpose of eliminating harmful agents from the body. There is a wide range of pathogenic insults that can initiate an inflammatory response including infection, allergens, autoimmune stimuli, immune response to transplanted tissue, noxious chemicals, and toxins, ischemia/reperfusion, hypoxia, mechanical and thermal trauma. Inflammation normally is a very localized action which serves in expulsion, attenuation by dilution, and isolation of the damaging agent and injured tissue. The body's response becomes an agent of disease when it results in inappropriate injury to host tissues in the process of eliminating the targeted agent, or responding to a traumatic insult.

The release of inflammatory cytokines such as tumor necrosis factor-alpha (TNFα) by leukocytes is a means by which the immune system combats pathogenic invasions, including infections. TNFα stimulates the expression and activation of adherence factors on leukocytes and endothelial cells, primes neutrophils for an enhanced inflammatory response to secondary stimuli and enhances adherent neutrophil oxidative activity (H. S. Sharma et al., Med. of Inflamm., 6, 175 (1987)). In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and non-oxidative (e.g., myeloperoxidase and other enzymes) inflammatory activity. Inappropriate and over-release of cytokines can produce counterproductive exaggerated pathogenic effects through the release of tissue-damaging oxidative and non-oxidative products (K. G. Tracey et al., J. Exp. Med., 167, 1211 (1988); and D. N. Männel et al., Rev. Infect. Dis., 9 (suppl. 5), S602-S606 (1987)). For example, TNFα can induce neutrophils to adhere to the blood vessel wall and then to migrate through the vessel to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

Human rheumatoid arthritis (RA) is the most common form of inflammatory arthritis and is a chronic disorder of unknown origin with variable courses of disease. The majority of patients with RA have a progressive course which leads to destruction of joint tissue, instability of joints, loss of function and mobility, and increased mortality.

The dysregulated immune response in RA is driven by type 1 helper T cell (Th1) cytokines, including interleukin-12 (IL-12), interferon-γ (IFN-γ), and TNFα (See, M. Feldmann et al., Curr. Dir. Autoimmun., 3, 188-199 (2001); H. Schulze-Koops et al., Best. Pract. Res. Clin. Rheumatol., 15, 677-691 (2001); M. Feldmann et al., Rheumatology (Oxford), 38, 3-7 (1999); and Y. Morita et al., Arthritis Rheum., 41, 306-314 (1998)). Cytokines and chemokines in the synovial tissues trigger the adhesion, recruitment, and infiltration of inflammatory cells and the release of other inflammatory mediators and reactive oxygen species, leading to macroscopic tissue damage and the clinical symptoms of RA (Mechanisms and Models in Rheumatoid Arthritis. 1 ed. San Diego, Calif.: Academic Press (1995)). Recent studies have shown that TNFα and IL-1β are major proinflammatory cytokines in this inflammatory disorder, and are currently targets for therapeutic intervention (M. Feldmann et al., Curr. Dir. Autoimmun., 3, 188-199 (2001); M. Feldmann et al., Transplant Proc., 2001; 33, 2085-2086 (2001); M. Feldmann, Nat. Rev. Immunol., 2, 364-371 (2002); and R. Maini et al., Lancet, 348, 824-825 (1996)).

Standard RA therapy includes the use of immunomodulators, biologic agents, and corticosteroids, all of which have limited efficacy and carry significant risk of toxicity. Methotrexate is the gold standard treatment for RA.

Steroids act through multiple pathways, and besides their immunosuppressive effect, have multiple side effects including osteoporosis, worsening diabetes, and adrenal suppression. Traditional non-steroidal anti-inflammatory drugs (NSAIDs) such as ibuprofen, aspirin and indomethacin non-selectively inhibit both COX-1 and -2. The more recently described COX-2 inhibitors (rofecoxib/Vioxx, Celecoxib/Celebrx and valdecoxib/Bextra) were developed to decrease gastric toxicity by avoiding COX-1 inhibition. These agent impart their anti-inflammatory effects through action on the COX-2 enzyme, and provide relief of pain and some mild anti-inflammatory effect, but do not stop progression of disease. The COX-2 inhibitors also avoid the platelet-inhibiting effect of traditional NSAIDS, which may play a role in the recent reports of increased cardiovascular risk with COX-2 inhibitors.

The latest strategies for the treatment of RA focus on specifically targeting the dysregulated cytokines. TNF inhibitors (Adalimumab, Etanercept, Infliximab) and the IL-1 receptor antagonist Anakinra block two of the prime mediators of inflammation, but predispose patients to bacterial and granulomatous infections. Even these sophisticated biological response modifiers have met with varying success, and often require multi-drug combination therapy to control disease. The current paradigm for RA management is to treat aggressively and early in the disease because joint swelling can rapidly proceed to erosion (bony destruction) and loss of cartilage and joint space (J. O'Dell, *N. Engl. J. Med.*, 350, 2591-2602 (2004)). Once these bony changes occur they are essentially irreversible, and can be painful, debilitating, and may leave the patient with surgery (e.g., joint replacement) as the only option. Clearly there is a need for new therapies with improved safety as well as the identification of new targets for suppression of inflammation and immunosuppression that can be used in conjunction with other agents.

It is well known that adenosine and some analogs of adenosine that nonselectively activate adenosine receptor subtypes decrease neutrophil production of inflammatory oxidative products (B. N. Cronstein et al., *Ann. N.Y. Acad. Sci.*, 451, 291 (1985); P. A. Roberts et al., *Biochem. J.*, 227, 669 (1985); D. J. Schrier et al., *J. Immunol.*, 137, 3284 (1986); B. N. Cronstein et al., *Clinical Immunol. and Immunopath.*, 42, 76 (1987); M. A. Iannone et al., in *Topics and Perspective in Adenosine Research*, E. Gerlach et al., eds., Springer-Verlag, Berlin, p. 286 (1987); S. T. McGarrity et al., *J. Leukocyte Biol.*, 44, 411421 (1988); J. De La Harpe et al., *J. Immunol.*, 143, 596 (1989); S. T. McGarrity et al., *J. Immunol.*, 142, 1986 (1989); and C. P. Nielson et al., *Br. J. Pharmacol.*, 97, 882 (1989)). For example, adenosine has been shown to inhibit superoxide release from neutrophils stimulated by chemoattractants such as the synthetic mimic of bacterial peptides, f-met-leu-phe (fMLP), and the complement component $C_5a$ (B. N. Cronstein et al., *J. Immunol.*, 135, 1366 (1985)). Adenosine can decrease the greatly enhanced oxidative burst of PMN (neutrophil) first primed with TNF-$\alpha$ and then stimulated by a second stimulus such as f-met-leu-phe (G. W. Sullivan et al., *Clin. Res.*, 41, 172A (1993)). Additionally, it has been reported that adenosine can decrease the rate of HIV replication in a T-cell line (S. Sipka et al., *Acta. Biochim. Biopys. Hung.*, 23, 75 (1988)). However, there is no evidence that in vivo adenosine has anti-inflammatory activity (G. S. Firestein et al., *Clin. Res.*, 41, 170A (1993); and B. N. Cronstein et al., *Clin. Res.*, 41, 244A (1993)).

It has been suggested that there is more than one subtype of adenosine receptor on neutrophils that can have opposite effects on superoxide release (B. N. Cronstein et al., *J. Clin. Invest.* 85, 1150 (1990)). The existence of $A_{2A}$ receptor on neutrophils was originally demonstrated by Van Calker et al. (D. Van Calker et al., *Eur. J. Pharmacology*, 206, 285 (1991)).

There is one report of the combination of relatively nonspecific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (M. A. Iannone et al., *Topics* and *Perspectives* in *Adenosine Research*, E. Garlach et al., eds., Springer-Verlag, Berlin, pp. 286-298 (1987)). However, R-PIA and Cl-Ado analogs are actually more potent activators of $A_1$ adenosine receptors than of $A_{2A}$ adenosine receptors and, thus, are likely to cause side effects due to activation of $A_1$ receptors on cardiac muscle and other tissues causing effects such as "heart block."

There remains a need for compounds and methods for treating an inflammatory response caused by autoimmune stimulation, particularly caused by arthritis.

SUMMARY OF THE INVENTION

The present invention provides a therapeutic method for treating an inflammatory response caused by autoimmune stimulation, comprising the administration to a patient in need thereof, an effective antiinflammatory amount amount of an $A_{2A}$ adenosine receptor agonist. The invention further comprises treating the patient with an $A_{2A}$ adenosine receptor agonist, optionally, in combination with a Type IV phosphodiesterase (PDE) inhibitor. In one embodiment, the autoimmune stimulation is caused by arthritis such as, for example, rheumatoid arthritis.

The agonists of $A_{2A}$ adenosine receptors of the invention can inhibit neutrophil, macrophage and T cell activation and thereby reduce inflammation caused autoimmune responses. The effects of adenosine $A_{2A}$ agonists can be enhanced by type IV phosphodiesterase inhibitors such as rolipram.

The invention also provides compounds of the invention for use in medical therapy (e.g., for use as an adjunct in the treatment of an inflammatory response, caused by an autoimmune stimulation where the autoimmune stimulation is caused by arthritis) including autoimmune stimulation caused by rheumatoid arthritis, with $A_{2A}$ adenosine receptor agonists, as well as the use of a compound of the invention for the manufacture of a medicament for reducing inflammation caused by arthritis.

In another aspect, the present invention also provides a method to treat an inflammatory response caused by an the autoimmune stimulation is caused by arthritis such as, for example, rheumatoid arthritis including administering to a mammal in need of said therapy, an effective anti-inflammatory amount of an agonists of $A_{2A}$ adenosine receptor, optionally with a PDE-IV inhibitor, such as, rolipram.

The invention provides a compound of the invention, e.g., formula I for use in medical therapy, preferably for use in treating inflammation or protecting mammalian tissue from inflammation such as an inflammatory response, e.g., resulting from allergy, trauma or ischemia/reperfusion injury, as well as the use of a compound of the invention, e.g., formula I for the manufacture of a medicament for the treatment of an inflammatory response due to a pathological condition or symptom in a mammal, such as a human, which is associated with inflammation.

The invention also includes the use of a combination of compounds having $A_{2A}$ adenosine receptor agonist activity with type IV phosphodiesterase inhibitors to preferably cause synergistic decreases in the inflammatory response mediated by leukocytes.

The invention also provides a pharmaceutical composition comprising an effective amount of the compound of the invention, e.g., formula I, or a pharmaceutically acceptable salt thereof, in combination with a pharmaceutically acceptable diluent or carrier, and optionally, in combination with a Type IV phosphodiesterase (PDE) inhibitor. Preferably, the composition is presented as a unit dosage form.

Additionally, the invention provides a therapeutic method for preventing or treating a pathological condition or symptom in a mammal, such as a human, wherein the activity of $A_{2A}$ adenosine receptors is implicated and agonism of said receptors is desired, comprising administering to a mammal in need of such therapy, an effective amount of a compound of the invention, e.g., formula I, or a pharmaceutically acceptable salt thereof. It is believed that activation of $A_{2A}$ adenosine receptors inhibits inflammation by affecting neutrophils, mast cells, monocytes/macrophages, platelets T-cells and/or eosinophils. Inhibition of these inflammatory cells results in tissue protection following tissue insults.

Among the inflammatory responses that can be treated (including treated prophylactically) with a compound of the invention, e.g., formula I, optionally with a Type IV PDE inhibitor, are inflammation due to:

(a) autoimmune stimulation (autoimmune diseases), such as lupus erythematosus, multiple sclerosis, infertility from endometriosis, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, poison ivy, vernal conjunctivitis and other eosinophil-mediated conditions;

(c) skin diseases such as psoriasis, contact dermatitis, eczema, infectious skin ulcers, open wounds, cellulitis;

(d) infectious diseases including sepsis, septic shock, encephalitis, infectious arthritis, endotoxic shock, gram negative shock, Jarisch-Herxheimer reaction, anthrax, plague, tularemia, ebola, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity);

(e) wasting diseases: cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, contrast dyes, antibiotics, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exasperated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) gout; and (k) chemical or thermal trauma due to burns, acid, alkali and the like.

Unexpectedly, it was found that administration of one or more compounds of the invention, e.g., formula (I) was effective after the onset of the inflammatory response, e.g., after the subject was afflicted with the pathology or trauma that initiates the inflammatory response.

DETAILED DESCRIPTION OF THE INVENTION

Figure 1:
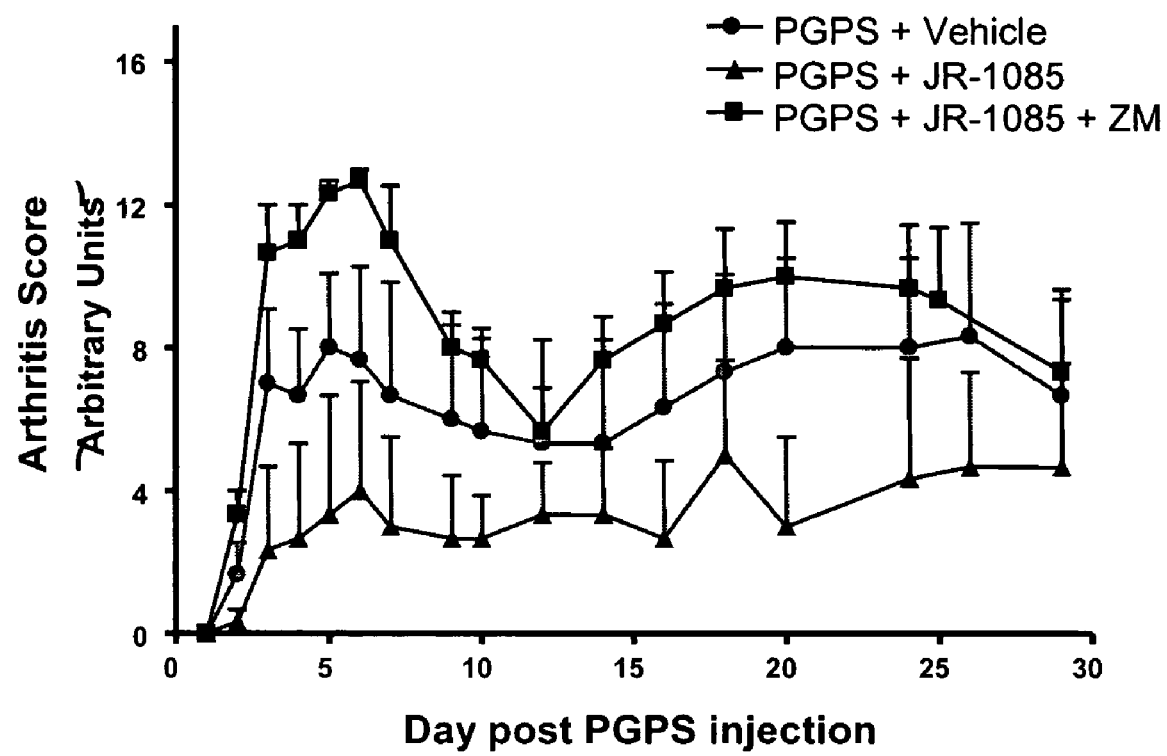
FIG. 1 illustrates the effects of JR-1085 vs JR-1085/ZM in PGPS-induced (SCW) arthritis.
Figure 2:
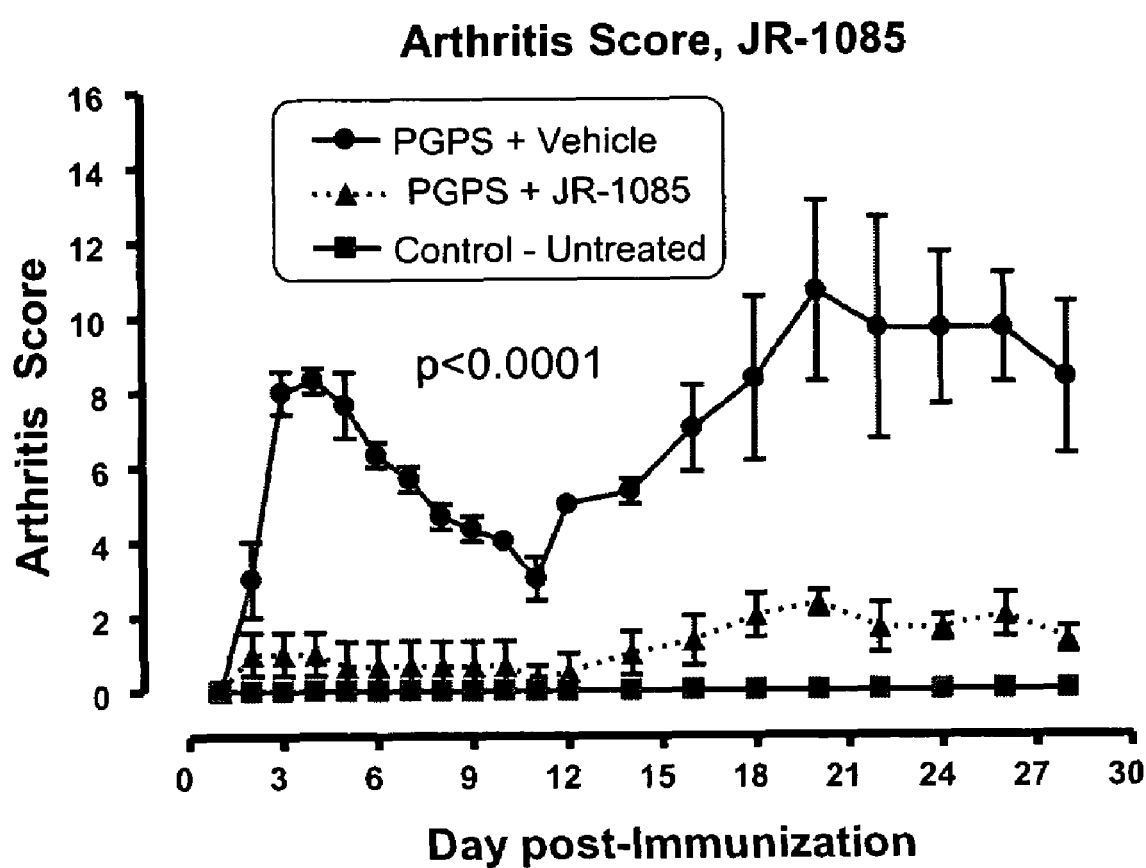
FIG. 2 illustrates the effects of JR-1085 in PGPS-induced (SCW) arthritis.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that the compounds of formulas (I), (II), (III), and (IV) have more than one chiral center and may be isolated in optically active and racemic forms. Preferably, the riboside moiety of the compounds is derived from D-ribose, i.e., the 3',4'-hydroxyl groups are alpha to the sugar ring and the 2' and 5' groups is beta (3R, 4S, 2R, 5S). When the two groups on the cyclohexyl group are in the 1- and 4-position, they are preferably trans. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically-active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_1-C_8)$alkyl can be methyl, ethyl, propyl, isopropyl, butyl, iso-butyl, sec-butyl, pentyl, 3-pentyl, hexyl, heptyl or octyl. As used herein, the term "cycloalkyl" encompasses bicycloalkyl (norbornyl, 2.2.2-bicyclooctyl, etc.) and tricycloalkyl (adamantyl, etc.), optionally comprising 1-2 N, O or S. Cycloalkyl also encompasses (cycloalkyl)

alkyl. Thus, $(C_3-C_6)$cycloalkyl can be cyclopropyl, cyclobutyl, cyclopentyl, cyclohexyl and the like. $(C_1-C_8)$alkoxy can be methoxy, ethoxy, propoxy, isopropoxy, butoxy, iso-butoxy, sec-butoxy, pentoxy, 3-pentoxy, or hexyloxy; $(C_2-C_6)$ alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl ($CO_2R^2$) can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, puridyl (or its N-oxide), thienyl, pyrimidinyl (or its N-oxide), indolyl, isoquinolyl (or its N-oxide) or quinolyl (or its N-oxide).

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(Y) wherein Y is absent or is H, O, $(C_1-C_8)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "heterocycle" generally represents a non aromatic heterocyclic group, having from 3 to about 10 ring atoms, which can be saturated or partially unsaturated, containing at least one heteroatom (e.g., 1, 2, or 3) selected from the group consisting of oxygen, nitrogen, and sulfur. Specific, "heterocycle" groups include monocyclic, bicyclic, or tricyclic groups containing one or more heteroatoms selected from the group consisting of oxygen, nitrogen, and sulfur. A "heterocycle" group also can include one or more oxo groups (=O) attached to a ring atom. Non-limiting examples of heterocycle groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g. ethylene —$CH_2CH_2$—).

The term "aryl$(C_1-C_8)$alkylene" for example includes benzyl, phenethyl, 3-phenylpropyl, naphthylmethyl and the like.

As used herein the term "in conjunction with" refers to co-administration of an anti-rejection agent with the $A_{2A}$ adenosine receptor agonist. The co-administration of an agent and an $A_{2A}$ adenosine receptor agonists includes administration of the agent and agonist either simultaneously, as a mixture, or sequentially. The sequential administration of the $A_{2A}$ adenosine receptor agonists can be prior to administration of the agent, within minutes or up to about 48 hours either before the administration of the agent. The $A_{2A}$ adenosine receptor agonists can also be administered after the agent. Preferably the administration of the $A_{2A}$ adenosine receptor agonists will be within about 24 hours and more preferably within about 12 hours.

In one embodiment, the patient is administered the $A_{2A}$ adenosine receptor agonists prior to transplantation. In another embodiment, the patient is implanted with a pump containing the $A_{2A}$ adenosine receptor agonists prior to transplantation.

The carbon atom content of various hydrocarbon-containing moieties is indicated by a prefix designating the minimum and maximum number of carbon atoms in the moiety, i.e., the prefix $C_i-C_j$ indicates a moiety of the integer "i" to the integer "j" carbon atoms, inclusive. Thus, for example, $(C_1-C_8)$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

In one embodiment, agonists of $A_{2A}$ adenosine receptors that are useful in the practice of the present invention include compounds having the formula (I):

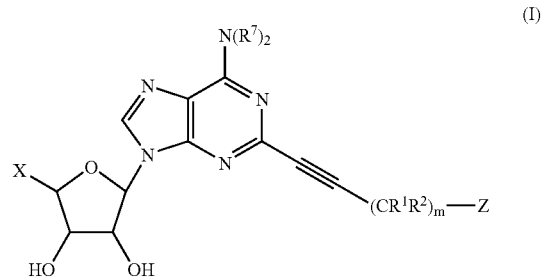

wherein

Z is $CR^3R^4R^5$ or $NR^4R^5$; each $R^1$ is independently hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocycle, heterocycle$(C_1-C_8)$alkylene-, aryl, aryl$(C_1-C_8)$ alkylene-, heteroaryl, heteroaryl$(C_1-C_8)$alkylene-, —$CO_2R^a$, $R^aC(=O)O$—, $R^aC(=O)$—, —$OCO_2R^a$, $R^bR^cNC(=O)O$—, $R^aOC(=O)N(R^b)$—, $R^bR^cN$—, $R^bR^cNC(=O)$—, $R^aC(=O)N(R^b)$—, $R^bR^cNC(=O)N$ $(R^b)$—, $R^bR^cNC(=S)N(R^b)$—, —$OPO_3R^a$, $R^aOC(=S)$—, $R^aC(=S)$—, —$SSR^a$, $R^aS(=O)$—, $R^aS(=O)_2$—, or —N=$NR^b$;

each $R^2$ is independently hydrogen, halo, $(C_1-C_8)$alkyl, $(C_3-C_8)$cycloalkyl, heterocycle, heterocycle$(C_1-C_8)$alkylene-, aryl, aryl$(C_1-C_8)$alkylene-, heteroaryl, or heteroaryl $(C_1-C_8)$alkylene-; or $R^1$ and $R^2$ and the atom to which they are attached is C=O, C=S or C=$NR^a$, $R^4$ and $R^5$ together with the atoms to which they are attached form a saturated or partially unsaturated, mono-, bicyclic- or aromatic ring having 3, 4, 5, 6, 7, 8, 9 or 10 ring atoms optionally comprising 1, 2, 3, or 4 heteroatoms selected from non-peroxide oxy (—O—), thio (—S—), sulfinyl (—SO—), sulfonyl (—S(O)$_2$—) or amine (—NR$^b$—) in the ring;

wherein any ring comprising R$^4$ and R$^5$ is substituted with from 1 to 14 R$^6$ groups; wherein each R$^6$ is independently hydrogen, halo, —OR$^a$, —SR$^a$, (C$_1$-C$_8$)alkyl, cyano, nitro, trifluoromethyl, trifluoromethoxy, (C$_1$-C$_8$)cycloalkyl, (C$_6$-C$_{12}$)bicycloalkyl, heterocycle or heterocycle (C$_1$-C$_8$)alkylene-, aryl, aryl (C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)—, —NNR$^b$, or two R$^6$ groups and the atom to which they are attached is C=O, C=S or; two R$^6$ groups together with the atom or atoms to which they are attached can form a carbocyclic or heterocyclic ring;

R$^3$ is hydrogen, halo, —OR$^a$, —SR$^a$, (C$_1$-C$_8$)alkyl, cyano, nitro, trifluoromethyl, trifluoromethoxy, (C$_3$-C$_8$)cycloalkyl, heterocycle, heterocycle(C$_1$-C$_8$)alkylene-, aryl, aryl(C$_1$-C$_8$)alkylene-, heteroaryl, heteroaryl(C$_1$-C$_8$)alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)—, R$^a$S(=O)$_2$—, —NNR$^b$; or if the ring formed from CR$^4$R$^5$ is aryl or heteroaryl or partially unsaturated then R$^3$ can be absent;

each R$^7$ is independently hydrogen, (C$_1$-C$_8$)alkyl, (C$_3$-C$_8$)cycloalkyl, aryl or aryl(C$_1$-C$_8$)alkylene, heteroaryl, heteroaryl(C$_1$-C$_8$)alkylene-;

X is —CH$_2$OR$^a$, —CO$_2$R$^a$, —CH$_2$OC(O)R$^a$, —C(O)NR$^b$R$^c$, —CH$_2$SR$^a$, —C(S)OR$^a$, —CH$_2$OC(S)R$^a$, —C(S)NR$^b$R$^c$, or —CH$_2$N(R$^b$)(R$^c$);

wherein any of the alkyl, cycloalkyl, heterocycle, aryl, or heteroaryl, groups of R$^1$, R$^2$, R$^3$, R$^6$ and R$^7$ is optionally substituted on carbon with one or more (e.g. 1, 2, 3, or 4) substituents selected from the group consisting of halo, —OR$^a$, —SR$^a$, (C$_1$-C$_8$)alkyl, cyano, nitro, trifluoromethyl, trifluoromethoxy, (C$_3$-C$_8$)cycloalkyl, (C$_6$-C$_{12}$)bicycloalkyl, heterocycle or heterocycle(C$_1$-C$_8$)-alkylene-, aryl, aryloxy, aryl(C$_1$-C$_8$)alkylene-, heteroaryl, heteroaryl(C$_1$-C$_8$-alkylene-, —CO$_2$R$^a$, R$^a$C(=O)O—, R$^a$C(=O)—, —OCO$_2$R$^a$, R$^b$R$^c$NC(=O)O—, R$^a$OC(=O)N(R$^b$)—, R$^b$R$^c$N—, R$^b$R$^c$NC(=O)—, R$^a$C(=O)N(R$^b$)—, R$^b$R$^c$NC(=O)N(R$^b$)—, R$^b$R$^c$NC(=S)N(R$^b$)—, —OPO$_3$R$^a$, R$^a$OC(=S)—, R$^a$C(=S)—, —SSR$^a$, R$^a$S(=O)$_p$—, R$^b$R$^c$NS(O)$_p$—, and —N=NR$^b$;

wherein any (C$_1$-C$_8$)alkyl, (C$_3$-C$_8$)cycloalkyl, (C$_6$-C$_{12}$)bicycloalkyl, (C$_1$-C$_8$)alkoxy, (C$_1$-C$_8$)alkanoyl, (C$_1$-C$_8$)alkylene, or heterocycle, is optionally partially unsaturated;

each R$^a$, R$^b$ and R$^c$ is independently hydrogen, (C$_1$-C$_8$) alkyl, or (C$_1$-C$_8$)alkyl substituted with 1-3 (C$_1$-C$_8$)alkoxy, (C$_3$-C$_8$)cycloalkyl, (C$_1$-C$_8$)alkylthio, amino acid, aryl, aryl (C$_1$-C$_8$)alkylene, heteroaryl, or heteroaryl(C$_1$-C$_8$)alkylene; or R$^b$ and R$^c$, together with the nitrogen to which they are attached, form a pyrrolidino, piperidino, morpholino, or thiomorpholino ring; and R$^d$ is hydrogen or (C$_1$-C$_6$)alkyl; m is 0 to about 8 and p is 0 to 2; provided that m is at least 1 when Z is NR$^4$R$^5$; or a pharmaceutically acceptable salt thereof.

Specific and preferred values listed below for radicals, substituents, and ranges, are for illustration only; they do not exclude other defined values or other values within defined ranges for the radicals and substituents.

A specific autoimmune response is an inflammatory response from arthritis.

A specific arthritis is rheumatoid arthritis.

A specific value for R$^1$ is hydrogen, —OH, —CH$_2$OH, —OMe, —OAc, —NH$_2$, —NHMe, —NMe$_2$ or —NHAc.

Another specific value for R$^1$ is hydrogen, —OH, —OMe, —OAc, —NH$_2$, —NHMe, —NMe$_2$ or —NHAc.

Another specific value for R$^1$ is hydrogen, —OH, —OMe, or —NH$_2$.

Another specific value for R$^1$ is hydrogen, —OH, or —NH$_2$.

A more specific value for R$^1$ is hydrogen or —OH.

A specific value for R$^1$, R$^2$ and the carbon atom to which they are attached is carbonyl (C=O).

A specific value for R$^2$ is hydrogen or (C$_1$-C$_8$)alkyl, cyclopropyl, cyclohexyl or benzyl.

Another specific value for R$^2$ is hydrogen, methyl, ethyl or propyl.

Another specific value for R$^2$ is hydrogen or methyl.

A more specific value for R$^2$ is hydrogen

A specific value for R$^3$ is hydrogen, OH, OMe, OAc, NH$_2$, NHMe, NMe$_2$ or NHAc.

Another specific value for R$^3$ is hydrogen, OH, OMe, or NH$_2$.

Another specific value for R$^3$ is hydrogen, OH, or NH$_2$.

A more specific value for R$^3$ is hydrogen or OH.

A specific value for the ring comprising R$^4$, R$^5$ and the atom to which they are connected is cyclopentane, cyclohexane, piperidine, dihydro-pyridine, tetrahydro-pyridine, pyridine, piperazine, decaline, tetrahydro-pyrazine, dihydropyrazine, pyrazine, dihydro-pyrimidine, tetrahydro-pyrimidine, hexahydro-pyrimidine, pyrazine, imidazole, dihydroimidazole, imidazolidine, pyrazole, dihydro-pyrazole, and pyrazolidine.

A more specific value for the ring comprising R$^4$ and R$^5$ and the atom to which they are connected is, cyclohexane, piperidine or piperazine.

A specific value for R$^6$ is hydrogen, (C$_1$-C$_8$)alkyl, or substituted (C$_1$-C$_8$)alkyl, —OR$^a$, —CO$_2$R$^a$, R$^a$C(=O)—, R$^a$C(=O)O—, R$^b$R$^c$N—, R$^b$R$^c$NC(=O)—, or aryl.

Another specific value for R$^6$ is hydrogen, (C$_1$-C$_8$)alkyl, —OR$^a$, —CO$_2$R$^a$, R$^a$C(=O)—, R$^a$C(=O)O—, R$^b$R$^c$N—, R$^b$R$^c$NC(=O)—, or aryl.

Another specific value for R$^6$ is hydrogen, methyl, ethyl, butyl, OH, OR$^a$, —CO$_2$R$^a$, R$^a$C(=O)—, OC(=O)CH$_2$CH$_3$, —CONR$^b$R$^c$, —NR$^b$R$^c$ or phenyl.

Another specific value for R$^6$ is hydrogen, OH, OMe, methyl, ethyl, t-butyl, —CO$_2$R$^a$, —C(=O)NR$^b$R$^c$, —OAc, —NH$_2$, —NHMe, —NMe$_2$, —NHEt or —N(Et)$_2$.

Another specific value for R$^6$ is hydrogen, —(CH$_2$)$_{1-2}$OR$^a$, —(CH$_2$)$_{1-2}$C(=O)OR$^a$, —(CH$_2$)$_{1-2}$OC(=O)R$^a$, —(CH$_2$)$_{1-2}$C(=O)R$^a$, —(CH$_2$)$_{1-2}$OCO$_2$R$^a$, —(CH$_2$)$_{1-2}$NHR$^a$, —(CH$_2$)$_{1-2}$NR$^b$R$^c$, —(CH$_2$)$_{1-2}$OC(=O)NHR$^a$, or —(CH$_2$)$_{1-2}$OC(=O)NR$^b$R$^c$.

Another specific value for R$^6$ is hydrogen, —CH$_2$OH, —CH$_2$OAc, —CH$_2$OCH$_3$, —CH$_2$C(=O)OCH$_3$, —CH$_2$OC(=O)CH$_3$, —CH$_2$C(=O)CH$_3$, —CH$_2$OCO$_2$CH$_3$, —CH$_2$NH(CH$_3$), or —(CH$_2$)$_{1-2}$N(CH$_3$)$_2$.

Another specific value for R$^6$ is hydrogen, methyl, ethyl, t-butyl, phenyl, —CO$_2$R$^a$, —CONR$^b$R$^c$, or R$^a$C(=O)—.

Another specific value for R$^6$ is hydrogen, —CH$_2$OH, —CH$_2$OAc, —C(=O)OCH$_3$, —C(=O)CH$_3$, OCO$_2$CH$_3$—OCO$_2$CH$_3$, —CH$_2$NH(CH$_3$), or —(CH$_2$)$_{1-2}$N(CH$_3$)$_2$.

A more specific value for R$^6$ is hydrogen, methyl, ethyl, —CO$_2$R$^a$ —CONR$^b$R$^c$, or R$^a$C(=O)—.

A specific number of R$^6$ groups substituted on the R$^4$R$^5$ ring is from 1 to about 4.

Specific values for $R^a$ are hydrogen, $(C_3$-$C_4)$-cycloalkyl, $(C_1$-$C_4)$alkyl, aryl or aryl$(C_1$-$C_8)$alkylene.

More specific values for $R^a$ are hydrogen, methyl, ethyl, cyclopropyl, cyclobutyl, phenyl or benzyl.

A more specific value for $R^a$ is $(C_1$-$C_8)$alkyl.

Another specific value for $R^a$ is methyl, ethyl, propyl or butyl.

A more specific value for $R^a$ is methyl, ethyl, i-propyl, i-butyl or tert-butyl.

Specific values for $R^b$ and $R^c$ are independently hydrogen, $(C_3$-$C_4)$-cycloalkyl, $(C_1$-$C_4)$alkyl, aryl or aryl$(C_1$-$C_8)$alkylene.

More specific values for $R^b$ and $R^c$ are independently hydrogen, methyl, ethyl, cyclopropyl, cyclobutyl, phenyl or benzyl.

A more specific value for $R^c$ is hydrogen.

More specific values for $R^b$ are hydrogen, methyl, ethyl, cyclopropyl, cyclobutyl, phenyl or benzyl.

More specific values for $R^a$ are methyl, ethyl, cyclopropyl, i-propyl, i-butyl or tert-butyl.

More specific values for $R^a$ are methyl, ethyl, or cyclopropyl.

Another specific value for $R^b$ and $R^c$ is ring.

A specific value for $R^7$ is hydrogen, alkyl, aryl or aryl$(C_1$-$C_8)$alkylene.

Another specific value for $R^7$ is hydrogen, methyl, ethyl, 3-pentyl, phenylCH$_2$CH$_2$—, (phenyl)$_2$CHCH$_2$—, pyridylCH$_2$—, benzyl, or

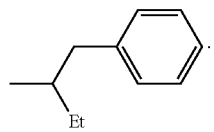

Another specific value for $R^7$ is hydrogen, 3-pentyl, pyridylmethyl, or benzyl.

A specific value for —N$(R^7)_2$ is amino, methylamino, dimethylamino, ethylamino, diethylamino, pentylamino, diphenylethylamino, benzylamino, or

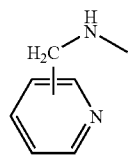

(pyridylmethylamino).

A specific pyridylmethylamino Group is

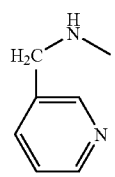

Another specific value for $R^7$ is hydrogen, 3-pentyl, pyridyl-CH$_2$—, or benzyl.

Another specific value for $R^7$ is hydrogen, methyl or ethyl, phenyl or benzyl.

Another specific value for $R^7$ is H, or methyl.

Another specific value for $R^7$ is H.

A specific value for —N$(R^7)_2$ is amino, methylamino, dimethylamino, ethylamino, pentylamino, diphenylethylamino, pyridylmethylamino, diethylamino or benzylamino.

A specific value for —N$(R^7)_2$ is amino, methylamino, dimethylamino, ethylamino, diethylamino diphenylethylamino, pentylamino or benzylamino.

A specific value for N$(R^7)_2$ is amino, or methylamino.

A specific value for X is —CH$_2$OR$^a$, —CO$_2$R$^a$, —CH$_2$OC(O)R$^a$, —C(O)NR$^b$R$^c$.

Another specific value for X is —CH$_2$OR$^a$ or —C(O)NR$^b$R$^c$.

A more specific value for X is —CH$_2$OH,

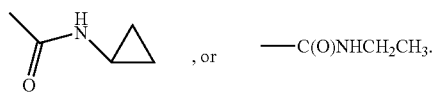

A specific value for m is 0, 1, or 2.

A more specific value for m is 0, or 1.

Specific examples of rings comprising $R^4$, $R^5$ and the atom to which they are connected include:

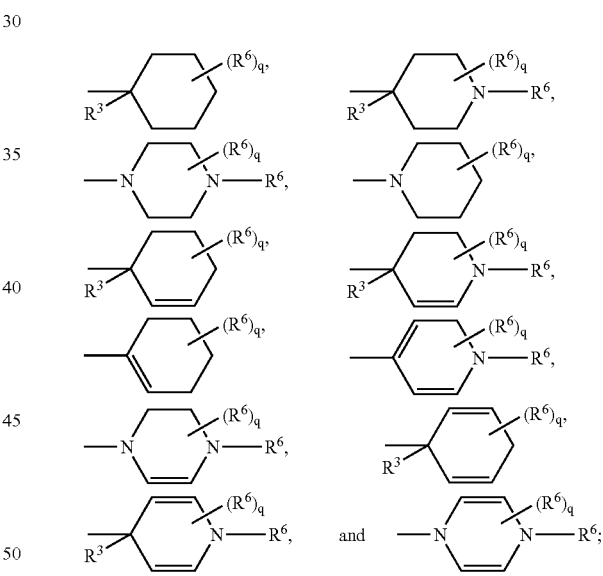

where q is from 0 to 14.

More specific examples of rings comprising $R^4$, $R^5$ and the atom to which they are connected include:

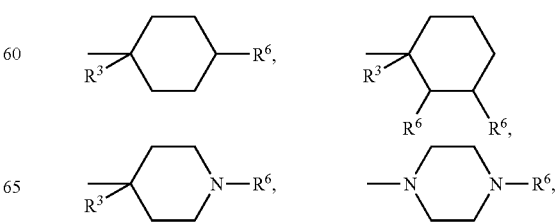

-continued

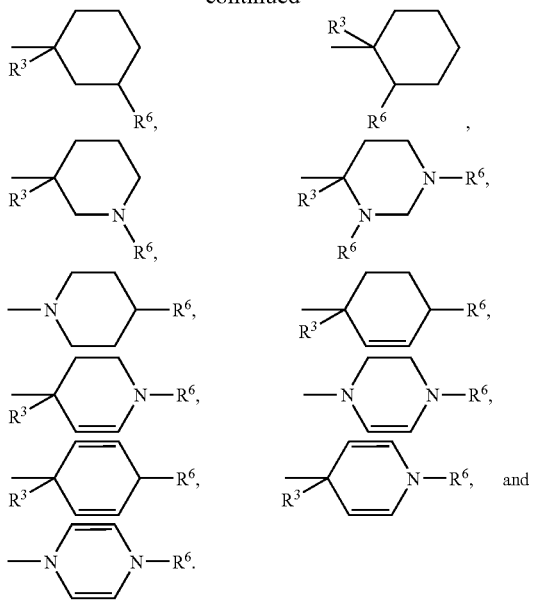

Specific values for the ring comprising R⁴, R⁵ and the atom to which they are connected are 2-methyl cyclohexane, 2,2-dimethylcyclohexane, 2-phenylcyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane. 4-cyclohexanecarboxylic acid, 4-cyclohexanecarboxylic acid esters, or 4-methyloxyalkanoyl-cyclohexane.

More specific values for the ring comprising R⁴, R⁵ and the atom to which they are connected are 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 1-piperidine, 1-piperidine-4-carboxylic acid methyl ester, 1-piperidine-4-carboxylic acid ethyl ester, 1-piperidine-4-carboxylic acid propyl ester, 1-piperidine-4-carboxylic acid tert-butyl ester, 1-piperidine-4-carboxylic acid methyl ester, 3-piperidine, 3-piperidene-1-carboxylic acid, 3-piperidine-1-carboxylic acid methyl ester, 3-piperidine-1-carboxylic acid tert-butyl ester, 1,4-piperazine, 4-piperazine-1-carboxylic acid, 4-piperazine-1-carboxylic acid methyl ester, 4-piperazine-1-carboxylic acid ethyl ester, 4-piperazine-1-carboxylic acid propyl ester, 4-piperazine-1-carboxylic acid tert-butylester, 1,3-piperazine, 3-piperazine-1-carboxylic acid, 3-piperazine-1-carboxylic acid methyl ester, 3-piperazine-1-carboxylic acid ethyl ester, 3-piperazine-1-carboxylic acid propyl ester, 3-piperidine-1-carboxylic acid tert-butylester, 1-piperidine-3-carboxylic acid methyl ester, 1-piperidine-3-carboxylic acid ethyl ester, 1-piperidine-3-carboxylic acid propyl ester or 1-piperidine-3-carboxylic acid tert-butyl ester.

Another group of specific values for the ring comprising R⁴ and R⁵ are 2-methyl cyclohexane, 2,2-dimethylcyclohexane, 2-phenyl cyclohexane, 2-ethylcyclohexane, 2,2-diethylcyclohexane, 2-tert-butyl cyclohexane, 3-methyl cyclohexane, 3,3-dimethylcyclohexane, 4-methyl cyclohexane, 4-ethylcyclohexane, 4-phenyl cyclohexane, 4-tert-butyl cyclohexane, 4-carboxymethyl cyclohexane, 4-carboxyethyl cyclohexane, 3,3,5,5-tetramethyl cyclohexane, 2,4-dimethyl cyclopentane, 4-piperidine-1-carboxylic acid methyl ester, 4-piperidine-1-carboxylic acid tert-butyl ester 4-piperidine, 4-piperazine-1-carboxylic acid methyl ester, 4-piperidine-1-carboxylic acid tert-butylester, 1-piperidine-4-carboxylic acid methyl ester, 1-piperidine-4-carboxylic acid tert-butyl ester, tert-butylester, 1-piperidine-4-carboxylic acid methyl ester, or 1-piperidine-4-carboxylic acid tert-butyl ester, 3-piperidine-1-carboxylic acid methyl ester, 3-piperidine-1-carboxylic acid tert-butyl ester, 3-piperidine, 3-piperazine-1-carboxylic acid methyl ester, 3-piperidine-1-carboxylic acid tert-butylester, 1-piperidine-3-carboxylic acid methyl ester, 1-piperidine-3-carboxylic acid tert-butyl ester Specific compounds of formula (I) are those wherein each R⁷ is H, X is ethylaminocarbonyl and R¹ is hydroxy, R² is hydrogen, and Z is 4-carboxy-cyclohexyl, wherein Rᵃ is hydrogen, 4; Z is 4-methoxycarbonylcyclohexyl-methyl, Rᵃ is methyl, 5; R¹ and R² together are oxo, Z is a 4-carbonylcyclohexyl group, wherein Rᵃ is methyl, methoxy, ethyl, ethoxy, propyl, isopropoxy, -isobutyl, tert-butyl, amine, methylamine or dimethylamine, 6.

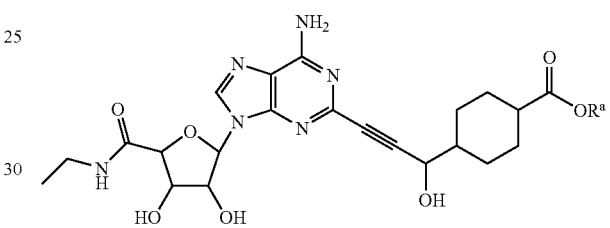

4, Rᵃ is H
5, Rᵃ is CH₃

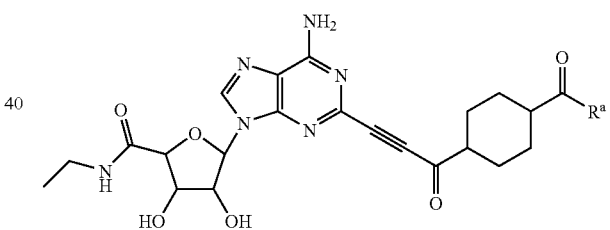

6

Another group of specific compounds of formula (I) are those wherein each R is H, X is ethylaminocarbonyl, R¹ is hydroxy, R² is hydrogen, and Z is a substituted 4-(methyleneoxycarbonyl)cyclohexyl group, wherein Rᵃ is methyl, ethyl, propyl, tert-butyl, methoxy, ethoxy, methylamine or dimethylamine, 7; or R¹ and R² together are oxo, and Z is a substituted -(methyleneoxycarbonyl)-cyclohexyl group, wherein Rᵃ is methyl, ethyl, propyl, tert-butyl, methoxy, ethoxy, methylamine or dimethylamine, 8.

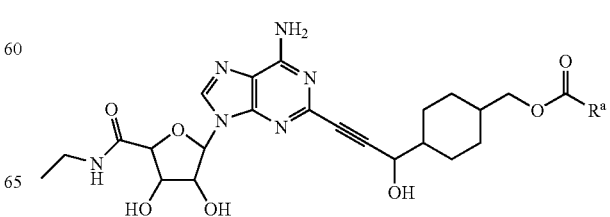

7

8

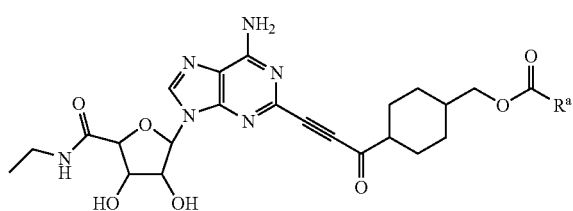

Another group of specific compounds of formula (I) are those wherein each $R^7$ is H, X is ethylaminocarbonyl, and $R^1$ and $R^2$ are each hydrogen, and Z is a 1-piperidyl-4-carboxylic acid or ester group, wherein $R^a$ is hydrogen, methyl, ethyl, propyl, isopropyl, or t-butyl, 9; $R^1$ and $R^2$ together are oxo, and Z is a 1-piperidyl-4-carboxylic acid or ester group, wherein $R^a$ is hydrogen, methyl, ethyl, propyl, isopropyl, or t-butyl, 10; $R^1$ and $R^2$ are each hydrogen and Z is a 4-(methyleneoxycarbonyl)piperidin-4-yl group wherein $R^a$ is methyl, ethyl, propyl or t-butyl, amine, methylamine, dimethylamine, 11; or $R^1$ and $R^2$ together are oxo, and Z is a 4-(methyleneoxycarbonyl)piperidin-4-yl wherein $R^a$ is methyl, ethyl, propyl or t-butyl, amine, methylamine, dimethylamine, 12; $R^1$ and $R^2$ are each hydrogen and Z is a 4-(methyleneoxycarbonyl)piperidin-4-yl-oxy wherein $R^a$ is hydrogen, methyl, ethyl, propyl isopropyl, isobutyl, or t-butyl, 13 or $R^1$ and $R^2$ together are oxo, Z is a 4-(methyleneoxycarbonyl)piperidin-4-yl-oxy wherein $R^a$ is hydrogen, methyl, ethyl, propyl, isopropyl, isobutyl, or t-butyl, 14.

9

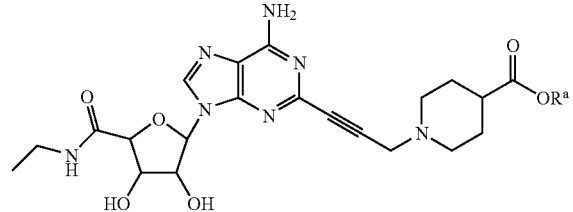

10

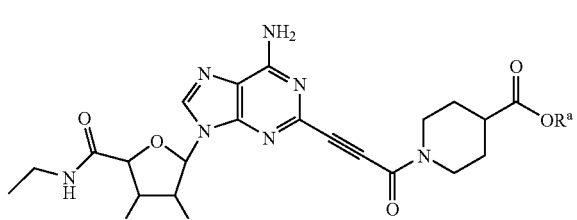

11

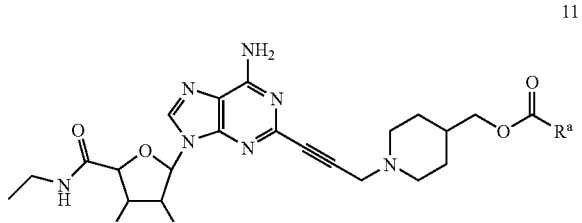

12

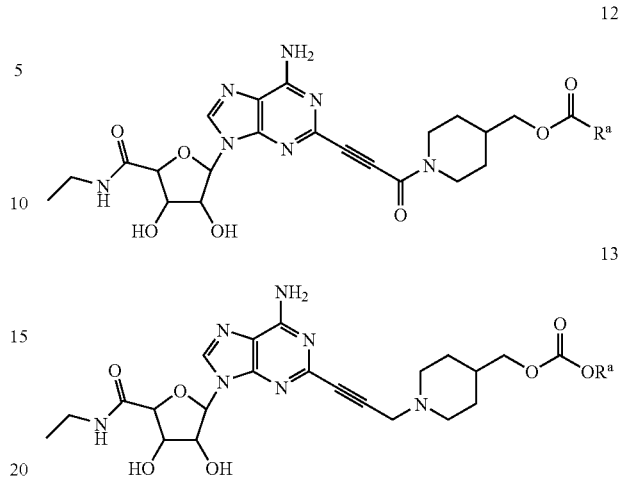

13

Another group of specific compounds of formula (I) are those wherein each $R^7$ is H, X is ethylaminocarbonyl, $R^1$ and $R^2$ are each hydrogen, and Z is a 4-piperidyl-1-carboxylic acid or ester group, wherein $R^a$ is methyl, ethyl, propyl, isopropyl, isobutyl, or t-butyl, 15, $R^1$ is hydroxy, $R^2$ is hydrogen, and Z is a 4-piperidyl-1-carboxylic acid or ester group, wherein $R^a$ is methyl, ethyl, propyl, isopropyl, isobutyl, or t-butyl, 16; or $R^1$ and $R^2$ together are oxo, and Z is a 4-piperidyl-1-carboxylic acid or ester group, wherein $R^a$ is methyl, ethyl, propyl, isopropyl, isobutyl, or t-butyl, 17.

15

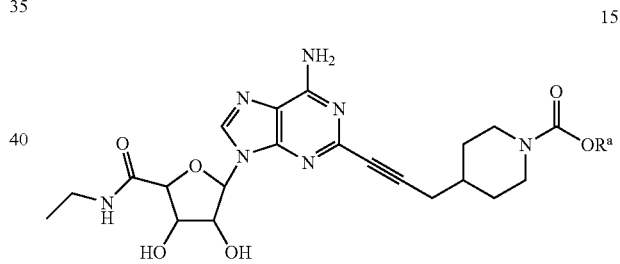

16

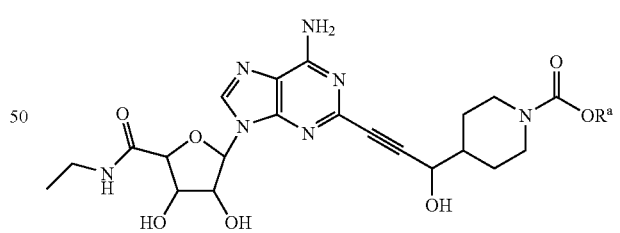

17

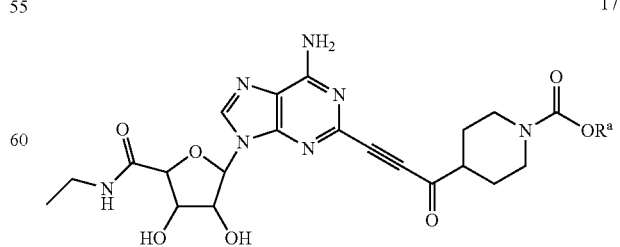

Another group of specific compounds of formula (I) are those wherein each $R^7$ is H, X is ethylaminocarbonyl, $R^1$ and R[2] are each hydrogen, Z is a 4-piperazine-1-carboxylic acid or ester group wherein R[a] is methyl, ethyl, isopropyl, isobutyl, or t-butyl, 18; or R[1] and R[2] together are oxo, Z is a 4-piperazine-1-carboxylic acid or ester group wherein R[a] is methyl, ethyl, isopropyl, isobutyl, or t-butyl, 19.

Specific $A_{2A}$ adenosine receptor agonists suitable for use with the present invention include those described in U.S. Pat. No. 6,232,297 and in U.S. Patent Application No. 2003/0186926 A1.

Specific compounds of the invention include formula (IA)

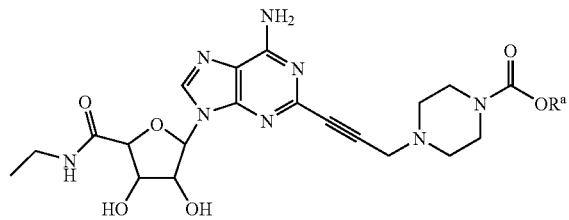

18

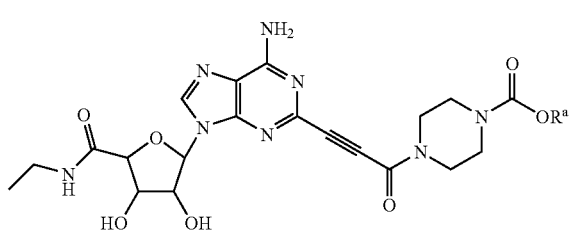

19

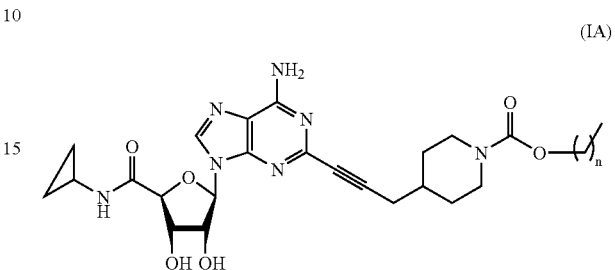

(IA)

In formula (IA) n is 0, 1, 2, 3, 4, 5, 6, 7, 8, 9, 10, 11, 12, 13, 14, 15, 16, 17, or 18. In another group of specific compounds n is, 5, 6, 7, 8, 9, 10, 11, 12, 13, 14, 15, 16, 17, or 18.

Specific compounds of the invention include formula (IB)

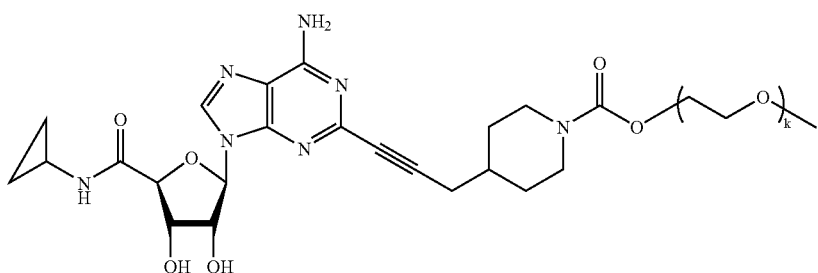

(IB)

In formula (IB) k is 1, 2, 3, 4, 5, 6, 7, 8, 9, 10, 11, 12, 13, 14, 15, 16, 17, or 18.

Specific compounds of the invention include formula (IC)

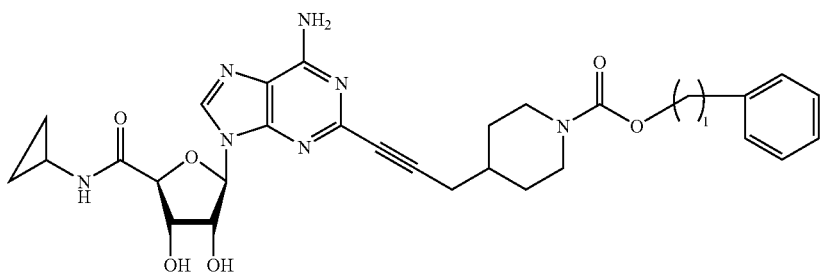

(IC)

In formula (IC) 1 is 0, 1, 2, 3, or 4.
Other specific compounds of the invention include
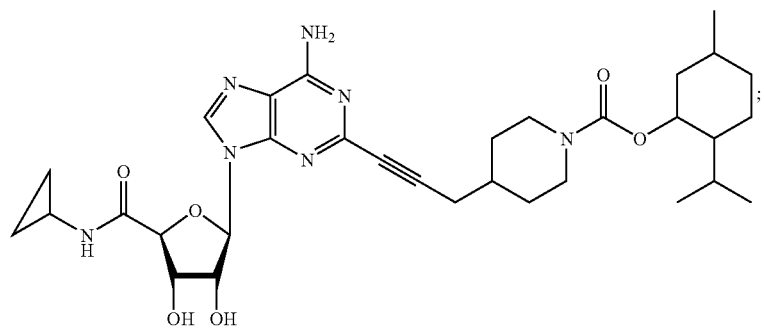
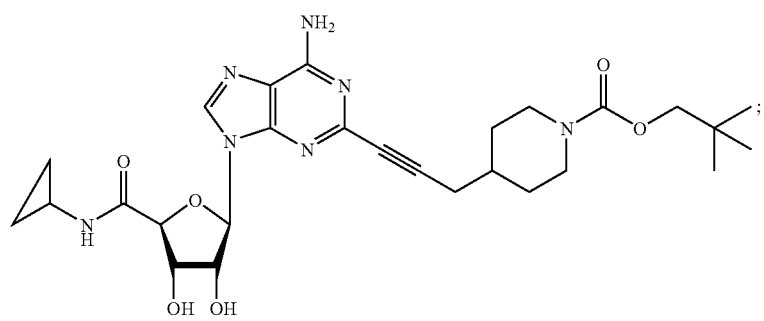
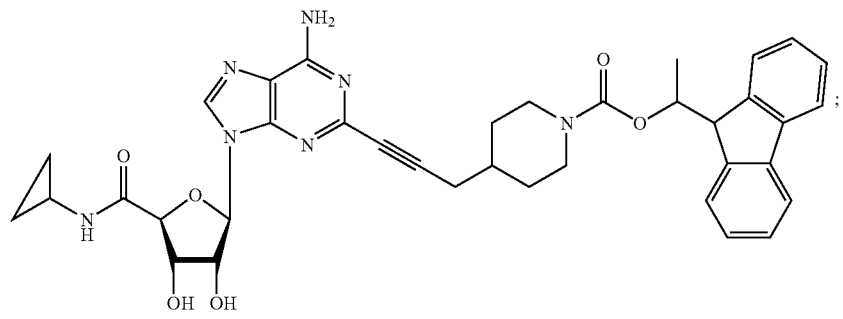
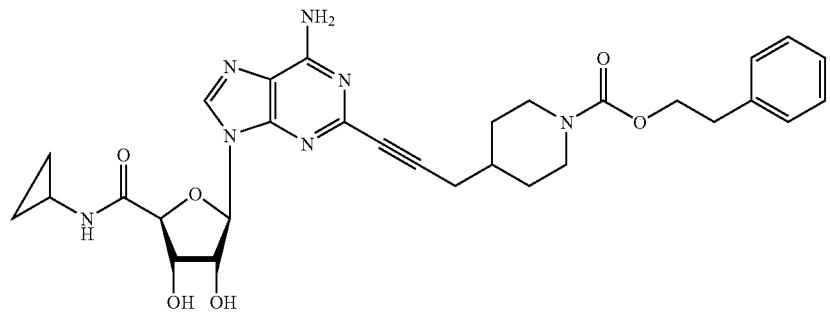

Examples of compounds useful in practicing the invention are illustrated in tables 1, 2, 3, 4, 5, 6 and 7 below:

TABLE 1

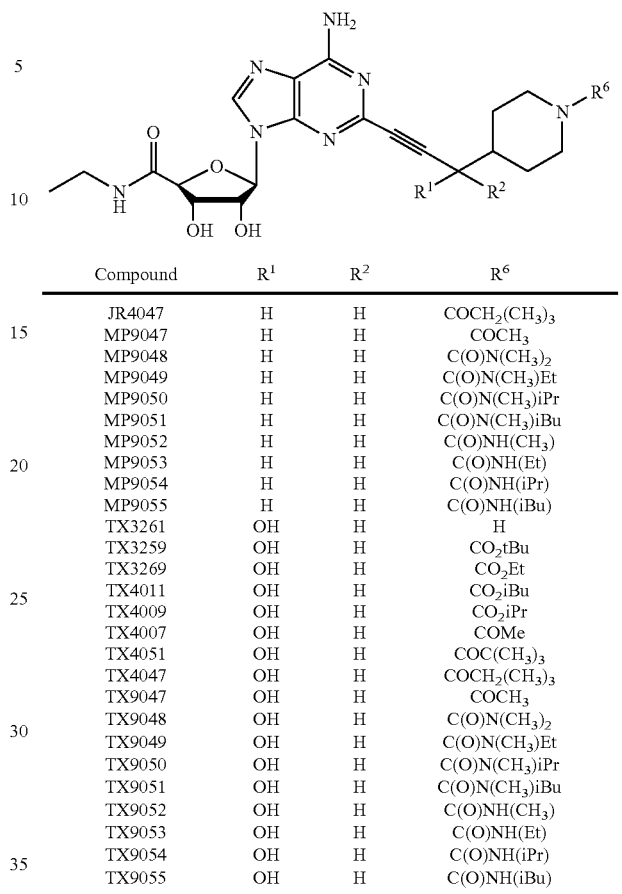

| Compound | R | $R^1$ | $R^2$ | $R^6$ |
|---|---|---|---|---|
| ATL2037 | NECA | H | H | $CH_2OH$ |
| MP9056 | NECA | OH | H | $CH_2OH$ |
| ATL146a | NECA | H | H | $CO_2H$ |
| MP9057 | NECA | OH | H | $CO_2H$ |
| ATL146e | NECA | H | H | $CO_2Me$ |
| MP9058 | NECA | OH | H | $CO_2Me$ |
| JR2145 | $CH_2OH$ | H | H | $CO_2Me$ |
| MP9059 | $CH_2OH$ | OH | H | $CO_2Me$ |
| ATL193 | NECA | H | H | $CH_2OAc$ |
| MP9060 | NECA | OH | H | $CH_2Oac$ |
| JR2147 | $CH_2OH$ | H | H | $CH_2Oac$ |
| MP9061 | $CH_2OH$ | OH | H | $CH_2Oac$ |
| JR3023 | NECA | H | H | $CH_2N(CH_3)_2$ |
| MP9062 | NECA | OH | H | $CH_2N(CH_3)_2$ |
| JR3021 | NECA | H | H | $COOCH_2CH_2NHBoc$ |
| MP9063 | NECA | OH | H | $COOCH_2CH_2NHBoc$ |
| JR3033 | NECA | H | H | $COOCH_2CH_2NH_2$ |
| MP9064 | NECA | OH | H | $COOCH_2CH_2NH_2$ |
| JR3037 | NECA | H | H | $CONHCH_2CH_3$ |
| MP9065 | NECA | OH | H | $CONHCH_2CH_3$ |
| JR3055 | NECA | H | H | $CONH_2$ |
| MP9072 | NECA | OH | H | $CONH_2$ |
| JR3065 | NECA | H | H | CONHMe |
| MP9066 | NECA | OH | H | CONHMe |
| JR3067B | NECA | H | H | Me, cis $CO_2Me$ |
| MP9067 | NECA | OH | H | Me, cis $CO_2Me$ |
| JR3067A | NECA | H | H | Me, trans $CO_2Me$ |
| MP9068 | NECA | OH | H | Me, trans $CO_2Me$ |
| JR3087 | NECA | H | H | $CH_2CH_3$ |
| MP9069 | NECA | OH | H | $CH_2CH_3$ |
| JR3159A | NECA | OH | H | H |
| JR3159B | NECA | OH | H | H |
| JR3119 | NECA | H | H | $COCH_3$ |
| MP9070 | NECA | OH | H | $COCH_3$ |
| JR3121 | NECA | H | H | $CHCH_3(OH)$ |
| MP9071 | NECA | OH | H | $CHCH_3(OH)$ |
| JR3139 | NECA | OH | $C_6H_{11}$ | H |

NECA = $CH_3CH_2N(H)C(O)$—

TABLE 2

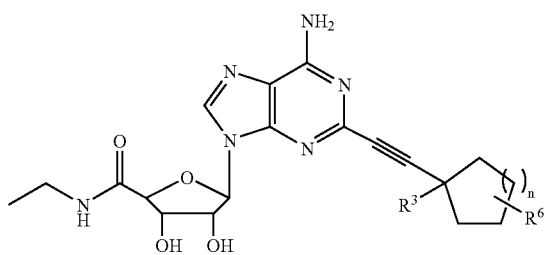

| Compound | $R^1$ | $R^2$ | $R^6$ |
|---|---|---|---|
| JR3261 | H | H | H |
| JR3259 | H | H | $CO_2tBu$ |
| JR3269 | H | H | $CO_2Et$ |
| JR4011 | H | H | $CO_2iBu$ |
| JR4009 | H | H | $CO_2iPr$ |
| JR4007 | H | H | COMe |
| JR4051 | H | H | $COC(CH_3)_3$ |

TABLE 2-continued

| Compound | $R^1$ | $R^2$ | $R^6$ |
|---|---|---|---|
| JR4047 | H | H | $COCH_2(CH_3)_3$ |
| MP9047 | H | H | $COCH_3$ |
| MP9048 | H | H | $C(O)N(CH_3)_2$ |
| MP9049 | H | H | $C(O)N(CH_3)Et$ |
| MP9050 | H | H | $C(O)N(CH_3)iPr$ |
| MP9051 | H | H | $C(O)N(CH_3)iBu$ |
| MP9052 | H | H | $C(O)NH(CH_3)$ |
| MP9053 | H | H | $C(O)NH(Et)$ |
| MP9054 | H | H | $C(O)NH(iPr)$ |
| MP9055 | H | H | $C(O)NH(iBu)$ |
| TX3261 | OH | H | H |
| TX3259 | OH | H | $CO_2tBu$ |
| TX3269 | OH | H | $CO_2Et$ |
| TX4011 | OH | H | $CO_2iBu$ |
| TX4009 | OH | H | $CO_2iPr$ |
| TX4007 | OH | H | COMe |
| TX4051 | OH | H | $COC(CH_3)_3$ |
| TX4047 | OH | H | $COCH_2(CH_3)_3$ |
| TX9047 | OH | H | $COCH_3$ |
| TX9048 | OH | H | $C(O)N(CH_3)_2$ |
| TX9049 | OH | H | $C(O)N(CH_3)Et$ |
| TX9050 | OH | H | $C(O)N(CH_3)iPr$ |
| TX9051 | OH | H | $C(O)N(CH_3)iBu$ |
| TX9052 | OH | H | $C(O)NH(CH_3)$ |
| TX9053 | OH | H | $C(O)NH(Et)$ |
| TX9054 | OH | H | $C(O)NH(iPr)$ |
| TX9055 | OH | H | $C(O)NH(iBu)$ |

TABLE 3

| Compound | n | $R^3$ | $R^6$ |
|---|---|---|---|
| JR3135 | 1 | OH | H |
| JR3089 | 2 | OH | H |
| JR3205 | 2 | $NH_2$ | H |
| JR3177A | 2 | OH | $2\text{-}CH_3$ |
| JR3177B | 2 | OH | $2\text{-}CH_3$ |
| JR3181A | 2 | OH | $2\text{-}CH_3$ |
| JR3181B | 2 | OH | $2\text{-}CH_3$ |
| JR3227 | 2 | OH | $2\text{-}C(CH_3)_3$ |
| JR9876 | 2 | OH | $2\text{-}C_6H_5$ |
| JR3179 | 2 | OH | $3\text{-}CH_3$ |
| JR3221 | 2 | OH (R) | $3\text{-}CH_3$ (R) |
| ATL203 | 2 | OH (S) | $3\text{-}CH_3$ (R) |
| MP9041 | 2 | OH (R) | $3\text{-}CH_3$ (S) |
| MP9042 | 2 | OH (S) | $3\text{-}CH_3$ (S) |
| JR3201B | 2 | OH | $3\text{-}(CH_3)_2$ |
| MP9043 | 2 | OH (R) | $3\text{-}CH_2CH_3$ (R) |
| MP9044 | 2 | OH (S) | $3\text{-}CH_2CH_3$ (R) |
| MP9045 | 2 | OH (R) | $3\text{-}CH_2CH_3$ (S) |
| MP9046 | 2 | OH (S) | $3\text{-}CH_2CH_3$ (S) |

TABLE 3-continued

Structure: adenosine with N-ethyl carboxamide ribose, 2-alkynyl-cyclopentyl/cyclohexyl with R³ and (R⁶)ₙ substituents.

| Compound | n | R³ | R⁶ |
|---|---|---|---|
| JR3163 | 2 | OH | 3-(CH₃)₂, 5-(CH₃)₂ |
| JR9875 | 2 | OH | 4-CH₃ |
| JR3149 | 2 | OH | 4-C₂H₅ |
| JR3203 | 2 | OH | 4-C(CH₃)₃ |
| JR3161 | 2 | OH | 4-C₆H₅ |

TABLE 4

Structure: NECA-adenosine with 2-alkynyl-piperazinyl group bearing R¹, R², R⁶.

| Compound | R¹ | R² | R⁶ |
|---|---|---|---|
| JR3213 | H | H | CO₂Et |
| JR3281 | H | H | CO₂tBu |
| JR3289 | H | H | H |
| JR4025 | H | H | cyclohexyl |
| JR4053 | H | H | COMe |
| JR4049 | H | H | CO₂iBu |
| JR3283 | H | H | 2-Pyrimidinyl |
| MP9029 | H | H | COMe |
| MP9030 | H | H | COC(CH₃)₃ |
| MP9031 | H | H | COCH₂(CH₃)₃ |
| MP9032 | H | H | COCH₃ |
| MP9033 | H | H | C(O)N(CH₃)₂ |
| MP9034 | H | H | C(O)N(CH₃)Et |
| MP9035 | H | H | C(O)N(CH₃)iPr |
| MP9036 | H | H | C(O)N(CH₃)iBu |
| MP9037 | H | H | C(O)NH(CH₃) |
| MP9038 | H | H | C(O)NH(Et) |
| MP9039 | H | H | C(O)NH(iPr) |
| MP9040 | H | H | C(O)NH(iBu) |

TABLE 5

Structure: adenosine with R at 5′ position, 2-alkynyl-piperidinyl (4-R⁶) group with R¹, R².

| Compound | R | R¹ | R² | R⁶ |
|---|---|---|---|---|
| MP9021 | NECA | H | H | CH₂OH |
| MP9022 | NECA | H | H | CO₂H |
| JR3251 | NECA | H | H | CO₂Me |

TABLE 5-continued

| Compound | R | R¹ | R² | R⁶ |
|---|---|---|---|---|
| JR3279 | NECA | H | H | CO₂Et |
| MP9027 | CH₂OH | H | H | CO₂Me |
| MP9028 | NECA | H | H | CO₂MeCH₂OAc |
| MP9015 | CH₂OH | H | H | CH₂OAc |
| MP9016 | NECA | H | H | CH₂N(CH₃)₂ |
| MP9017 | NECA | H | H | COOCH₂CH₂NHBoc |
| MP9018 | NECA | H | H | COOCH₂CH₂NH₂ |
| MP9019 | NECA | H | H | CONHCH₂CH₃ |
| MP9020 | NECA | H | H | CONH₂ |
| MP9023 | NECA | H | H | CONHMe |
| MP9024 | NECA | H | H | CH₂CH₃ |
| MP9025 | NECA | H | H | COCH₃ |
| MP9026 | NECA | H | H | CHCH₃(OH) |

NECA = CH₃CH₂N(H)C(O)—

TABLE 6

Structure: adenosine with R at 5′, 2-alkynyl-piperidinyl (2-R⁶) with R¹, R².

| Compound | R | R¹ | R² | R⁶ |
|---|---|---|---|---|
| MP9001 | NECA | H | H | CH₂OH |
| MP9002 | NECA | H | H | CO₂H |
| JR3253 | NECA | H | H | CO₂Me |
| MP9003 | CH₂OH | H | H | CO₂Me |
| MP9004 | NECA | H | H | CH₂OAc |
| MP9005 | CH₂OH | H | H | CH₂OAc |
| MP9006 | NECA | H | H | CH₂N(CH₃)₂ |
| MP9007 | NECA | H | H | COOCH₂CH₂NHBoc |
| MP9008 | NECA | H | H | COOCH₂CH₂NH₂ |
| MP9009 | NECA | H | H | CONHCH₂CH₃ |
| MP9010 | NECA | H | H | CONH₂ |
| MP9011 | NECA | H | H | CONHMe |
| MP9012 | NECA | H | H | CH₂CH₃ |
| MP9013 | NECA | H | H | COCH₃ |
| MP9014 | NECA | H | H | CHCH₃(OH) |

NECA = CH₃CH₂N(H)C(O)—

TABLE 7

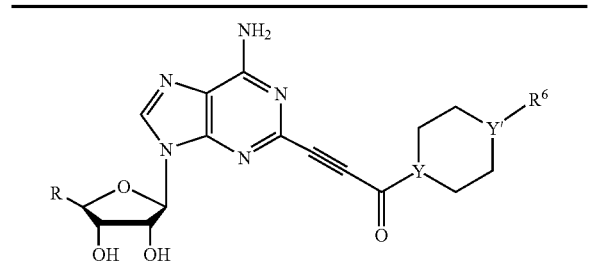

| Compound | R | Y | Y' | R⁶ |
|---|---|---|---|---|
| RJ1111 | NECA | CH | CH | CO$_2$Me |
| RJ1112 | NECA | CH | N | CO$_2$Me |
| RJ1113 | NECA | N | CH | CO$_2$Me |
| RJ1114 | NECA | N | N | CO$_2$Me |
| RJ1115 | NECA | CH | CH | CH$_2$OH |
| RJ1116 | NECA | CH | N | CH$_2$OH |
| RJ1117 | NECA | N | CH | CH$_2$OH |
| RJ1118 | NECA | N | N | CH$_2$OH |
| RJ1119 | NECA | CH | CH | CO$_2$H |
| RJ1120 | NECA | CH | N | CO$_2$H |
| RJ1121 | NECA | N | CH | CO$_2$H |
| RJ1122 | NECA | N | N | CO$_2$H |
| RJ1123 | NECA | CH | CH | CH$_2$OAc |
| RJ1124 | NECA | CH | N | CH$_2$OAc |
| RJ1125 | NECA | N | CH | CH$_2$OAc |
| RJ1126 | NECA | N | N | CH$_2$OAc |
| RJ1127 | NECA | CH | CH | CONH$_2$ |
| RJ1128 | NECA | CH | N | CONH$_2$ |
| RJ1129 | NECA | N | CH | CONH$_2$ |
| RJ1130 | NECA | N | N | CONH$_2$ |
| RJ1131 | NECA | CH | CH | CONHMe |
| RJ1132 | NECA | CH | N | CONHMe |
| RJ1133 | NECA | N | CH | CONHMe |
| RJ1134 | NECA | N | N | CONHMe |
| RJ1135 | NECA | CH | CH | CO$_2$tBu |
| RJ1136 | NECA | CH | N | CO$_2$tBu |
| RJ1137 | NECA | N | CH | CO$_2$tBu |
| RJ1138 | NECA | N | N | CO$_2$tBu |
| RJ1139 | NECA | CH | CH | CO$_2$Et |
| RJ1140 | NECA | CH | N | CO$_2$Et |
| RJ1141 | NECA | N | CH | CO$_2$Et |
| RJ1142 | NECA | N | N | CO$_2$Et |
| RJ1143 | NECA | CH | CH | CO$_2$iBu |
| RJ1144 | NECA | CH | N | CO$_2$iBu |
| RJ1145 | NECA | N | CH | CO$_2$iBu |
| RJ1146 | NECA | N | N | CO$_2$iBu |
| RJ1147 | NECA | CH | CH | CO$_2$iPr |
| RJ1148 | NECA | CH | N | CO$_2$iPr |
| RJ1149 | NECA | N | CH | CO$_2$iPr |
| RJ1150 | NECA | N | N | CO$_2$iPr |
| RJ1151 | NECA | CH | CH | COMe |
| RJ1152 | NECA | CH | N | COMe |
| RJ1153 | NECA | N | CH | COMe |
| RJ1154 | NECA | N | N | COMe |
| RJ1155 | NECA | CH | CH | COC(CH$_3$)$_3$ |
| RJ1156 | NECA | CH | N | COC(CH$_3$)$_3$ |
| RJ1157 | NECA | N | CH | COC(CH$_3$)$_3$ |
| RJ1158 | NECA | N | N | COC(CH$_3$)$_3$ |
| RJ1159 | NECA | CH | CH | COCH$_2$(CH$_3$)$_3$ |
| RJ1160 | NECA | CH | N | COCH$_2$(CH$_3$)$_3$ |
| RJ1161 | NECA | N | CH | COCH$_2$(CH$_3$)$_3$ |
| RJ1162 | NECA | N | N | COCH$_2$(CH$_3$)$_3$ |
| RJ1163 | NECA | CH | CH | C(O)N(CH$_3$)$_2$ |
| RJ1164 | NECA | CH | N | C(O)N(CH$_3$)$_2$ |
| RJ1165 | NECA | N | CH | C(O)N(CH$_3$)$_2$ |
| RJ1166 | NECA | N | N | C(O)N(CH$_3$)$_2$ |
| RJ1167 | NECA | CH | CH | C(O)N(CH$_3$)Et |
| RJ1168 | NECA | CH | N | C(O)N(CH$_3$)Et |
| RJ1169 | NECA | N | CH | C(O)N(CH$_3$)Et |
| RJ1170 | NECA | N | N | C(O)N(CH$_3$)Et |
| RJ1171 | NECA | CH | CH | C(O)N(CH$_3$)iPr |
| RJ1172 | NECA | CH | N | C(O)N(CH$_3$)iPr |
| RJ1173 | NECA | N | CH | C(O)N(CH$_3$)iPr |
| RJ1174 | NECA | N | N | C(O)N(CH$_3$)iPr |

TABLE 7-continued

| Compound | R | Y | Y' | R⁶ |
|---|---|---|---|---|
| RJ1175 | NECA | CH | CH | C(O)N(CH$_3$)iBu |
| RJ1176 | NECA | CH | N | C(O)N(CH$_3$)iBu |
| RJ1177 | NECA | N | CH | C(O)N(CH$_3$)iBu |
| RJ1178 | NECA | N | N | C(O)N(CH$_3$)iBu |
| RJ1179 | NECA | CH | CH | C(O)NH(Et) |
| RJ1180 | NECA | CH | N | C(O)NH(Et) |
| RJ1181 | NECA | N | CH | C(O)NH(Et) |
| RJ1182 | NECA | N | N | C(O)NH(Et) |
| RJ1183 | NECA | CH | CH | C(O)NH(iPr) |
| RJ1184 | NECA | CH | N | C(O)NH(iPr) |
| RJ1185 | NECA | N | CH | C(O)NH(iPr) |
| RJ1186 | NECA | N | N | C(O)NH(iPr) |
| RJ1187 | NECA | CH | CH | C(O)NH(iBu) |
| RJ1188 | NECA | CH | N | C(O)NH(iBu) |
| RJ1189 | NECA | N | CH | C(O)NH(iBu) |
| RJ1190 | NECA | N | N | C(O)NH(iBu) |
| RJ1191 | NECA | CH | CH | CH$_2$OCOCH$_3$ |
| RJ1192 | NECA | N | CH | CH$_2$OCOCH$_3$ |
| RJ1193 | NECA | CH | CH | CH$_2$OCOEt |
| RJ1194 | NECA | N | CH | CH$_2$OCOEt |
| RJ1195 | NECA | CH | CH | CH$_2$OCOiPr |
| RJ1196 | NECA | N | CH | CH$_2$OCOiPr |
| RJ1197 | NECA | CH | CH | CH$_2$OCOiBu |
| RJ1198 | NECA | N | CH | CH$_2$OCOiBu |

NECA = CH$_3$CH$_2$N(H)C(O)—

In another embodiment, agonists of A$_{2A}$ adenosine receptors that are useful in the practice of the present invention include compounds having the formula (II):

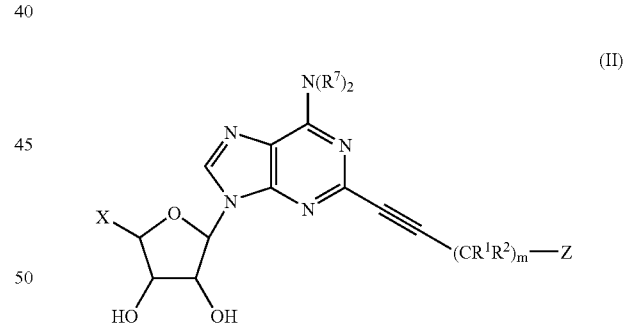

(II)

wherein Z is CR$^3$R$^4$R$^5$; each R$^1$, R$^2$ and R$^3$ is hydrogen; R$^4$ and R$^5$ together with the carbon atom to which they are attached form a cycloalkyl ring having 3, 4, 5, 6, 7, 8, 9 or 10 ring atoms; and wherein the ring comprising R$^4$ and R$^5$ is substituted with —(CH$_2$)$_{0-6}$—Y; where Y is —CH$_2$OR$^a$, —CO$_2$R$^a$, —OC(O)R$^a$, —CH$_2$OC(O)R$^a$, —C(O)NR$^b$R$^c$, —CH$_2$SR$^a$, —C(S)OR$^a$, —OC(S)R$^a$, —CH$_2$OC(S)R$^a$ or C(S)NR$^b$R$^c$ or —CH$_2$N(R$^b$)(R$^c$);

each R$^7$ is independently hydrogen, (C$_1$-C$_8$)alkyl, (C$_3$-C$_8$) cycloalkyl, aryl or aryl(C$_1$-C$_8$)alkylene;

X is —CH$_2$OR$^a$, —CO$_2$R$^a$, —CH$_2$OC(O)R$^a$, —C(O)NR$^b$R$^c$, —CH$_2$SR$^a$, —C(S)OR$^a$, —CH$_2$OC(S)R$^a$, C(S)NR$^b$R$^c$ or —CH$_2$N(R$^b$)(R$^c$);

each $R^a$, $R^b$ and $R^c$ is independently hydrogen, $(C_1-C_8)$alkyl, or $(C_1-C_8)$alkyl substituted with 1-3 $(C_1-C_8)$alkoxy, $(C_3-C_8)$cycloalkyl, $(C_1-C_8)$alkylthio, amino acid, aryl, aryl $(C_1-C_8)$alkylene, heteroaryl, or heteroaryl$(C_1-C_8)$alkylene; or $R^b$ and $R^c$, together with the nitrogen to which they are attached, form a pyrrolidino, piperidino, morpholino, or thiomorpholino ring; and m is 0 to about 6; or a pharmaceutically acceptable salt thereof.

A specific value for $-N(R^7)_2$ is amino, monomethylamino or cyclopropylamino.

A specific value for Z is carboxy- or $-(C_1-C_4)$alkoxycarbonyl-cyclohexyl$(C_1-C_4)$alkyl.

A specific value for $R^a$ is H or $(C_1-C_4)$alkyl, i.e., methyl or ethyl.

A specific value for $R^b$ is H, methyl or phenyl.

A specific value for $R^c$ is H, methyl or phenyl.

A specific value for $-(CR^1R^2)_m-$ is $-CH_2-$ or $-CH_2-CH_2-$.

A specific value for X is $CO_2R^a$, $(C_2-C_5)$alkanoylmethyl or amido.

A specific value for Y is $CO_2R^a$, $(C_2-C_5)$alkanoylmethyl or amido.

A specific value for m is 1.

Specific compounds useful for practicing the invention are compounds JR3259, JR3269, JR4011, JR4009, JR-1085 and JR4007.

Specific $A_{2A}$ adenosine receptor agonists suitable for use with the present invention having formula (II) include those described in U.S. Pat. No. 6,232,297. Specific compounds of formula (II) are those wherein each $R^7$ is H, X is ethylaminocarbonyl and Z is 4-carboxycyclohexylmethyl (DWH-146a), Z is 4-methoxycarbonylcyclohexylmethyl (DWH-146e), Z is 4-isopropylcarbonyl-cyclohexylmethyl (AB-1), Z is 4-acetoxymethyl-cyclohexylmethyl (JMR-193) or Z is 4-pyrrolidine-1-carbonylcyclohexylmethyl (AB-3). Additional compounds useful in practicing the invention are depicted below.

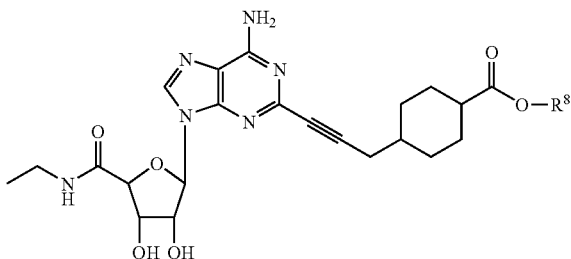

DWH-146: $R^8$ = H or Me.
AB-1: $R^8$ = iPr

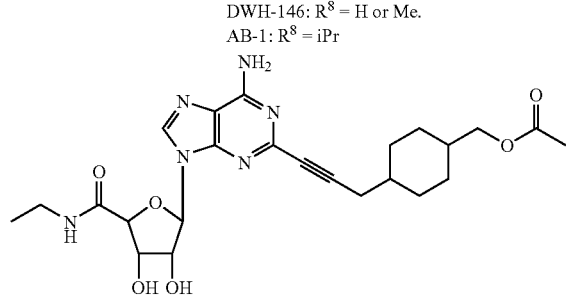

JMR-193

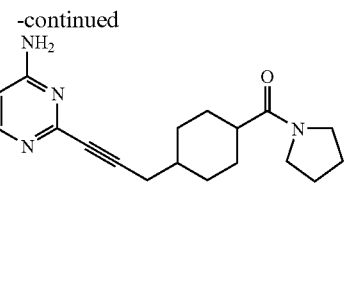

AB-3

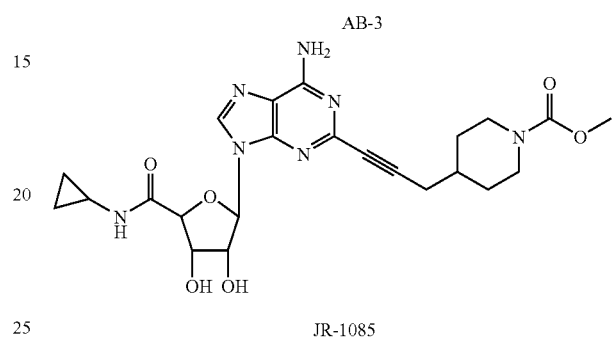

JR-1085

The specific $A_{2A}$ adenosine receptor agonists suitable for use with the present invention having formula (II) include those described in U.S. Pat. No. 6,232,297. These compounds, having formula (II), can be prepared according to the methods described therein.

Another specific group of agonists of $A_{2A}$ adenosine receptors that are useful in the practice of the present invention include compounds having the general formula (III):

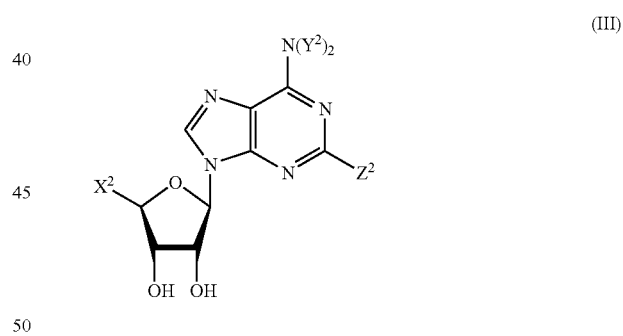

(III)

wherein $Z^2$ is a group selected from the group consisting of $-OR^{12}$, $-NR^{13}R^{14}$, a $-C\equiv C-Z^3$, and $-NH-N=R^{17}$;

each $Y^2$ is individually H, $C_1-C_6$ alkyl, $C_3-C_7$ cycloalkyl, phenyl or phenyl $C_1-C_3$ alkyl;

$R^{12}$ is $C_{1-4}$-alkyl;

$C_{1-4}$-alkyl substituted with one or more $C_{1-4}$-alkoxy groups, halogens (fluorine, chlorine or bromine), hydroxy groups, amino groups, mono($C_{1-4}$-alkyl)amino groups, di($C_{1-4}$-alkyl)amino groups or $C_{6-10}$-aryl groups wherein the aryl groups may be substituted with one or more halogens (fluorine, chlorine or bromine), $C_{1-4}$-alkyl groups, hydroxy groups, amino groups, mono($C_{1-4}$-alkyl)amino groups or di($C_{1-4}$-alkyl)amino groups); or $C_{6-10}$-aryl; or (d) $C_{6-10}$-aryl substituted with one or more halogens (fluorine, chlorine or bromine), hydroxy groups, amino groups, mono($C_{1-4}$-alkyl)amino groups, di($C_{1-4}$-alkyl)amino groups or $C_{1-4}$-alkyl groups;

one of $R^{13}$ and $R^{14}$ has the same meaning as $R^{12}$ and the other is hydrogen; and $R^{17}$ is a group having the formula (i)

(i)

wherein each of $R^{15}$ and $R^{16}$ independently may be hydrogen, ($C_3$-$C_7$)cycloalkyl or any of the meanings of $R^{12}$, provided that $R^{15}$ and $R^{16}$ are not both hydrogen;

$X^2$ is $CH_2OH$, $CH_3$, $CO_2R^{20}$ or $C(=O)NR^{21}R^{22}$ wherein $R^{20}$ has the same meaning as $R^{13}$ and wherein $R^{21}$ and $R^{22}$ have the same meanings as $R^{15}$ and $R^{16}$ or $R^{21}$ and $R^{22}$ are both H;

$Z^3$ has one of the following meanings:

$C_6$-$C_{10}$ aryl, optionally substituted with one to three halogen atoms, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino $C_1$-$C_3$ monoalkylamino, $C_2$-$C_6$ dialkylamino, methylenedioxy or aminocarbonyl;

a group of formula —$(CH_2)_q$-Het wherein q is 0 or an integer from 1 to 3 and Het is 5 or 6 membered heterocyclic aromatic or non-aromatic ring, optionally benzocondensed, containing 1 to 3 heteroatoms selected from non-peroxide oxygen, nitrogen or sulphur, linked through a carbon atom or through a nitrogen atom;

$C_3$-$C_7$ cycloalkyl optionally containing unsaturation or $C_2$-$C_4$ alkenyl;

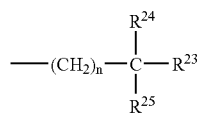

(ii)

wherein $R^{23}$ is hydrogen, methyl or phenyl;

$R^{24}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{23}$ and $R^{24}$, taken together, form a 5 or 6-membered carbocyclic ring or $R^{25}$ is hydrogen and $R^{23}$ and $R^{24}$, taken together, form an oxo group or a corresponding acetalic derivative;

$R^{25}$ is OH, $NH_2$ dialkylamino, halogen, cyano; and n is 0 or 1 to 4; or a) $C_1$-$C_{16}$ alkyl, optionally comprising 1-2 double bonds, O, S or $NY^2$;

or a pharmaceutically acceptable salt thereof.

Specific $C_{6-10}$-aryl groups include phenyl and naphthyl.

Preferably, in the compound of formula (I), $Z^2$ is a group of the formula (iii)

(iii)

wherein n is an integer from 1-4, preferably 2, and Ar is a phenyl group, tolyl group, naphthyl group, xylyl group or mesityl group. Most preferably Ar is a para-tolyl group and n=2.

Preferably, in the compound of formula (II), $Z^2$ is a group of the formula (iv)

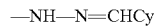

(iv)

wherein Cy is a $C_{3-7}$-cycloalkyl group, preferably cyclohexyl or a $C_{1-4}$ alkyl group, preferably isopropyl.

Preferably, in the compound of formula (II), $Z^2$ is a group of the formula (vii)

(v)

wherein $Z^3$ is $C_3$-$C_{16}$ alkyl, hydroxy $C_2$-$C_6$ alkyl or (phenyl) (hydroxymethyl).

Specific examples of such compounds of formula (I) include WRC-0470, WRC-0474 [SHA 211], WRC-0090 and WRC-0018, shown below:

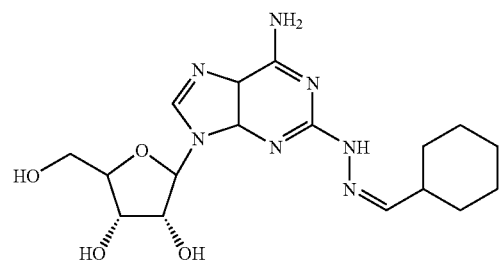

WRC-0470

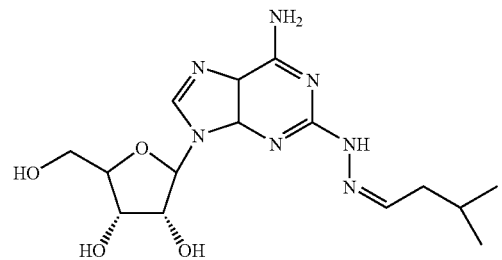

WRC-0474

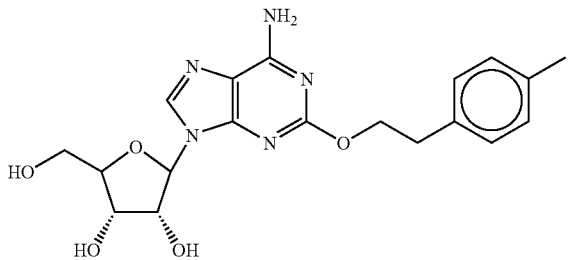

WRC-0090

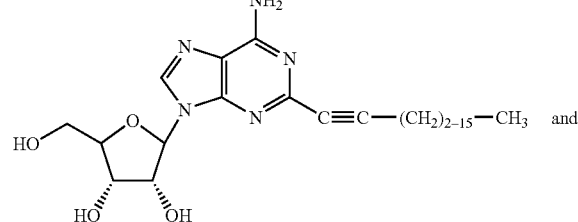

and

-continued

WRC-0018

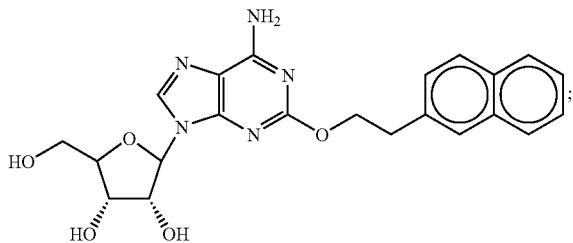

wherein the H on CH₂OH can optionally be replaced by ethylaminocarbonyl. Of these specific examples, WRC-0474[SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199-204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

Another embodiment includes compounds having formula (III) where $Z^2$ is a group having formula (vi):

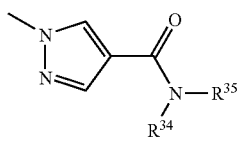

(vi)

wherein $R^{34}$ and $R^{35}$ are independently H, $C_1$-$C_6$ alkyl, $C_3$-$C_7$ cycloalkyl, phenyl, phenyl $C_1$-$C_3$ alkyl or $R^{34}$ and $R^{35}$ taken together with the nitrogen atom are a 5- or 6-membered heterocyclic ring containing 1-2 heteroatoms selected from non-peroxide oxygen, nitrogen (N($R^{13}$)) or sulphur atoms. Preferably one of $R^{34}$ and $R^{35}$ is hydrogen and the other is ethyl, methyl or propyl. More preferably one of $R^{34}$ and $R^{35}$ is hydrogen and the other is ethyl or methyl.

The 2-(pyrazol-1-yl)adenosine compounds of the invention, wherein $Z^2$ is a group having formula (vi), can be prepared by reacting a 2-chloro- or 2-iodo adenosine derivative with an 1H-pyrazole-4-carboxamides compound having formula (vii):

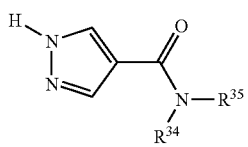

(vii)

where $R^{34}$ and $R^{35}$ are as described above, wherein selective protection/deprotection of the amido group is used as needed. A specific pyrazole derivative useful in practicing this invention is a compound having the formula:

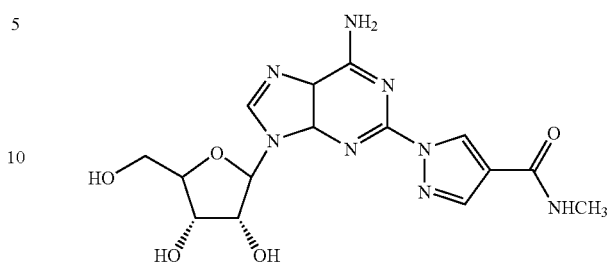

The 1H-pyrazole-4-carboxamides can be prepared starting with 1H-pyrazole-4-carboxylic acid, available from Aldrich Chemical Co. In the first step, the acid is converted to an ester, e.g., a methyl or ethyl ester. The ester converted to the amide via aminolysis, e.g., with methylamine to form the methyl amide. The pyrazole-4-carboxamide will react with the 2-halopurines in the presence of a strong base to provide the 2-(pyrazol-1-yl)adenosine compounds having formula (III).

Another specific group of agonists of $A_{2A}$ adenosine receptors that are useful in the practice of the present invention include compounds having the general formula (IV):

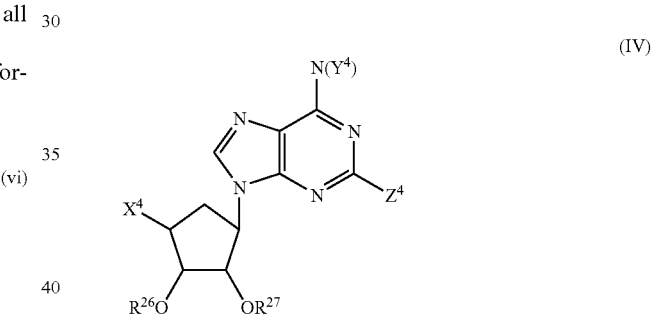

(IV)

wherein $Z^4$ is —$NR^{28}R^{29}$;
  $R^{28}$ is hydrogen or ($C_1$-$C_4$)alkyl; and $R^{29}$ is
  a) ($C_1$-$C_4$)alkyl;
  b) ($C_1$-$C_4$)alkyl substituted with one or more ($C_1$-$C_4$) alkoxy, halogen, hydroxy, amino, mono(($C_1$-$C_4$) alkyl)amino, di(($C_1$-$C_4$)alkyl)amino or ($C_6$-$C_{10}$)aryl wherein aryl is optionally substituted with one or more halogen, hydroxy, amino, ($C_1$-$C_4$)alkyl, $R^{30}$OOC—(($C_1$-$C_4$)alkyl)-, $R^{31}R^{32}$NC(=O)—(($C_1$-$C_4$)alkyl)-, mono(($C_1$-$C_4$)alkyl)amino or di(($C_1$-$C_4$) alkyl)amino;
  c) ($C_6$-$C_{10}$)aryl; or
  d) ($C_6$-$C_{10}$)aryl substituted with one or more halogen, hydroxy, amino, mono(($C_1$-$C_4$)alkyl)amino, di(($C_1$-$C_4$)alkyl)amino or ($C_1$-$C_4$)alkyl;
    wherein each $Y^4$ is individually H, ($C_1$-$C_6$)alkyl, ($C_3$-$C_7$) cycloalkyl, phenyl or phenyl($C_1$-$C_3$)alkyl; and $X^4$ is —C(=O)$NR^{31}R^{32}$, —COOR$^{30}$, or —CH$_2$OR$^{30}$;
    wherein each of $R^{31}$ and $R^{32}$ are independently; hydrogen; $C_{3-7}$-cycloalkyl; ($C_1$-$C_4$)alkyl; ($C_1$-$C_4$)alkyl substituted with one or more ($C_1$-$C_4$)alkoxy, halogen, hydroxy, —COOR$^{33}$, amino, mono(($C_1$-$C_4$)alkyl)amino, di(($C_1$-$C_4$)alkyl)amino or ($C_6$-$C_{10}$)aryl wherein aryl is optionally substituted with one or more halogen, ($C_1$-$C_4$)alkyl, hydroxy, amino, mono (($C_1$-$C_4$)alkyl)amino or di(($C_1$-$C_4$)alkyl)amino; ($C_6$-$C_{10}$)aryl; or ($C_6$-$C_{10}$)aryl substituted with one or more halogen, hydroxy, amino, mono(($C_1$-$C_4$)alkyl)amino, di(($C_1$-$C_4$)alkyl)amino or ($C_1$-$C_4$)alkyl;

$R^{26}$ and $R^{27}$ independently represent hydrogen, lower alkanoyl, lower alkoxy-lower alkanoyl, aroyl, carbamoyl or mono- or di-lower alkylcarbamoyl; and $R^{30}$ and $R^{33}$ are independently hydrogen, ($C_1$-$C_4$)alkyl, ($C_6$-$C_{10}$)aryl or ($C_6$-$C_{10}$)aryl(($C_1$-$C_4$)alkyl); or a pharmaceutically acceptable salt thereof.

In one embodiment of formula (IV), at least one of $R^{28}$ and $R^{29}$ is ($C_1$-$C_4$)alkyl substituted with one or more ($C_1$-$C_4$)alkoxy, halogen, hydroxy, amino, mono(($C_1$-$C_4$)alkyl)amino, di(($C_1$-$C_4$)alkyl)amino or ($C_6$-$C_{10}$)aryl wherein aryl is optionally substituted with one or more halogen, hydroxy, amino, ($C_1$-$C_4$)alkyl, $R^{30}$OOC—($C_1$-$C_4$)alkyl, mono(($C_1$-$C_4$)alkyl)amino or di(($C_1$-$C_4$)alkyl)amino.

In another embodiment, at least one of $R^{31}$ and $R^{32}$ is $C_{1-4}$-alkyl substituted with one or more ($C_1$-$C_4$)alkoxy, halogen, hydroxy, amino, mono(($C_1$-$C_4$)alkyl)amino, di(($C_1$-$C_4$)alkyl)amino or $C_{6-10}$-aryl wherein aryl is optionally substituted with one or more halogen, hydroxy, amino, ($C_1$-$C_4$)alkyl, $R^{30}$OOC—($C_1$-$C_4$)alkylene-, mono(($C_1$-$C_4$)alkyl)amino or di(($C_1$-$C_4$)alkyl)amino.

In another embodiment, at least one of $R^{28}$ and $R^{29}$ is $C_{6-10}$-aryl substituted with one or more halogen, hydroxy, amino, mono(($C_1$-$C_4$)alkyl)amino, di(($C_1$-$C_4$)alkyl)amino or ($C_1$-$C_4$)alkyl.

In another embodiment, at least one of $R^{31}$ and $R^{32}$ is $C_{6-10}$-aryl substituted with one or more halogen, hydroxy, amino, mono(($C_1$-$C_4$)alkyl)-amino, di(($C_1$-$C_4$)alkyl)amino or ($C_1$-$C_4$)alkyl.

In a specific combination, $R^{31}$ is hydrogen and $R^{32}$ is ($C_1$-$C_4$)alkyl, cyclopropyl or hydroxy-($C_2$-$C_4$)alkyl. A specific $R^{28}$ group is ($C_1$-$C_4$)alkyl substituted with ($C_6$-$C_{10}$) aryl, that is in turn substituted with $R^{30}$O(O)C—($C_1$-$C_4$) alkylene-.

A specific compound having formula (IV) is:

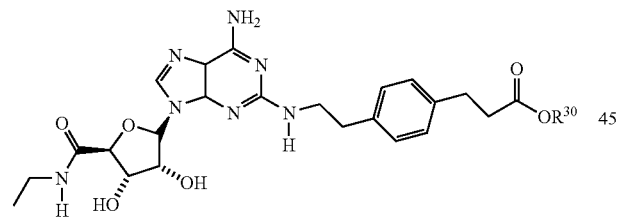

wherein $R^{30}$ is hydrogen, methyl, ethyl, n-propyl or iso-propyl. More preferred is a compound wherein the $R^{30}$ group is methyl or ethyl. The most preferred $R^{30}$ group is methyl.

Two compounds that are particularly useful in practicing the present invention have the formula:

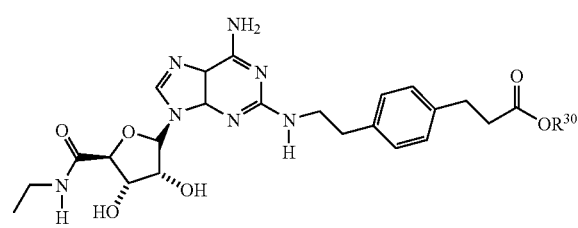

wherein $R^{30}$ is hydrogen (acid, CGS21680) and where $R^{30}$ is methyl (ester, JR2171).

The compounds of the invention having formula (IV) may be synthesized as described in: U.S. Pat. No. 4,968,697 or *J. Med. Chem.*, 33, 1919-1924, (1990)

Specifically, the invention also provides the use of a compound of formula (I) or a pharmaceutically acceptable salt thereof to prepare a medicament for treating systemic intoxification in a mammal (e.g., a human).

Specifically, the invention also provides the use of a compound of formula (I) or a pharmaceutically acceptable salt thereof to prepare a medicament for treating inflammation caused by bacterial, fungal or viral infections and the inflammation caused by the treatment of these infections, e.g., by the death of the bacterial or viral cells in a mammal (e.g., a human).

The present method also includes the administration of a Type IV phosphodiesterase (PDE) inhibitor in combination with compounds having formulae (I), (II), (III), and (IV). The combination of the compounds of the invention with type IV phosphodiesterase inhibitor provides synergistic decreases in the inflammatory response of immune cells. Examples of Type IV phosphodiesterase (PDE) inhibitors include those disclosed in U.S. Pat. No. 4,193,926, and WO 92-079778, and Molnar-Kimber, K. L. et al., *J. Immunol.*, 150, 295A (1993), all of which are incorporated herein by reference.

Suitable Type IV phosphodiesterase (PDE) inhibitors include racemic and optically active 4-(polyalkoxyphenyl)-2-pyrrolidones of general formula (VI):

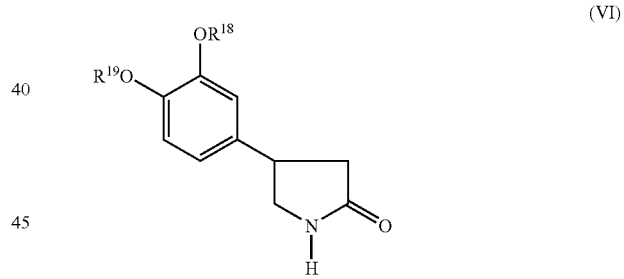

(disclosed and described in U.S. Pat. No. 4,193,926) wherein $R^{18}$ and $R^{19}$ are independently the same or different and are hydrocarbon radicals having up to 18 carbon atoms with at least one being other than methyl, a heterocyclic ring, or alkyl of 1-5 carbon atoms which is substituted by one or more of halogen atoms, hydroxy, carboxy, alkoxy, alkoxycarbonyl or an amino group or amino.

Examples of hydrocarbon $R^{18}$ and $R^{19}$ groups are saturated and unsaturated, straight-chain and branched alkyl of 1-18, preferably 1-5, carbon atoms, cycloalkyl and cycloalkylalkyl, preferably 3-7 carbon atoms, and aryl and aralkyl, preferably of 6-10 carbon atoms, especially monocyclic.

Rolipram is an example of a suitable Type IV phosphodiesterase or PDE inhibitor included within the above formula. Rolipram has the following formula:

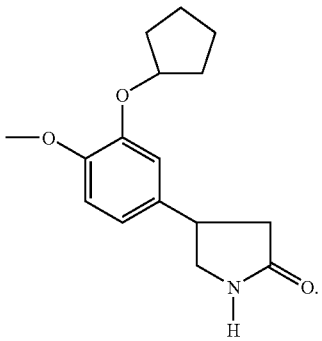

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 µg/kg, preferably about 0.1 to about 50 µg/kg, and more preferably about 0.1 to about 10 µg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The preparation of compounds useful in practicing the present invention are disclosed in U.S. patent application Ser. No. 10/236,379, filed Oct. 1, 2002, and can generally be prepared as illustrated in Schemes 1A and 1B below. Starting materials can be prepared by procedures described in these schemes, procedures described in the General methods below or by procedures that would be well known to one of ordinary skill in organic chemistry. The variables used in Schemes 1A and Scheme 1B are as defined herein or as in the claims.

The preparation of alkynyl cycloalkanols is illustrated in Scheme 1A. A solution of an appropriate cycloalkanone (where j is from 0-5) is prepared in a solvent such as THF. A solution of a suitable ethynylmagnesium halide compound in a solvent is added to the cycloalkanone. After addition, the solution is allowed to stir at about 20 C for about 20 hours. The reaction is monitored via TLC until the starting material is consumed. The reaction is quenched with water, filtered over a plug of sand and silica, washed with a solvent, such as EtOAc, and evaporated to provide the product. Typically, two products are formed, the isomers formed by the axial/equatorial addition of the alkyne (where m is as defined above, and the sum of m1 and m2 is from 0 to about 7) to the ketone. The compounds are purified via flash chromatography using EtOAc/Hexanes to provide the product.

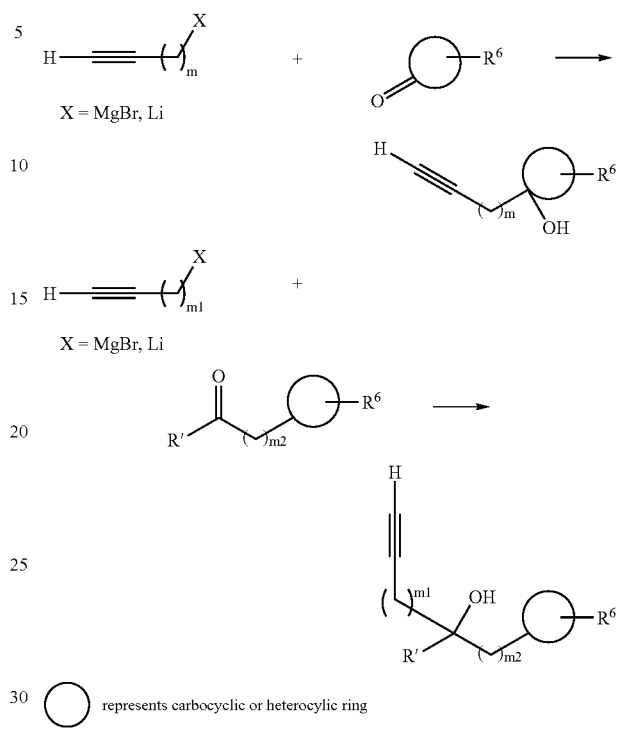

Scheme 1A

In accordance with one embodiment of the present invention a composition comprising an agonist of $A_{2A}AR$ is administered to a patient to treat septic shock and systemic inflammatory response syndrome. As used herein the term "treating" includes prophylaxis of the specific disorder or condition, or alleviation of the symptoms associated with a specific disorder or condition and/or preventing or eliminating said symptoms. In one embodiment a method for treating septic shock or systemic inflammatory response syndrome is provided wherein an agonist of $A_{2A}ARs$ is administered to a patient to reduce inflammation and improve survival in a patient suffering from septic shock or systemic inflammatory response syndrome. In one embodiment the $A_{2A}AR$ agonist is selected from the group consisting of ATL146e, AB-1, AB-3 and JR-3213.

The preparation of 2-alkynyladenosines is illustrated in Scheme 1B. A flame-dried round bottom under nitrogen is charged with 5-(6-Amino-2-iodo-purin-9-yl)-3,4-dihydroxytetrahydrofuran-2-carboxylic acid ethylamide (NECA 2-Iodoadenosine) and a solvent such as DMF. The appropriate alkyne, wherein R is a $-(CR^1R^2)_m$ Z group, is dissolved in acetonitrile followed by TEA, 5 mole % Pd(PPh$_3$)$_4$, and CuI. All solvents are thoroughly degassed.

The solution is allowed to stir for about 24 hours at room temperature, and monitored until complete by HPLC. If the reaction is not complete after this time, additional catalyst, CuI, and TEA are added. After the reaction is complete, the solvents are removed under high-vacuum and the residue taken up in a small amount of DMF. This product is isolated using preparative silica TLC. The product is purified by RP-HPLC.

Scheme 1B

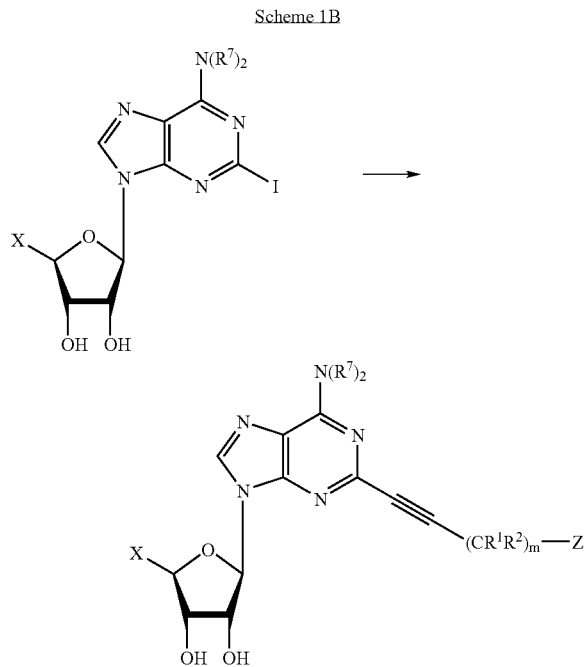

The following abbreviations have been used herein:

| | |
|---|---|
| 2-Aas | 2-alkynyladenosines; |
| $^{125}$I-ABA | $N^6$-(4-amino-3-[125]iodo-benzyl)adenosine |
| APCI | Atmospheric pressure chemical ionization |
| ATL146e | 4-{3-[6-Amino-9-(5-ethylcarbamoyl-3,4-dihydroxy-tetrahydro-furan-2-yl)-9H-purin-2-yl]-prop-2-ynyl} cyclohexanecarboxylic acid methyl ester; |
| CCPA | 2-chloro-$N^6$-cyclopentyladenosine; |
| CGS21680 | 2-[4-(2-carboxyethyl)phenethylamino]-5'-N-ethyl-carboxamidoadenosine; |
| Cl-IB-MECA | $N^6$-3-iodo-2-chlorobenzyladenosine-5'-N-methyluronamide; |
| CPA | $N^6$-cyclopentyladenosine |
| DMF | dimethylformamide |
| DMSO | dimethylsulfoxide |
| DMSO-$d_6$ | deuterated dimethylsulfoxide |
| EtOAc | ethyl acetate |
| eq | equivalent |
| GPCR | G protein coupled receptor; $hA_{2A}AR$, Recombinant human $A_{2A}$ adenosine receptor; |
| IADO | 2-Iodoadenosine |
| $^{125}$I-APE, | 2-[2-(4-amino-3-[$^{125}$I]iodophenyl)ethylamino]-adenosine; |
| NECA | 5'-N-ethylcarboxamidoadenosine; |
| IB-MECA | $N^6$-3-iodobenzyladenosine-5'-N-methyluronamide; |
| 2-Iodoadenosine | 5-(6-amino-2-iodo-purin-9-yl)-3,4-dihydroxytetra-hydro-furan-2carboxylic acid ethylamide |
| HPLC | high-performance liquid chromatography |
| HRMS | high-resolution mass spectrometry |
| [125]I-ZM241385, | [125]I-4-(2-[7-amino-2-[2-furyl][1,2,4]triazolo[2,3-a]-[1,3,5]triazin-5-yl-amino]ethyl)phenol; |
| INECA | 2-iodo-N-ethylcarboxamidoadenosine |
| LC/MS | liquid chromatography/mass spectrometry |
| m.p. | melting point |
| MHz | megahertz |
| MRS 1220, | N-(9-chloro-2-furan-2-yl-[1,2,4]triazolo[1,5-c]-quinazolin-5-yl)-2-phenylacetamide; |
| MS | mass spectrometry |
| NECA | N-ethylcarboxamidoadenosine |
| NMR | nuclear magnetic resonance |
| RP-HPLC | reverse phase high-performance liquid chromatography |
| TBAF | tetrabutylammonium fluoride |
| TBS | tert-butyldimethylsilyl |
| TBDMSCl | tert-butyldimethylsilylchloride |
| TEA | triethylamine |
| TFA | trifluoroacetic acid |
| THF | tetrahydrofuan |
| TLC | thin layer chromatography |
| p-TSOH | para-toluenesulfonic acid |
| XAC | 8-(4-((2-a-minoethyl)aminocarbonyl-methyloxy)-phenyl)-1-3-dipropylxanthine. |

Arthritis Studies:

Arthritis Induction and Assessment. Arthritis is induced by a single intraperitoneal injection of the Streptococcal cell wall product peptidoglycan-polysaccharide (PGPS) on Day 0, and assessed (by an assessor) daily through the acute phase (Days 1-10), then thrice weekly until at least day 28. Non-arthritic control rats receive an equal volume of saline administered IP. Typically 95-100 percent of animals injected with PGPS develop arthritis. PGPS injection and treatments are administered by an independent operator, and the assessor blinded to the treatment, to prevent bias.

Joint swelling is scored (arthritis score) by a standardized method by an experienced observer (assessor). A score of 0-4 is assigned as follows: 0—no evidence of hyperemia and/or inflammation; 1—hyperemia with little or no paw swelling; 2—swelling confined predominantly to the ankle region with modest hyperemia; 3—increased paw swelling and hyperemia of the ankle and metatarsal regions; 4—maximal paw swelling and hyperemia involving the ankle, metatarsal and tarsal regions. For final analysis, scores are summed for all paws, thus the maximum possible score is 16.

Histological evaluation. Rat ankle (hind paw) joints are fixed at 4° C. in Zamboni's fixative, decalcified in an extraction buffer (EDTA). The joints are split, placed in cryomolds containing TBS tissue freezing medium (Triangle Biomedical Sciences, Durham, N.C.) and frozen in liquid nitrogen. Serial sections (10-12 μm thick) are cut parallel to the long axis of the joint. The sections are stained with Masson's Trichrome Stain (Sigma Chemical Co. St. Louis Mo.). Images are captured using a Nikon E600 microscope equipped with a SynSys digital camera (Photometrics, Tucson, Ariz.). Exposure times are automatically determined using the Trichrome Image dialog of MetaMorph Software (Universal Imaging, Downingtown, Pa.). Histologic analysis are determined by a blinded pathologist using a validated scoring system for cellular infiltrate, synovial hypertrophy, and bone destruction (Sakiniene E, et al., Clinical and Experimental Immunology 1999; 115(1):95-102).

Drug administration. The $A_{2A}R$ agonist JR-1085, $A_{2A}R$ selective antagonist ZM241385, and other drugs are administered by subcutaneous implantation of Alzet minipumps to provide even delivery. (Alzet osmotic pumps (Durect Corp., Cupertino, Calif.) are miniature, implantable pumps used for research in laboratory animals. These pumps can be used for the systemic administration of drugs or small molecules such as cytokines, peptides, and growth factors at predictably controlled rates independent of the physical and chemical properties of the compounds.) The pumps come in sizes up to 2 ml volume with delivery duration up to 4 weeks, suitable for use in rats. The pumps are \ replaced at 4 week intervals for long-term studies.

Flow Cytometry. Heparinized rat blood samples are collected by cardiac puncture under anesthesia. One mL is immediately transferred to a separate tube for collection of plasma for cytokine analysis. The remainder is retained for cell analysis. Lymph nodes and spleen are surgically excised and single cell suspensions prepared by passing through a 70 micron nylon mesh (Becton-Dickinson, Franklin Lakes, N.J.). Cells are collected in Hank's buffered salt solution (HBSS), and red cells present in spleen and blood are lysed using NH4Cl buffer, washed twice in HBSS, and resuspended in HBSS with 2% fetal bovine serum. Viable cell count in each tissue is carried out using trypan blue and hemocytometer counting.

Immunofluorescent staining is carried out after washing in PBS with 1% BSA and 0.1% sodium azide (FACS buffer), then incubated on ice for 30 minutes with appropriate mAb or isotype controls. At the end of the incubation period cells are washed twice with 300 µl FACS buffer, then resuspended in 100 µl FACS buffer plus 100 µl 2% Ultrapure (EM grade) formaldehyde (Polysciences, Warrington, Pa.). When appropriate, cells are incuabated with biotin-conjugated mAb, washed three times, incubated for 30 minutes with the relevant streptavidin conjugate, and then fixed as above. Cell fractions are gated on viable cells and sample data acquired using a FACSCalibur flowcytometer (Becton Dickinson) in the UVA Flow Cytometry Core Facility. Cell acquisition and analysis is performed on at least 10,000 independent events. Data is analyzed using CellQuest (Becton Dickinson) or FloJo (Tree Star, Inc., Ashland, Oreg.) software. Lymphocytes, monocytes, and neutrophils are initially distinguished in a flow histogram based on forward versus side scatter (FSC/SSC) properties. Further identification and characterization is by lineage specific antibodies and other markers (all available from BD-Pharmingen) as outlined in Table 5. Detailed analysis of cell subtypes and activation is previously described by Kimpel D, et al., Clinical Immunology 2002; 105:351-362 and Kimpel D, et al., Inflammation 2003; 27(2):59-70.

TABLE 5

Rat antibody markers for flow cytometry

| Specificity | Marker |
|---|---|
| T lymphocyte | CD3 |
| T lymphocyte subset | CD4 |
| Monocyte | 1C7 |
| Granulocyte | RP1 |
| Activation | CD44 |
| Activation/regulatory | CD25 |
| Th1 | CD45RC |

Cytokine measurement. TNFα and IL-1β in plasma samples will be determined as we have done previously using enzyme-linked immunosorbent assay kits (R&D Systems, Minneapolis, Minn.) according to the manufacturer's recommendations.

EXAMPLE 1

A chronic T-cell dependent inflammatory arthritis is induced in female Lewis rats by a single intraperitoneal (i.p.) injection of the Streptococcal cell wall (SCW) component peptidoglycan-polysaccharide (PGPS; Lee Labs, Athens Ga; 25 mg/kg based on rhamnose content). The arthritic control group is administered PGPS and vehicle alone, and treatment control will receive dexamethasone, 2 mg/kg/day. A non-arthritic control group will be used to establish baseline levels for cell surface marker and cytokine studies. Arthritis is assessed by ankle volume plethysmography (Buxco Electronics), by a visual scoring scale, and followed up by histopathology.

Arthritis is scored by an experienced, blinded observer daily for the first 10 days, then thrice weekly for the remaining period. At the end of the treatment period animals will be sacrificed. Their secondary lymphoid organs (spleen, draining lymph node, and mesenteric lymph node) will be analyzed by flow cytometry, and serum saved for cytokine measurements using protocols currently in use in our laboratory. Ankles will be fixed and decalcified, bisected longitudinally, embedded and sectioned for histopathologic evaluation of arthritis. Once the effective dose is established, the serum from those samples will be analyzed for TNF-α and IL-1 levels, and compared to control values.

Figure 3:
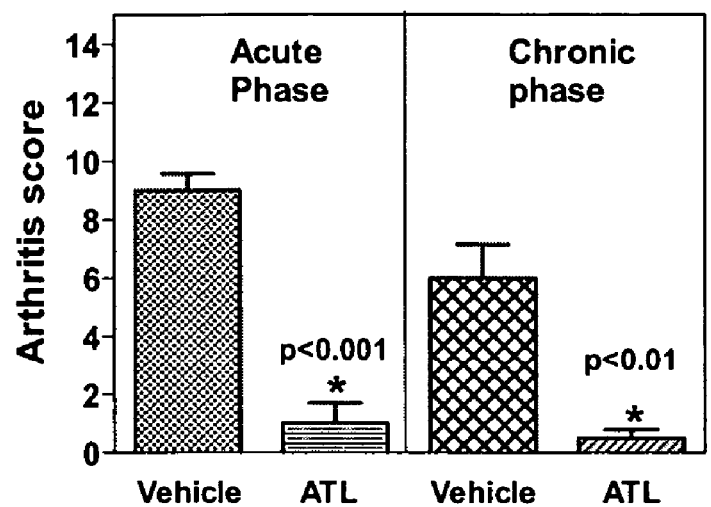
FIG. 3 is a graph of the Total Joint Score for Animals Treated with test compound (JR-1085) or vehicle (control).

Female Lewis rats were implanted with primed, mini-osmotic pumps containing a test compound (JR-1085) or vehicle on the day of PGPS injection for arthritis induction (Day 0). (The rats are administered test compound, (3 dosages of JR-1085), via Alzet pump for 30 days.) Animals were scored daily through the first 10 days, then three times weekly. In order to calculate the effectiveness of the test compounds is suppressing arthritis and determine if there was a differential effect in the acute vs. the chronic phases, the maximum score determined for each animal during the acute (days 1-5) and chronic (days 21-28) phases. Using the highest arthritic score for each animal in each phase, the mean joint score and standard deviation for each group is shown in FIG. 3. There was a significant difference between JR-1085 and vehicle treated groups in both the acute and chronic phases. Preliminary review of histopathology also indicates protection from joint destruction by JR-1085 in the animals.

Figure 4:
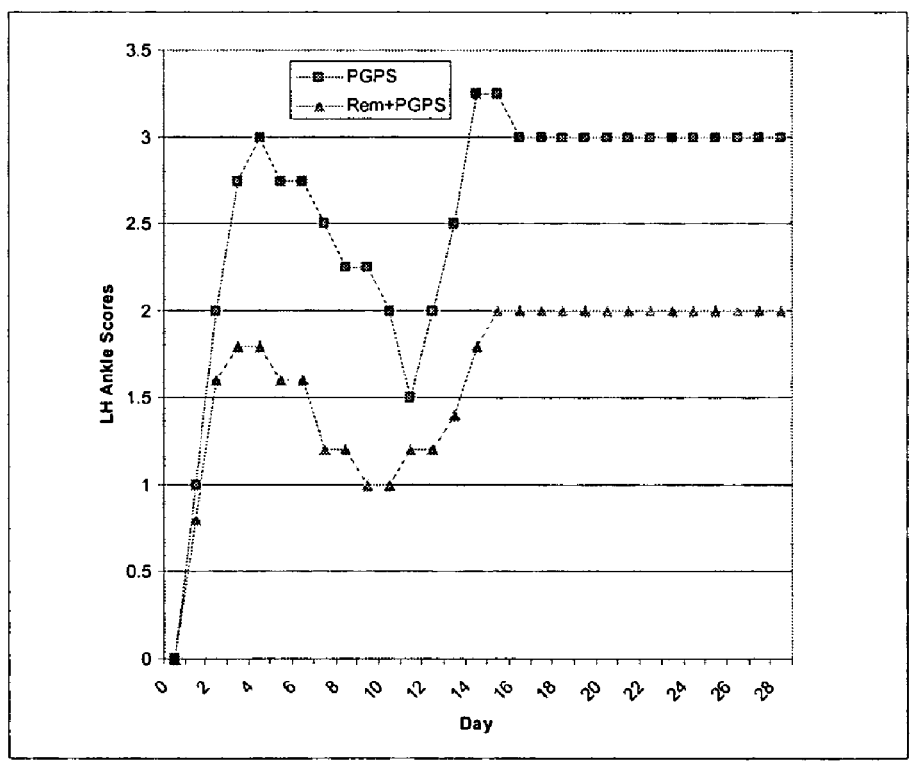
FIG. 4 illustrates the Representative Hindlimb Scores after Treatment with Remicade Compared to Untreated Animals.

The test compounds were evaluated against infliximab (Remicade), a chimeric anti-TNF monoclonal antibody in PGPS treated rats. A single intraperitoneal injection of 3 mg/kg infliximab, administered one day prior to intraperitoneal injection of PGPS had a suppressive effect on the course of arthritis in both the early (acute) phase, and the chronic phase, similar to the effect seen with JR-1085 (FIG. 4). The mean left hindpaw score is shown as representative of the course of PGPS-induced (SCW) arthritis treated with infliximab or vehicle. We have demonstrated that TNFα protein and mRNA is present in rats with PGPS arthritis, as it is in human RA (See Feldmann M., J R Coll Physicians Lond 1996; 30(6):560-570.)

Figure 5:
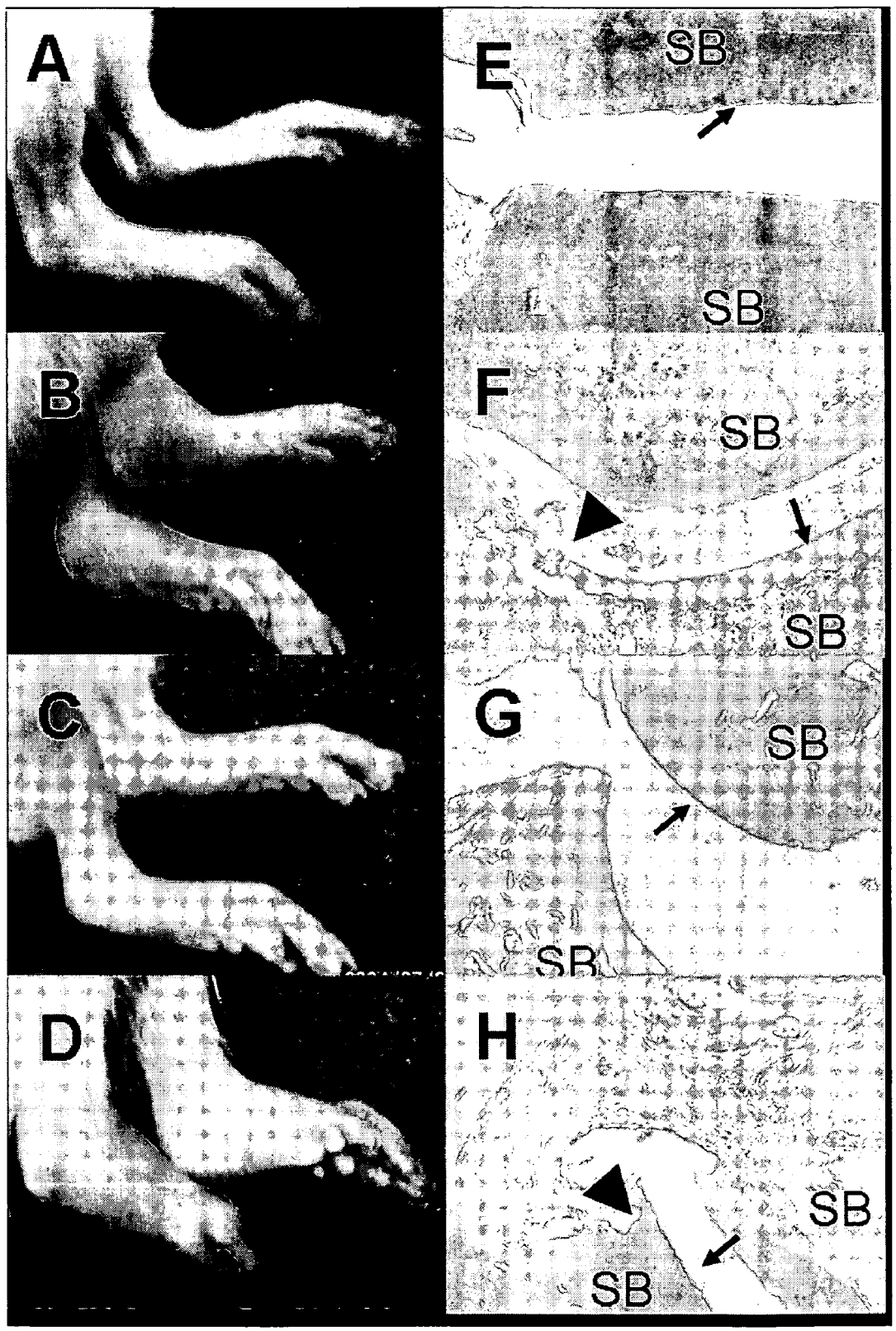
FIGS. 5A-H are images of gross appearance and the histology of the the rat ankles. A,E—Normal Rat (control untreated); B,F—Arthritic (SCW) Rat, treated with PGPS only; C,G—SCW rat treated with JR-1085 (1 ng/kg/min); D,H—SCW rat treated with JR-1085 and ZM241385 (10 ng/kg/min).
Figure 6:
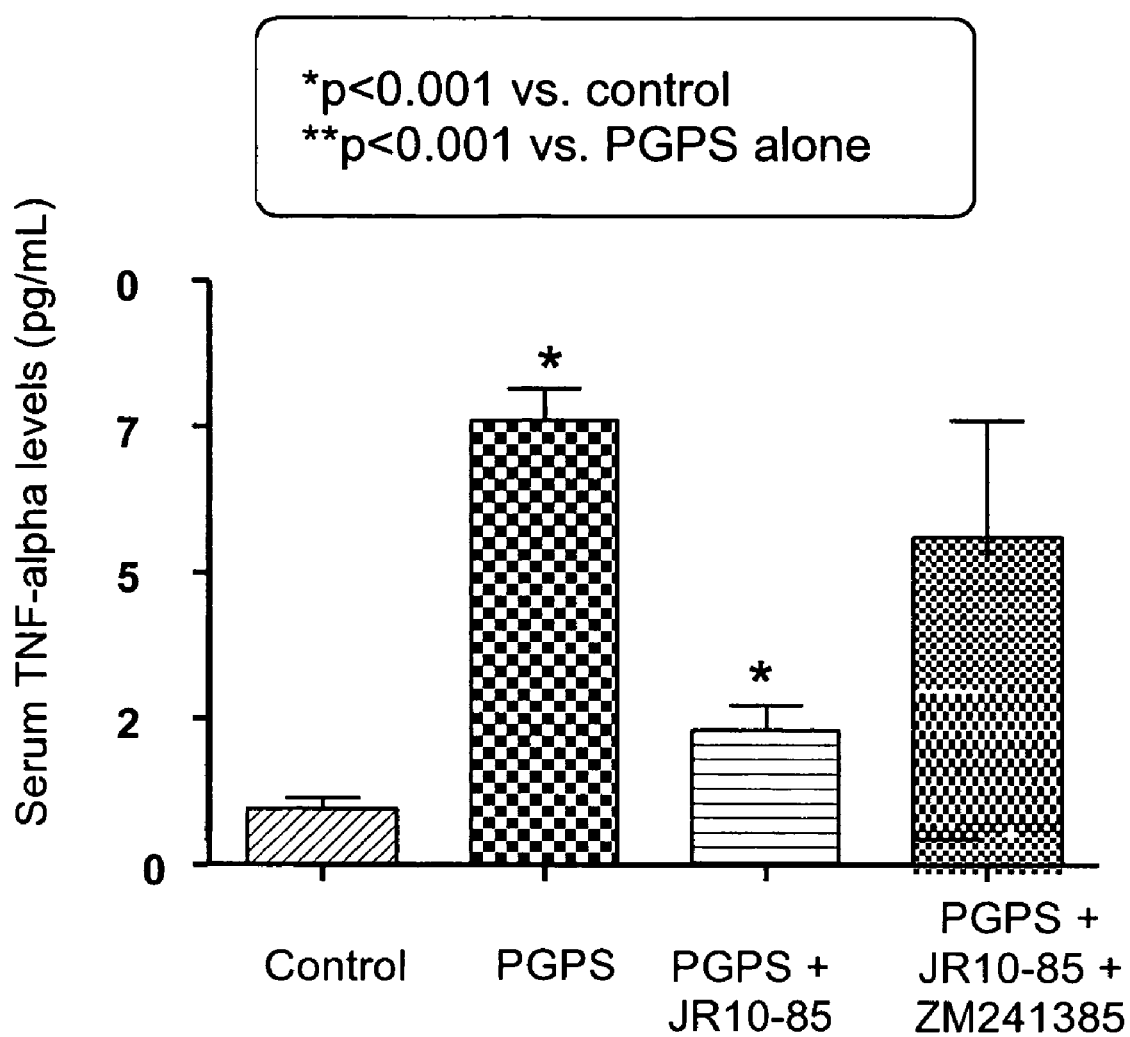
FIG. 6 illustrates the Effects of JR-1085 on TNFα levels after treatment with PGPS.

The results are illustrated in FIG. 5. In FIG. 5, the normalizing effect of JR1085 on the gross appearance and histology of the ankles in animals with SCW arthritis. All animals except A and E received PGPS by IP injection. As shown in panels B and F, PGPS induces severe inflammation, swelling, thickening of the synovial membrane and joint capsule, erosions of the cartilage (large arrow heads), and destruction of subchondral bone (SB). Treatment with JR1085 (Panels C and G) prevented these changes, resulting in normal appearing cartilage (long arrows), synovial tissue, and subchondral bone. Co-administration of the $A_{2A}R$ antagonist ZM and JR1085 (Panels D and H) abrogated the protective effect of JR1085, confirming the role of $A_{2A}R$ in controlling inflammation.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method for treating an inflammatory response caused by autoimmune stimulation, comprising the administration to a patient in need thereof of an antiinflammatory amount of an $A_{2A}$ adenosine receptor agonist, wherein the $A_{2A}$ adenosine receptor agonist is a compound having formula (I):

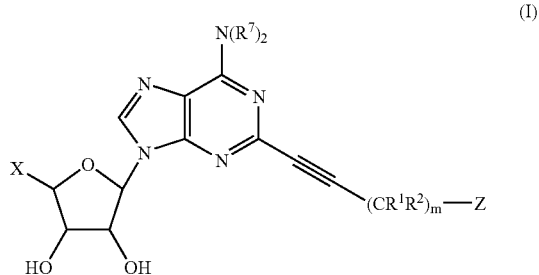

wherein
Z is $CR^3R^4R^5$;
each $R^1$ is independently hydrogen;
each $R^2$ is independently hydrogen;
$R^4$ and $R^5$ together with the atoms to which they are attached form a saturated mono- or bicyclic cycloalkyl ring having 3, 4, 5, 6, 7, 8, 9 or 10 ring atoms wherein the cycloalkyl optionally comprises 1-2 N, O, or S;
wherein any ring comprising $R^4$ and $R^5$ is substituted with from 1 to 3 $R^6$ groups; wherein each $R^6$ is independently $(C_1-C_6)$alkyl, $CH_2OH$, $-CO_2R^a$, $R^aC(=O)O-$, or $R^bR^cNC(=O)$;
$R^3$ is hydrogen;
each $R^7$ is independently hydrogen, $(C_1-C_6)$alkyl, $(C_3-C_7)$cycloalkyl, phenyl or phenyl $(C_1-C_6)$alkylene;
X is $CH_2OH$, $-CO_2R^a$, $-CH_2OC(O)R^a$, or $-C(O)NR^bR^c$;
wherein any alkyl group of $R^6$ is optionally substituted on carbon with one or more substituents selected from the group consisting of $CH_2OH$, $-CO_2R^a$, $R^aC(=O)O-$, $R^aC(=O)-$, and $R^bR^cNC(=O)-$;
wherein each $R^a$, $R^b$ and $R^c$ is independently hydrogen, $(C_1-C_6)$alkyl, or $(C_1-C_6)$alkyl substituted with 1-3$(C_1-C_6)$alkoxy, $(C_3-C_6)$cycloalkyl, $(C_1-C_6)$alkylthio, aryl, or aryl$(C_1-C_6)$alkylene;
m is 0 to 6; or
a pharmaceutically acceptable salt thereof.

2. The method of claim 1, wherein the ring comprising $R^4$, $R^5$ and the atom to which they are connected is cyclopentane, cyclohexane, piperidine, piperazine, decaline, hexahydro-pyrimidine, imidazolidine, or pyrazolidine.

3. The method of claim 2, wherein the ring comprising $R^4$, $R^5$ and the atom to which they are connected is cyclopentane, cyclohexane, piperidine, pyridine, hexahydro-pyrimidine, imidazolidine, or pyrazolidine.

4. The method of claim 3, wherein the ring comprising $R^4$ and $R^5$ and the atom to which they are connected is cyclohexane, piperidine or piperazine.

5. The method of claim 1, wherein $R^a$ and $R^b$ are independently hydrogen, methyl or ethyl, phenyl or benzyl.

6. The method of claim 1, wherein $R^a$ is $(C_1-C_6)$alkyl.

7. The method of claim 1, wherein $R^a$ is methyl, ethyl, propyl or butyl.

8. The method of claim 1, wherein $R^a$ is, methyl, ethyl, i-propyl, i-butyl or tert-butyl.

9. The method of claim 1, wherein $R^7$ is hydrogen, $(C_1-C_6)$alkyl, phenyl or phenyl$(C_1-C_6)$alkylene.

10. The method of claim 9, wherein $R^7$ is hydrogen, methyl or ethyl, phenyl or benzyl.

11. The method of claim 10, wherein $R^7$ is H, or methyl.

12. The method of claim 11, wherein $N(R^7)_2$ is amino, methylamino, dimethylamino, ethylamino, pentylamino, diethylamino or benzylamino.

13. The method of claim 12, wherein $-N(R^7)_2$ is amino, methylamino, dimethylamino, ethylamino, diethylamino or benzylamino.

14. The method of claim 13, wherein $N(R^7)_2$ is amino, or methylamino.

15. The method of claim 1, wherein X is, $CH_2OH$, $-CO_2R^a$, $-CH_2OC(O)R^a$, or $-C(O)NR^bR^c$.

16. The method of claim 15, wherein X is $CH_2OH$ or $-C(O)NR^bR^c$.

17. The method of claim 16, wherein X is $-CH_2OH$, or $-C(O)NHCH_2CH_3$.

18. The method of claim 1, wherein m is 0, 1, or 2.

19. The method of claim 1, wherein the rings comprising $R^4$, $R^5$ and the atom to which they are connected are selected from the group consisting of:

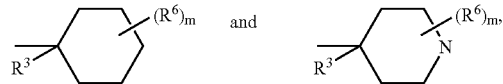

where m is from 1 to 3.

20. The method of claim 1, wherein the rings comprising $R^4$, $R^5$ and the atom to which they are connected are selected from the group consisting of:

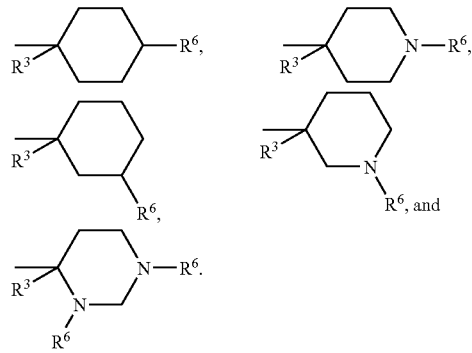

21. The method of claim 1, wherein the ring comprising $R^4$ and $R^5$ is 2-methylcyclohexane, 2,2-dimethylcyclohexane, 2-ethylcyclohexane, 2,2-diethylcyclohexane, 2-tert-butylcyclohexane, 3-methylcyclohexane, 3,3-dimethylcyclohexane, 4-methylcyclohexane, 4-ethylcyclohexane, 4-tert-butylcyclohexane, 4-carboxymethyl cyclohexane, 4-carboxyethyl cyclohexane, 3,3,5,5-tetramethyl cyclohexane, 2,4-dimethyl cyclopentane, 4-cyclohexanecarboxylic acid, or 4-cyclohexanecarboxylic acid esters.

22. The method of claim 1, wherein the ring comprising $R^4$ and $R^5$ is 4-piperidine, 4-piperidene-1-carboxylic acid, 4-piperidine-1-carboxylic acid methyl ester, 4-piperidine-1-carboxylic acid ethyl ester, 4-piperidine-1-carboxylic acid propyl ester, 4-piperidine-1-carboxylic acid tert-butyl ester, 3-piperidine, 3-piperidene-1-carboxylic acid, 3-piperidine-1-carboxylic acid methyl ester, or 3-piperidine-1-carboxylic acid tert-butyl ester.

23. The method of claim 1, wherein the compound has the formula:

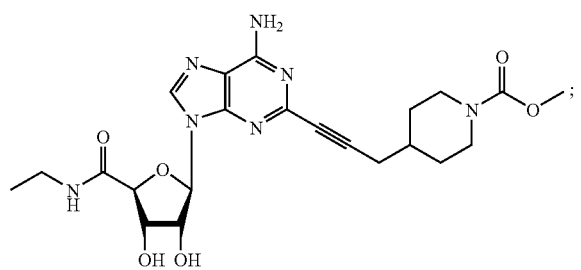
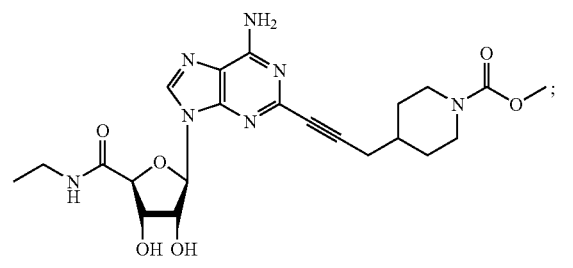
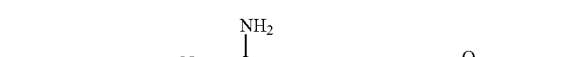
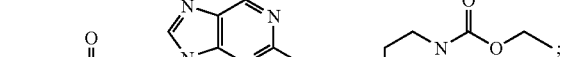
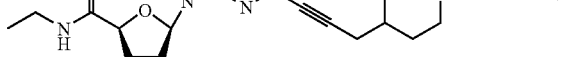
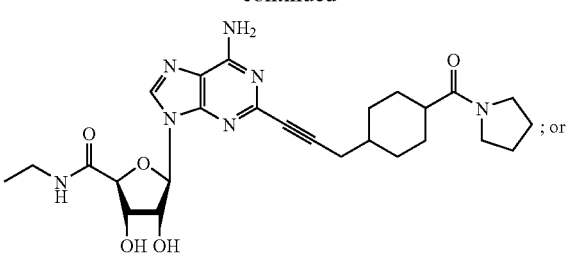
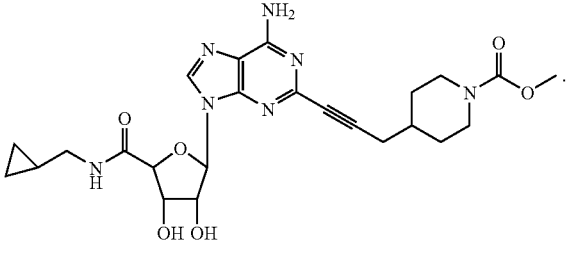
24. The method of claim 1, wherein the $A_{2A}$ adenosine receptor agonist is
ATL-146e
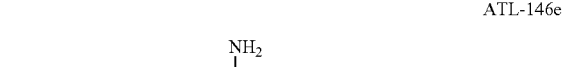
JR-1085
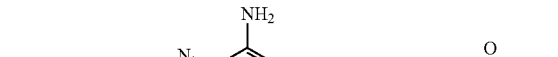
AB-1
AB-3

-continued
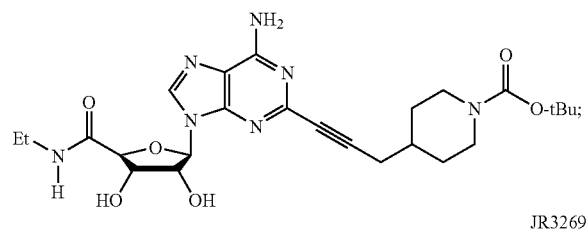
JR3259
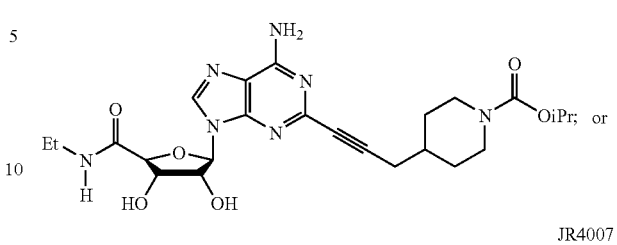
JR4009
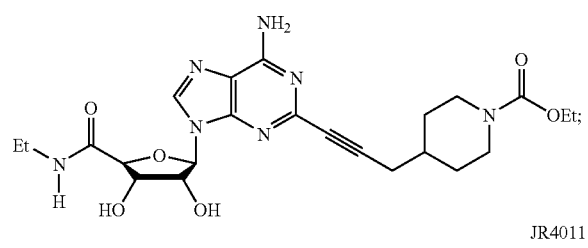
JR3269
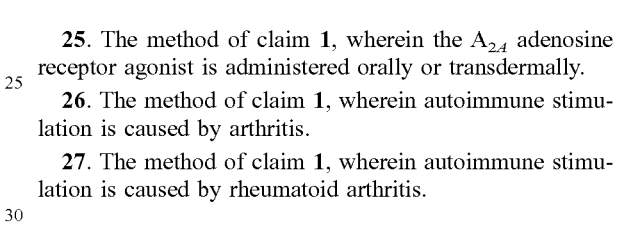
JR4007
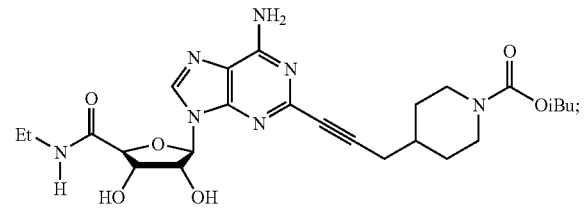
JR4011
25. The method of claim 1, wherein the $A_{2A}$ adenosine receptor agonist is administered orally or transdermally.
26. The method of claim 1, wherein autoimmune stimulation is caused by arthritis.
27. The method of claim 1, wherein autoimmune stimulation is caused by rheumatoid arthritis.
* * * * *